US007348138B2

(12) United States Patent
Weiner et al.

(10) Patent No.: US 7,348,138 B2
(45) Date of Patent: Mar. 25, 2008

(54) METHOD OF INDUCING CELL DEATH USING WEST NILE VIRUS CAPSID PROTEIN

(75) Inventors: David B. Weiner, Merion Station, PA (US); Joo-Sung Yang, Seoul (KR); Karuppiah Muthumani, Cherry Hill, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/966,576

(22) Filed: Oct. 14, 2004
(Under 37 CFR 1.47)

(65) Prior Publication Data
US 2005/0226849 A1  Oct. 13, 2005

Related U.S. Application Data

(63) Continuation of application No. 09/971,980, filed on Oct. 4, 2001, now abandoned.

(60) Provisional application No. 60/237,885, filed on Oct. 4, 2000.

(51) Int. Cl.
C12Q 1/70 (2006.01)
A61K 39/12 (2006.01)
(52) U.S. Cl. .................................. 435/5; 424/218.1
(58) Field of Classification Search .................. None
See application file for complete search history.

(56) References Cited

U.S. PATENT DOCUMENTS

| 4,722,848 | A | 2/1988 | Paoletti et al. ............. 424/89 |
| 5,017,487 | A | 5/1991 | Stunnenberg et al. ..... 435/172.3 |
| 5,077,044 | A | 12/1991 | Stocker et al. |
| 5,110,587 | A | 5/1992 | Paoletti et al. ............. 424/89 |
| 5,112,749 | A | 5/1992 | Brey, III et al. ........ 435/172.3 |
| 5,174,993 | A | 12/1992 | Paoletti ..................... 424/89 |
| 5,206,163 | A * | 4/1993 | Renard et al. ............. 435/325 |
| 5,223,424 | A | 6/1993 | Cochran et al. ............ 435/236 |
| 5,225,336 | A | 7/1993 | Paoletti ..................... 435/69.1 |
| 5,240,703 | A | 8/1993 | Cochran ..................... 424/89 |
| 5,242,829 | A | 9/1993 | Panicali et al. .......... 435/320.1 |
| 5,254,463 | A | 10/1993 | De Boer et al. |
| 5,294,441 | A | 3/1994 | Curtiss, III ................. 424/93 |
| 5,294,548 | A | 3/1994 | McLinden et al. ........ 435/235.1 |
| 5,310,668 | A | 5/1994 | Ellis et al. ............. 435/172.3 |
| 5,350,671 | A | 9/1994 | Houghton et al. |
| 5,387,744 | A | 2/1995 | Curtiss, III et al. ...... 424/235.1 |
| 5,389,368 | A | 2/1995 | Curtiss, III ............... 424/93.2 |
| 5,424,065 | A | 6/1995 | Curtiss, III et al. ........ 424/93.2 |
| 5,451,499 | A | 9/1995 | Cochran ..................... 435/5 |
| 5,453,364 | A | 9/1995 | Paoletti ..................... 435/69.3 |
| 5,462,734 | A | 10/1995 | Letchworth, III et al. ........................ 424/229.1 |
| 5,470,734 | A | 11/1995 | Sondermeijer et al. ... 424/229.1 |
| 5,482,713 | A | 1/1996 | Paoletti ..................... 424/199.1 |
| 5,489,529 | A | 2/1996 | De Boer et al. |
| 5,593,972 | A | 1/1997 | Weiner et al. .............. 514/44 |
| 5,739,118 | A | 4/1998 | Carrano et al. ............. 514/44 |
| 5,744,140 | A | 4/1998 | Paoletti et al. |
| 5,837,533 | A | 11/1998 | Boutin ..................... 435/320.1 |
| 5,861,290 | A * | 1/1999 | Goldsmith et al. ......... 435/456 |
| 5,981,505 | A | 11/1999 | Weiner et al. .............. 514/44 |
| 6,406,689 | B1 * | 6/2002 | Falkenberg et al. ........ 424/93.1 |
| 6,673,895 | B2 * | 1/2004 | Despres et al. ............ 530/324 |

FOREIGN PATENT DOCUMENTS

WO  WO 91/15574 A1 * 10/1991
WO  WO 93/22440 A1 * 11/1993

OTHER PUBLICATIONS

Chester M. Southam and Alice E. Moore, American Journal of Tropical Medicine and Hygiene, (1954), 3(1):19-50.*
Heinz-Jurgen Thiel et al., Pestiviruses, Fields Virology, Lippincott-Raven Third Edition (1996) Chapter 33, Pestiviruses, pp. 1059-1063.*
De Mitri et al., The Lancet, Feb. 18, 1995, 345:413-415.*
Ramanathan et al. Virology, 2006, 345 :56-72.*
Yang et al., Emerging Infectious Diseases, 2002, 8(12):1379-1384.*
Colman, P.M., Research Immunology, 1994, 145:33-36.*
Anderson, J.F., et al., "Direct submission," Database GENBANK, US National Library of Medician, No. AF206517, Dec. 28, 1999, 1 page.
Anderson, J.F., et al., "Isolation of west nile virus from mosquitoes, crows, and a cooper's hawk in Connecticut," *Science*, Dec. 17, 1999, 286, 2331-2333.
Chen, C., et al., "Direct interaction of hepatitis C virus core protein with the cellular lymphotoxin-β receptor modulates the signal pathway of the lymphotoxin-β receptor," *J. Virology*, Dec. 1997, 71(12), 9417-9426.
Marusawa, H., et al., "Hepatitis C virus core protein inhibits Fas- and tumor necrosis factor alpha-mediated apoptosis via NF-κB activation," *J. Virology*, Jun. 1999, 73(6), 4713-4720.
Parquet, M.D., et al., "West nile virus-inducted bax-dependent apoptosis," *FEBS Letts.*, 2001, 500, 17-24.

(Continued)

Primary Examiner—Stacy B. Chen
(74) Attorney, Agent, or Firm—Pepper Hamilton LLP

(57) ABSTRACT

This invention provides methods of inducing cell death with *Flavivirus* or *Pestivirus* capsid protein, such as West Nile virus (WNV) capsid protein, and functional fragments thereof. The invention also provides methods of treating patients suffering from diseases characterized by hyperproliferating cells by administering pharmaceutical compositions comprising WNV or other virus including *Flavivirus* or *Pestivirus* capsid or other protein or a nucleic acid molecule encoding the same. Methods of identifying compounds which have anti-viral and/or anti-WNV and/or anti-*Flavivirus* and/or anti-*Pestivirus* capsid or other protein activity are disclosed. The invention also provides vaccine compositions comprising capsid or other proteins, or fragments thereof, or nucleic acids encoding same, from WNV or other virus including *Flavivirus* or *Pestivirus* and a pharmaceutically acceptable carrier. The invention also provides diagnostic methods and kits for identifying individuals exposed to WNV or other viruses including *Flavivirus* or *Pestivirus*.

3 Claims, 30 Drawing Sheets

OTHER PUBLICATIONS

Ray, R.B., et al., "Inhibition of tumor necrosis factor (TNF-α)-mediated apoptosis by hepatitis C virus core protein," *J. Biological Chemistry*, Jan. 23, 1998, 273(4), 2256-2259.
Ray, R.B., et al., "Suppression of apoptotic cell death by hepatitis C virus core protein," *J. Virology*, 1996, 226, 176-182.
Ruggieri, A., et al., "Sensitization to fas-mediated apoptosis by hepatitis C virus core protein," *J. Virology*, 1997, 229, 68-76.
Shrivastava, A., et al., "Ectopic expression of hepatitis C virus core protein differentially regulates nuclear transcription factors," *J. Virology*, Dec. 1998, 72(12), 9722-9728.
Yang, J.S., et al., "Induction of potent Th1-type immune responses from a novel DNA vaccine for west nile virus New York isolate (WNV-NY1999)," *Dept. Pathology and Laboratory Medicine*, Oct. 2001, 184, 809-816.
Zhu, N., et al., "Hepatitis C virus core protein binds to the cytoplasmic domain of tumor necrosis factor (TNF) receptor 1 and enhances TNF-induced apoptosis," *J. Virology*, May 1998, 72(5), 3691-3697.
Neyts, J. et al., "Infections with *Flaviviridae*," *Verh K Acad Geneeskd Belg*, 1999, 61, 661-697.
Salgame, P. et al., "An ELISA for detection of apoptosis," *Nucl Acids Res*, 1997, 25(3), 680-681.
Seder, A. and Paul, W., "Acquisition of lymphokine-producing phenotype by CD4+ T cells," *Annu. Rev Immunol*, 1994, 12, 635-673.
Sherlock, S., "The hepatic *Flaviviridae*: summary," *J Viral Hepat*, 1999, 6, Suppl. 1,1-5.
Stewart, S. et al., "Human Immunodeficiency Virus Type 1 Vpr Induces Apoptosis following Cell Cycle Arrest," *J Virol*, 1997, 71(7), 5579-5592.
Utz, P. and Anderson, P., "Life and death decisions: regulation of apoptosis by proteolysis of signaling molecules," *Cell Death Differ*, 2000, 7, 589-602.
Wide, L., "Solid Phase Antigen-Antibody Systems," *Radioimmune Assay Method*, Kirkham, ed., E. & S. Livingstone, Edinburgh (1971) pp. 405-413.
GenBank Accession No. AAA81039: Collman, R. et al., "VPR protein (Human immunodeficiency virus type 1)," Aug. 10, 2000.
GenBank Accession No. AAA96744: Volchkov, V.E. et al., "envelope glycoprotein," Apr. 11, 1996.
GenBank Accession No. AAC23593: Hsu et al., "Bcl-2 related ovarian death gene product BOD [Rattus norvegicus]," Mar. 11, 1999.
GenBank Accession No. AAC53582: Inohara, N. et al., "apoptosis activator Mtd [Mus musculus]," May 5, 1998.
GenBank Accession No. AAC57106: Moore, P.S. et al., "ORF 25; major capsid protein MCP homolog; EBV BcLF1 homolog [Human herpesvirus 8]," May 2, 1997.
GenBank Accession No. AAG30730: Tolou, H. et al., "polyprotein [Dengue virus type 2]," Nov. 8, 2000.
GenBank Accession No. AAG40164: Volchkov, V.E. et al., "nucleoprotein NP [Ebola virus]," Dec. 14, 2000.
GenBank Accession No. AAK54467: Yin, P. et al., "minor reovirus core protein mu2 [Mammalian orthoreovirus 2]," Jun. 15, 2001.
GenBank Accession No. AF094612: Pisano, M.R. et al., "Yellow fever virus strain Trinidad 79A isolate 788379, complete genome," Jan. 20, 2000.
GenBank Accession No. AF196835: Lanciotti, R.S. et al., "West Nile virus strain NY99-flamingo382-99, complete genome," Dec. 7, 2000.
GenBank Accession No. AF202541: Jia, X.Y. et al., "West Nile virus strain HNY1999 polyprotein (C, prM, E, NS1, NS2a, NS2b, NS3, NS4a, NS5) gene, complete cds," Dec. 16, 1999.
GenBank Accession No. AF206518: Anderson, J.F. et al., "West Nile virus isolate 2741, complete genome," May 8, 2000.
GenBank Accession No. BAA00176: Coia, G. et al., "polyprotein [Kunjin virus]," Feb. 17, 1998.
GenBank Accession No. CAB75953: Barbarossa, L., "2a protein [cucumber mosaic virus]," Feb. 24, 2000.
GenBank Accession No. CAC22429: Zhang, H. et al., "Human Bad [Homo sapiens]," Jan. 17, 2001.

GenBank Accession No. D90194: Aihara, S. et al., "Japanese encephalitis virus strain SA(V), complete genome," Feb. 7, 1999.
GenBank Accession No. D90195: Aihara, S. et al., "Japanese enchephalitis virus strain SA(A), complete genome," Feb. 7, 1999.
GenBank Accession No. M12294: Castle, E. et al., "West Nile virus RNA, complete genome," Dec. 4, 2000.
GenBank Accession No. M16614: Trent, D. W. et al., "St. Louis encephalitis virus capsid, membrane, envelope and nonstructural proteins (NS1, NS2a, NS2b, NS3) mRNAs, complete cds," Aug. 3, 1993.
GenBank Accession No. M18370: Sumiyoshi, H. et al., "Japanese encephalitis virus (strain JaOArS982), complete genome," Nov. 15, 1995.
GenBank Accession No. M23027: Mason, P.W. et al., "Dengue virus type 1 polyprotein encoding capsid (C), membrane proteins (prM and M), envelope protein (E), and nonstructural protein (NS1) RNA, 5' end," Jul. 20, 1994.
GenBank Accession No. M31182: Collett, M.S. et al., "Bovine viral diarrhea virus complete genome," Aug. 2, 1993.
GenBank Accession No. NP_033884: O'Connor, L., "Bcl2 interacting mediator of cell death [Mus musculus]," Nov. 1, 2000.
GenBank Accession No. NP_059434: Sumiyoshi, H. et al., "JEV polyprotein [Japanese encephalitis virus]," Jun. 14, 2000.
GenBank Accession No. NP_062889: Strauss, E.G. et al., "p230 nonstructural polyprotein [Sindbis virus]," Nov. 1, 2000.
GenBank Accession No. NP_112026: Chua, K.B et al., "fusion protein [Nipah virus]," Apr. 3, 2001.
GenBank Accession No. Q16611: Farrow, S.N. et al., "BCL-2 homologous antagonist/killer (apoptosis regulator BAK)," Aug. 20, 2001.
GenBank Accession No. U17066: dos Santos, C.N. et al., "Yellow fever virus vaccine strain 17DD, complete genome," May 24, 1995.
GenBank Accession No. U17067: dos Santos, C.N. et al., "Yellow fever virus vaccine strain 17D-213, complete genome," May 24, 1995.
GenBank Accession No. U21055: Wang, E. et al., "Yellow fever virus French neurotropic strain, complete genome," May 16, 1996.
GenBank Accession No. U21056: Wang, E. et al., "Yellow fever virus French viscerotropic strain, complete genome," May 16, 1996.
GenBank Accession No. U54798: Pisano, M.R. et al., "Yellow fever virus strain 85-82H, complete genome," May 16, 1996.
GenBank Accession No. U88535: Puri, B. et al., "Dengue virus type 1 clone WestPac, complete genome," Sep. 19, 1997.
GenBank Accession No. U88536: McKee, K.T,. Jr. et al., "Dengue virus type 1 clone 45AZ5, complete genome," Sep. 19, 1997.
GenBank Accession No. U88537: McKee, K.T., Jr. et al., "Dengue virus type 1 clone 45AZ5-PDK27, complete genome," Sep. 19, 1997.
GenBank Accession No. X03700: Rice, C.M. et al., "Yellow fever virus genome (17D vaccine strain)" Feb. 17, 1997.
GenBank Accession No. XP_009093: NCBI Annotation Project, "BCL2-associated X protein [Homo sapiens]," Oct. 16, 2001.
GenBank Accession No. XP_009825: NCBI Annotation Project, "BH3 interacting domain death agonist [Homo sapiens]," Oct. 16, 2001.
GenBank Accession No. XP_015353: NCBI Annotation Project, "BCL2-interacting killer [Homo sapiens]," Apr. 17, 2001.
Agadjanyan, M. et al., "CD86 (B7-2) can function to drive MHC-restricted antigen-specific cytotoxic T lymphocyte responses in vivo," *J Immunol*, 1999, 162, 3417-3427.
Ayyavoo, V. et al., "HIV1-Vpr supresses immune activation and apoptosis through regulation of nuclear factor κB," *Nat Med*, 1997, 3, 1117-1123.
Chattergoon, M. et al., "Specific Immune Induction Following DNA-Based Immunization Through In Vivo Transfection and Activation of Macrophages/Antigen-Presenting Cells," *J Immunol*, 1990, 160, 5707-5718.
Chattergoon, M. et al., "Targeted antigen delivery to antigen-presenting cells including dendritic cells by engineered Fas-mediated apoptosis," *Nat Biotechnol* 2000, 1, 974-979.
Finkelman, F. et al., "Lymphokine control of in vivo immunoglobulin isotype selection," *Ann Rev Immunol*, 1990, 8, 303-333.

Holloway, M., "Outbreak not contained. West Nile virus triggers a reevaluation of public health surveillance," *Sci Am*, Apr. 2000 282, 20 and 22.

Kaufmann, S. et al., "Detection of DNA Cleavage in Apoptotic Cells," *Methods Enzymol*, 2000, 32, Reed, J., (Ed.), Academic Press, 3-15.

Kim, C. et al., "Codon optimization for high-level expression of human erythropoietin (EPO) in mammalian cells," *Gene* 1997, 199, 293-301.

Kim, J. et al., "Macrophage colony stimulating factor (M-CSF) can modulate immune responses and attract dendritic cells in vivo," *Human Gene Therapy*, 2000, 11, 305-321.

Kim, J. et al., "CD8 positive T cells controls antigen-specific immune responses through the expression of chemokines," *J Clin. Invest*, 1998 10342, 1112-1124.

Kim J. et al., "Engineering of in vivo immune responses to DNA immunization via co-delivery of costimulatory molecule genes," *Nat Biotechnol*, 1997, 15, 641-646.

Leyssen, P. et al., "Perspectives for the treatment of infections with *Flaviviridae*," *Clin Microbiol Rev*, 2000, 13, 67-82.

Morgan, D. et al., "Selective in vitro growth of T lymphocytes from normal human bone marrows," *Science*, 1976, 193, 1007-1008.

Chen et al., "Screening of Protective Antigens of Japanese Encephalitis Virus by DNA Immunization; a Comparative Study with Conventional Virus Vaccines," *J. Virol.* (1999) 73(12):10137-10145.

De Smith "Control of Translation by mRNA Secondary Structure in *Escherichia Coli*," *J. Mol. Biol.* (1994) 244:144-150.

Khromykh et al., "Encapsidation of the Flavivirus Kunjin Replicon RNA," *J. Of Virology* (1998) 72:5967-5977.

Mukund et al., "Effect of mRNA Secondary Structure in the Regulation of Gene Expression: Unfolding of Stable Loop Causes the Expression of Taq Polymerase in *E. Coli*," *Current Science* (1999) 76(11):1486-1490.

Suo et al., "RNA Secondary Structure Switching During DNA Synthesis Catalyzed by HIV-1 Reverse Transcriptase," *Biochemistry* (1997) 36:14778-14785.

Tardei et al., "Evaluation of Immunoglobulin (IgM) and IgG Enzyme Immunoassays in Serologic Diagnosis of West Nile Virus Infection," *J. of Clinical Microbiology* (2000) 38:2232-2239.

European Search Report dated Dec. 13, 2004 for European Application No. 01979543.

International Search Report dated Apr. 24, 2003 for International Application No. PCT/US01/31451.

International Search Report dated Apr. 24, 2002 for International Application No. PCT/US01/31355.

Khromykh et al, "Encapsidation of the Flavivirus Kunjin Replicon RNA by Using a Complementation System Providing Kunjin Virus Structural Proteins in *trans*," Journal of Virology (1998), 72(7), 5967-5977.

Tardei et al, "Evaluation of Immunoglobulin M (IgM) and IgG Enzyme Immunoassays in Serologic Diagnosis of West Nile Virus Infection," Journal of Clinical Microbiology (2000) 38(6), 2232-2239.

Koraka et al, "Reactivity of Serum Samples from Patients with a Flavivirus Infection Measured by Immunofluorescence Assay and ELISA", Microbes and Infection (2002) 4, 1209-1215.

* cited by examiner

Genomic organization of WNV-HNY1999

5'UTR — Cp (Pre-M, Pr M), Env, NS1, NS2A, NS2B, NS3, NS4A, NS4B, NS5 — 3'UTR (10945 bp)

Cloning Strategy for WNV-HNY1999 Capsid Gene: pWNVh-DJY, pWNVy-DJY

Hu-sIgE leader sequence — Cp

Primers:
- sigh-VChU1+ / sigy-VCyU1.1+
- sigh-VChU2+
- sigh-VChU3+
- sigh-VChL1-
- sigh-VChL2-
- sigh-VChL3-

PCR:
- sigh-VChFS1+ / sigy-VCyFS1.1+
- sigh-VChFAS2-

Overlapping PCR

Hind III — Synthetic WNVCp gene — Not I

Cloning into expression vector

CMVpro — Hind III — Not I — Polyhistidine tag — BGH polyA pcDNA3.1-His plasmid

FIG 1

FIGURE 4 (Page 1 of 4)

FIGURE 4 (Page 2 of 4)

FIGURE 4 (Page 3 of 4)

FIGURE 4 (Page 4 of 4)

FIGURE 7 (Page 1 of 4)

FIGURE 7 (Page 2 of 4)

FIGURE 7 (Page 3 of 4)

FIGURE 7 (Page 4 of 4)

$^{35}$S-Labelled *in vitro* Translated Products of pWNVCh-DJY and pWNVCy-DJY

FIG 8

WNV Capsid (Cp) Peptides - Location and Sequences

```
                     10         20         30         40         50         60         70         80         90        100        110        120
WNV Cp
Amino Acid    MSKKPGGPGKSRAVNMLKRGMPRVLSLIGLKRAMLSLIDGKGPIRFVLALLAFFRFTAIAPTRAVLDRWRGVNKQTAMKHLLSFKKELGTLTSAINRRSSKQKKRGGKTGIAVMIGLIASVGA
Sequence Peptide Seq.  SKKPGGPGKSRAVNMLKRGMPR       KRAMLSLIDGKGPIRFVLA                                              TLTSAINRRSSKQKKRGGKTGI
Peptide Name        WNVC-P1                      WNVC-P2                                                         WNVC-P3
```

FIG. 9

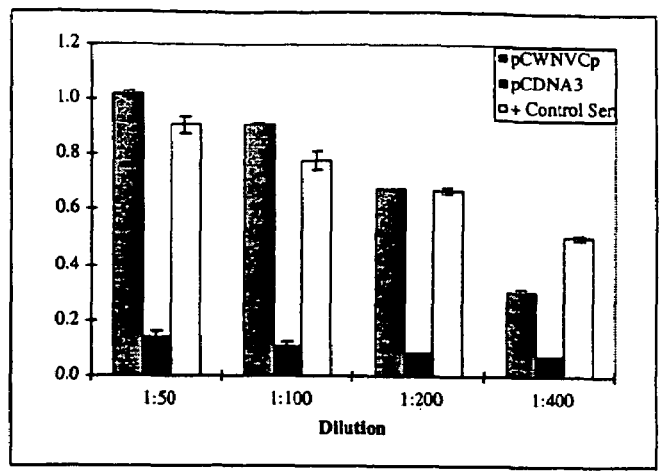
Fig. 12A
Fig. 12B
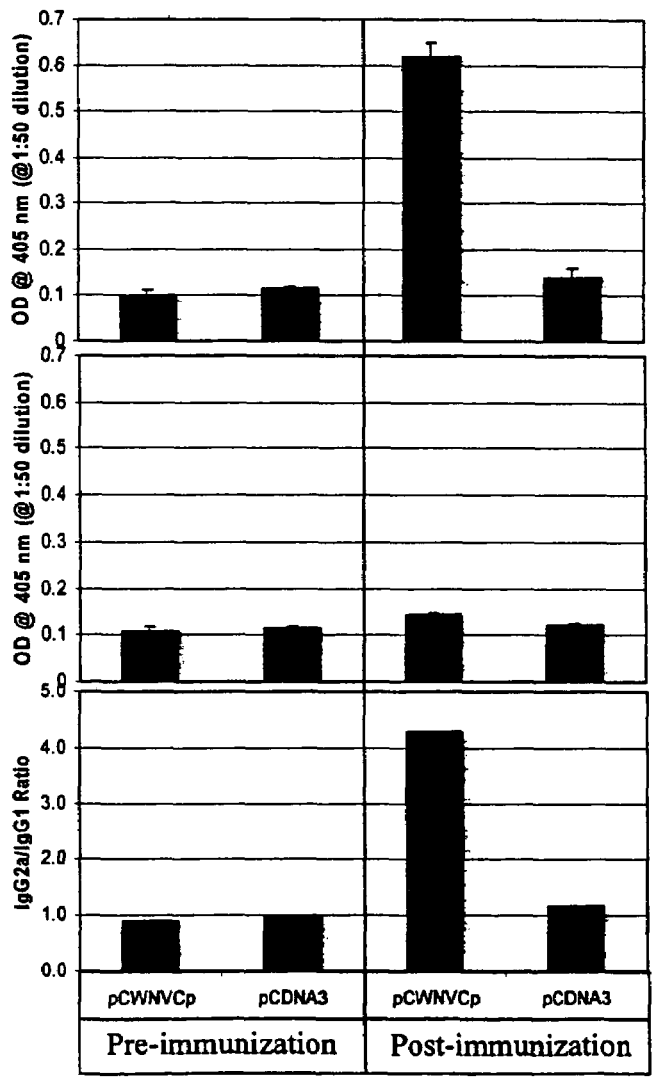
Fig. 12C
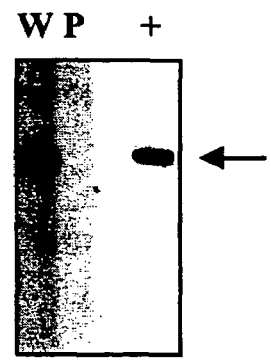

Figure 17

```
KJV Cp        10         20         30         40         50         60         70         80         90        100        110        120
[568]  MSKKPGGPGKSRAVNMLKRGMPRVLSLTGLKRAMLSLIDGRGPTRFVLALLAPFRFTAIAPTRAVLDRMRSVNKQTAMKHLLSFKKELGTLTSAINRRSSKQKKRGGKTGIAFMIGLIAGVGA>
       ||||||||||||||||||||||||||||||||||||||||*||||||||||||||||||||||||||||||||||||||||||||||||||||||||||||||||||||||||||
MNVCp  MSKKPGGPGKSRAVNMLKRGMPRV

FIGURE 18 (Page 1 of 3)

Fig. 18 Alignment of WNVCp protein sequence to other viral proteins

```
Search Analysis for Sequence: WNVCaa        Matrix: pan250

FIGURE 18 (Page 2 of 3)

```
4. Ebola glycoprotein    120         130
4. EbolaGlyc       KPDGSECLPAA

Fig. 18 (continued) Alignment of WNVCp protein sequence to proapoptotic proteins

```

FIGURE 19 (Page 1 of 4)

Fig. 19 Alignment of HIV-1 89.6 Vpr protein sequence to other viral proteins

```
Search Analysis for Sequence: HIV-1 89.6 VpraaMatrix: pam250 matrix
Search from 1 to 96 where origin = 1         Score Region from 1 to 96
Date: June 15,2001                           Maximum possible score: 515
Time: 19:57:09

Database: UserFolder: Alignment-AC6/01

10        20        30        40        50        60        70        80        90
HIV-1 89.6  MEQAPEDQGPQREPYNDWTLELLEELKNEAVRHFPRIWLHSLGQHIYETYGDTWTGVEALIRILQQLLFIHFRIGCRHSRIGIIQQRRTRNGASKS 1. p230 nonstructural protein/ Sindbis virus
1. p230nonst                     1320      1330      1340
[   50 ]                     FRQLDNSRTRQFTPHHLNCVISSVYEG--T-RDGVGA>
                             | || |   |||   || |   |||    | || |
HIV-1 89.6                   LEELKNEAVRHFPRIWLHSLGQHIYETYGDTWTGVEA 2. West Nile Virus capsid protein
2. WNVCaa                                          70        80        90        100       110
[   45 ]                                       RWRGVNKQTA-MKHLLSFKKELGTLTSAINRRSSKQKKRGGKTG>
                                               | |||      ||||| |   ||   | |   || | || |
HIV-1 89.6                                     TWTGVEALIRILQQLLFIHFRIGCRHSRIGIIQQRRTRNGASKS 3. Cucumovirus 2A protein
3. Cumbermos                                                          10
[   36 ]                                                          DFHRFSYIRDRRA>
                                                                   ||| ||||||
HIV-1 89.6                                                        RHSRIGIIQQRRT
```

FIGURE 19 (Page 2 of 4)

```
4. Cucumovirus 2A protein
4. Cumbermos                                          110       120
[   40 ]                                               EFGNTFSVPDPLR-EVQRL>
                                                        |||| |   |||    ||||
HIV-1 89.6                                             TYGDTWTGVEALIRILQQL 5. Rubella virus capsid protein
5. Rubellaca                                 160
[   33 ]                                    WLWSEGQGAVFY>
                                            ||| || |  ||
HIV-1 89.6                                  RIWLHSLGQHIY 6. Nipah virus fusion protein
6. NipahFusi
[   44 ]                                                     .sky.sd...vf->
                                                             | |  |  |||||
HIV-1 89.6                                                   LIRILQQLLFIHF 7. Reovirus core-minor form Mu2
7. Minor-Reo     410       420       430
[   46 ]          IGAVLPKGSFKSTIMRVLDEMEVLGVRIMPR>
                   |    | |||   | |||||   |||  ||
HIV-1 89.6        EDQGPQREPYNDWTLELLEELKNEAVRHFPR
```

FIGURE 19 (Page 3 of 4)
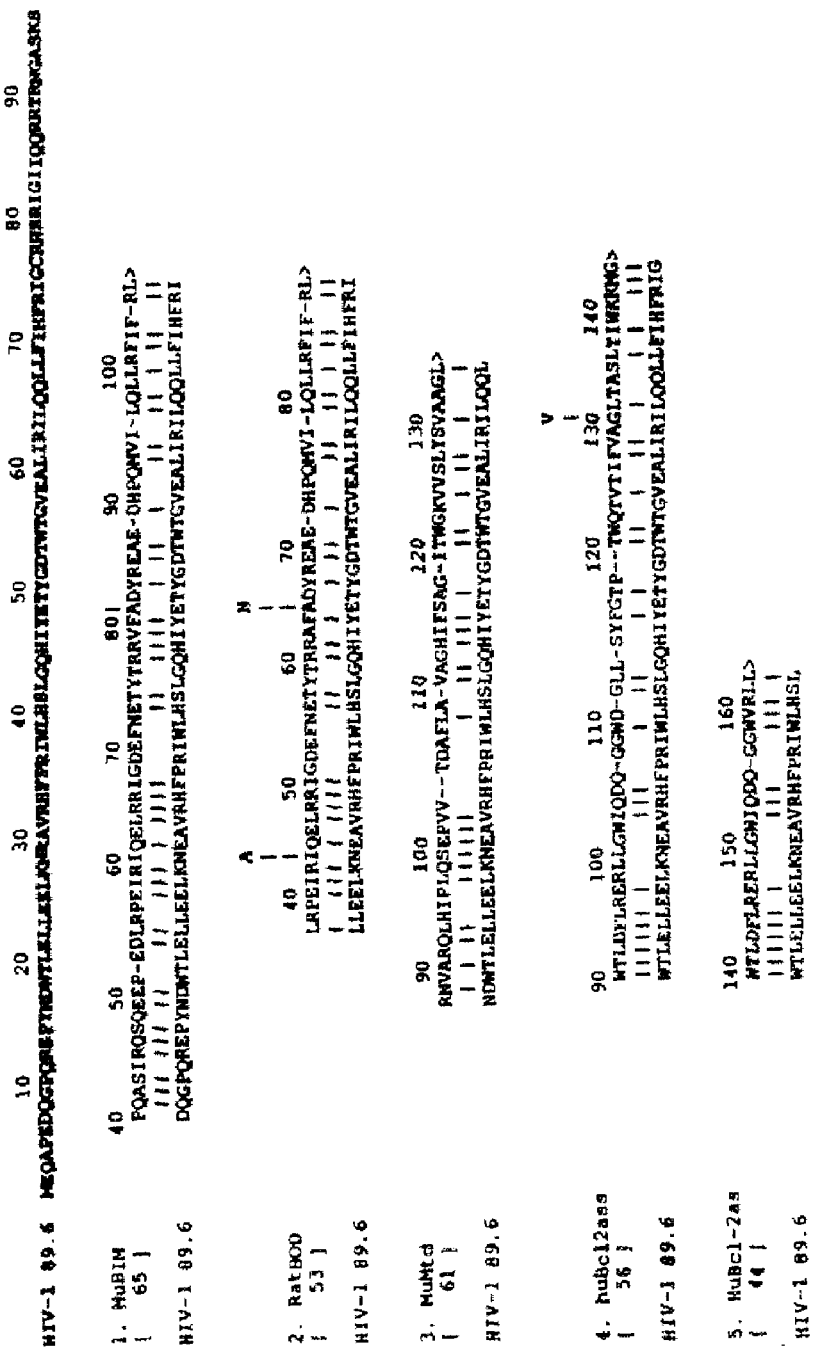

FIGURE 19 (Page 4 of 4)

```
          150        160
 6. HuBad  VFQSWMDRNLGR>
    361    -  ||||||
 HIV-1 89.6 HFPRIWLHSLGQ
```

METHOD OF INDUCING CELL DEATH USING WEST NILE VIRUS CAPSID PROTEIN

CROSS-REFERENCE TO RELATED APPLICATIONS

This application is a continuation of U.S. patent application Ser. No. 09/971,980, filed Oct. 4, 2001, abandoned. This application claims benefit under 35 U.S.C. § 119 (e) of U.S. Provisional Patent Application Ser. No. 60/237,885, filed Oct. 4, 2000, incorporated herein by reference.

FIELD OF THE INVENTION

The invention relates to the use of the capsid protein from West Nile virus, and capsid and other proteins from other viruses including viruses of the *Flavivirus* and *Pestivirus* genuses, to induce the death of cells by apoptosis, and to vaccines and diagnostics for West Nile virus and other viruses including *Flavivirus* and *Pestivirus* infections. The invention also relates to methods of screening for antiviral compounds by identifying compounds that selectively inhibit the ability of capsid protein to induce apoptosis.

BACKGROUND OF THE INVENTION

West Nile virus (WNV) infection has recently emerged in temperate regions of Europe and North America, presenting a threat to humans, horses, and birds. The most serious manifestations of WNV infection is fatal encephalitis. WNV, originally isolated in the West Nile District of Uganda in 1937, is a *Flavivirus* of the Flaviviridae family, having a size of 40-60 nm, an enveloped, icosahedral nucleocapsid, and a positive-sense, single-stranded RNA genome of 10,000-11,000 bases. For a recent review of WNV, see Holloway, 2000, Outbreak not contained. West Nile virus triggers a reevaluation of public health surveillance, Sci. Am., 282:20,22, which is incorporated herein by reference. Reviews of the viruses in the Flaviviridae family are provided in the following references: Neyts et al., 1999, Infections with Flaviviridae, Verh. K. Acad. Geneeskd. Belg., 61:661-697, discussion 697-699; Leyssen, et al., 2000, Perspectives for the treatment of infections with Flaviviridae, Clin. Microbiol. Rev., 13:67-82; Sherlock, 1999, The hepatic Flaviviridae: summary, J. Viral. Hepat., 6 Suppl. 1:1-5; and Fields, Knipe, & Howley, eds., Fields Virology (3$^{rd}$ ed.) Vols. I & II, Lippincott Williams & Wilkins Pubs. (1996), each of which is incorporated herein, in its entirety, by reference.

There is a need for improved methods of prophylactic and therapeutic treatment of *Flavivirus* and *Pestivirus* infection. There is a need for improved methods of inducing cell death and of treating diseases characterized by hyperproliferating cells.

SUMMARY OF THE INVENTION

The present invention provides methods of inducing the death of cells. The methods of the invention comprise the step of contacting cells with an amount of a *Flavivirus* or *Pestivirus* capsid protein, or functional fragment thereof, effective to induce cell death. According to some embodiments of the invention, the *Flavivirus* capsid protein, or functional fragment thereof, is the capsid protein, or functional fragment thereof, of West Nile virus (WNV). According to some embodiments of the present invention, cells are contacted with *Flavivirus* or *Pestivirus* capsid protein, or a functional fragment thereof, in order to induce the cells to die. According to some embodiments of the present invention, a nucleic acid molecule that comprises a sequence which encodes a *Flavivirus* or *Pestivirus* capsid protein, or a functional fragment thereof, is introduced into the cells. Expression of the sequence that encodes the *Flavivirus* or *Pestivirus* capsid protein, or functional fragment thereof, results in the production of the *Flavivirus* or *Pestivirus* capsid protein, or functional fragment thereof, within the cell, causing the cell to die. According to some embodiments of the present invention, the sequence which encodes the *Flavivirus* or *Pestivirus* capsid protein, or functional fragment thereof, is operably linked to regulatory elements which are necessary for expression of the sequence in the cell. According to some embodiments of the present invention, the nucleic acid molecule is DNA. According to some embodiments of the invention, the cells are tumor cells.

The present invention provides methods of identifying compounds that inhibit the ability of *Flavivirus* or *Pestivirus* capsid protein, or functional fragments thereof, to induce apoptosis. Methods of the invention comprise the steps of (a) contacting cells, in the presence of a test compound, with an amount of *Flavivirus* or *Pestivirus* capsid protein, or a functional fragment thereof, sufficient to induce a measurable amount of apoptosis in the cells, and (b) comparing the amount of apoptosis that occurs when the test compound is present with the amount of apoptosis that occurs when the test compound is absent. The present invention relates to a method of identifying compounds that inhibit WNV capsid protein, or functional fragments thereof, from inducing apoptosis in cells that comprises the steps of (a) contacting cells, in the presence of a test compound, with an amount of WNV capsid protein, or a functional fragment thereof, sufficient to induce a measurable amount of apoptosis in the cells, and (b) comparing the amount of apoptosis that occurs when the test compound is present with the amount of apoptosis that occurs when the test compound is absent. According to some embodiments, the measuring step of the method is accomplished by detecting the presence of apoptosis-related markers, including phosphatidylserine (PS) of the cellular membrane, and free 3'-hydroxy termini in DNA.

The present invention relates to pharmaceutical compositions that comprise a *Flavivirus* or *Pestivirus* capsid protein, or functional fragment thereof, and a pharmaceutically acceptable carrier. According to some embodiments of the present invention, the pharmaceutical composition comprises WNV capsid protein, or a functional fragment thereof, and a pharmaceutically acceptable carrier.

The present invention relates to pharmaceutical compositions that comprise a nucleic acid molecule that comprises a sequence which encodes a *Flavivirus* or *Pestivirus* capsid protein, or functional fragment thereof, and a pharmaceutically acceptable carrier. According to some embodiments of the present invention, the pharmaceutical composition comprises a nucleic acid molecule that comprises a sequence which encodes a *Flavivirus* or *Pestivirus* capsid protein, or a functional fragment thereof, that is operably linked to regulatory elements which are necessary for expression of the sequence in the cell. The present invention relates to pharmaceutical compositions that comprise a nucleic acid molecule that comprises a sequence which encodes WNV capsid protein, or a functional fragment thereof, and a pharmaceutically acceptable carrier. According to some embodiments of the present invention, the pharmaceutical composition comprises a nucleic acid molecule that comprises a sequence which encodes WNV capsid protein, or a functional fragment thereof, that is operably linked to regulatory elements which are necessary for expression of the sequence in the cell. According to some embodiments of the present invention, a pharmaceutical composition comprises a nucleic acid molecule that is DNA.

The present invention relates to methods of treating individuals diagnosed with or suspected of suffering from diseases characterized by hyperproliferating cells which comprise the step of administering to an individual an amount of a *Flavivirus* or *Pestivirus* capsid protein, or functional fragment thereof, sufficient to kill the hyperproliferating cells. The present invention relates to methods of treating individuals diagnosed with or suspected of suffering from diseases characterized by hyperproliferating cells which comprise the step of administering to an individual an amount of WNV capsid protein, or a functional fragment thereof, sufficient to kill the hyperproliferating cells. According to some embodiments, methods comprise the steps of administering to such individuals, an effective amount of WNV capsid protein, or a functional fragment of WNV capsid protein. According to some embodiments of the present invention, the sequence that encodes the *Flavivirus* or *Pestivirus* capsid protein, or functional fragment thereof, is operably linked to regulatory elements which are necessary for expression of the sequence in cells. According to some embodiments of the present invention, methods comprise the steps of administering to such individuals, an effective amount of a nucleic acid molecule that comprises a sequence which encodes WNV capsid protein, or a functional fragment thereof. According to some embodiments of the present invention, the sequence that encodes the WNV capsid protein, or functional fragment thereof, is operably linked to regulatory elements which are necessary for expression of the sequence in cells. According to some embodiments of the present invention, the nucleic acid molecule is DNA. According to some embodiments of the present invention, the disease characterized by hyperproliferating cells is cancer or psoriasis.

The present invention relates to vaccine compositions that comprise an immunologically effective amount of capsid protein from WNV or a related member of the *Flaviviruses* or *Pestiviruses* and a pharmaceutically acceptable carrier. According to some embodiments of the present invention, the vaccine composition comprises an immunologically effective amount of an immunogenic fragment of capsid protein from WNV or a related member of the *Flaviviruses* or *Pestiviruses* and a pharmaceutically acceptable carrier.

The present invention relates to vaccine compositions that comprise a nucleic acid molecule that comprises a sequence which encodes capsid protein from WNV or a related member of the *Flaviviruses* or *Pestiviruses* and a pharmaceutically acceptable carrier. According to some embodiments of the present invention, the vaccine composition comprises a nucleic acid molecule that comprises a sequence which encodes an immunogenic fragment of capsid protein from WNV or a related member of the *Flaviviruses* or *Pestiviruses* and a pharmaceutically acceptable carrier. According to some embodiments of the present invention, the vaccine composition comprises a nucleic acid molecule that comprises a sequence which encodes and immunogenic fragment of WNV or related *Flavivirus* or *Pestivirus* capsid protein, operably linked to regulatory elements necessary for expression of the sequence in a cell. According to some embodiments of the present invention, a vaccine composition comprises a nucleic acid molecule that is DNA. According to some embodiments of the present invention, a vaccine composition comprises a plasmid.

The present invention relates, to methods of immunizing individuals against WNV or a related member of the *Flaviviruses* or *Pestiviruses*. The immune responses generated may be prophylactic or therapeutic. The methods comprise the steps of administering to the individual an immunologically effective amount of capsid protein, or immunogenic fragment thereof, from WNV or a related member of the *Flaviviruses* or *Pestiviruses*, or a nucleic acid molecule that encodes capsid protein, or an immunogenic fragment thereof, from WNV or a related member of the *Flaviviruses* or *Pestiviruses*.

The present invention relates to methods of identifying individuals exposed to capsid protein from WNV or a related *Flavivirus* or *Pestivirus* by detecting the presence of capsid protein from WNV or a related *Flavivirus* or *Pestivirus* in a sample using antibodies which specifically bind to capsid protein from WNV or a related *Flavivirus* or *Pestivirus*. The antibodies are preferably monoclonal antibodies. Quantification of the amount of capsid protein from WNV or a related *Flavivirus* or *Pestivirus* present in a sample of an individual may be used in determining the prognosis of an infected individual.

The present invention relates to kits for identifying individuals exposed to WNV or a related *Flavivirus* or *Pestivirus* and reagents used in such kits. The kits comprise a first container which contains antibodies which specifically bind to capsid protein from WNV or a related *Flavivirus* or *Pestivirus* and a second container which contains capsid protein from WNV or a related *Flavivirus* or *Pestivirus*. The antibodies are preferably monoclonal antibodies. The kits may be adapted for quantifying of the amount of capsid protein from WNV or a related *Flavivirus* or *Pestivirus* present in a sample of an individual. Such information may be used in determining the prognosis of an infected individual.

The present invention relates to methods of identifying individuals exposed to WNV or a related *Flavivirus* or *Pestivirus* by detecting the presence of antibodies against capsid protein from WNV or a related *Flavivirus* or *Pestivirus* in a sample using capsid protein from WNV or a related *Flavivirus* or *Pestivirus*. Quantification of the amount of anti-capsid protein from WNV or a related *Flavivirus* or *Pestivirus* antibodies present in a sample of an individual may be used in determining the prognosis of an infected individual.

The present invention relates to kits for identifying individuals exposed to WNV or a related *Flavivirus* or *Pestivirus* and reagents used therein. The kits comprise a first container which contains antibodies which were produced in response to exposure to capsid protein from WNV or a related *Flavivirus* or *Pestivirus* and a second container which contains capsid protein from WNV or a related *Flavivirus* or *Pestivirus*. The kits may be adapted for quantifying the amount of anti-capsid protein from WNV or a related *Flavivirus* or *Pestivirus* antibodies present in a sample of an individual. Such information may be used in determining the prognosis of an infected individual.

BRIEF DESCRIPTION OF THE DRAWINGS

FIG. 1 presents, at the top, a schematic representation of the genomic organization of the 1999 New York human isolate of WNV (WNV-HNY 1999) (GenBank accession number AF202541, Jia et al., 1999, Lancet, 354:1971-1972, which is incorporated herein by reference). The capsid protein is indicated as "Cp." The bottom of the figure presents a schematic representation of the construction of WNV capsid protein expression vectors pWNVh-DJY and pWNVy-DJY. These expression constructs may also be referred to herein by alternate terms. pWNVC-DJY may be referred to herein as pWNVCh-DJY or pWNVCh, and pWNVy-DJY may be referred to herein as pWNVCy-DJY or pWNVCy.

FIG. 4 presents the complete, annotated, double-stranded nucleotide sequence of WNV capsid protein expression vector pWNVh-DJY, having 5864 nucleotide base pairs. Restriction endonuclease sites, features, and translation information for parts of the protein that the construct expresses are indicated in the annotations. The top nucleotide strand is SEQ ID NO:1. The protein sequence of the amino-terminal sIgE leader peptide (SEQ ID NO:2) is presented below its coding region of nucleotides 917 through 970. The protein sequence of the WNV Cp protein portion of the expressed protein (SEQ ID NO:3) is presented below its coding region of nucleotides 971 through 1336.

FIG. 7 presents the complete, annotated, double-stranded nucleotide sequence of WNV capsid protein expression vector pWNVy-DJY, having 5864 nucleotide base pairs. Restriction endonuclease sites, features, and translation information for parts of the protein that the construct expresses are indicated in the annotations. The top nucleotide strand is SEQ ID NO:4. The protein sequence of the amino-terminal sIgE leader peptide is presented below its coding region of nucleotides 917 through 970. The protein sequence of the WNV Cp protein portion of the expressed protein is presented below its coding region of nucleotides 971 through 1336.

FIG. 8 presents an autoradiograph of electrophoretically resolved, immunoprecipitated, $^{35}S$-labeled, in vitro transcription/translation products of the two different WNV capsid protein constructs: pWNVh-DJY and pWNVy-DJY. The first lane on the left contains molecular weight markers. The arrow indicates the position of the major in vitro translated protein product. The proteins, which are fusions with polyhistidine C-terminal tags, were immunoprecipitated using an anti-His antibody.

FIG. 9 shows the complete amino acid sequence of WNV Cp protein (SEQ ID NO:5). The three major histocompatibility (MHC) class 1'-restricted epitope peptides (WNVC-P1 (SEQ ID NO:6), WNVC-P2 (SEQ ID NO:7), and WNVC-P3 (SEQ ID NO:8)), used in the studies presented herein in Example 3, are shown below the Cp amino acid sequence.

FIGS. 12A, 12B, and 12C show the WNV Capsid protein (Cp)-specific antibody response in mice following immunization. FIG. 12A: 100 μg of pCWNVCp expression cassette or control vector was injected intramuscularly at weeks 0, 4, and 8. The sera samples were collected at various days post-immunization and assayed for WNVCp-specific antibody at 1:50, 1:100, 1:200, and 1:400 dilutions. At five months post-immunization, WNVCp-specific antibody responses were detected. The error bars represent the standard deviation of the results from the immunized animals (n=3). FIG. 12B: IgG-subset analysis of WNVCp-specific IgG antibody responses was conducted. WNVCp-specific IgG1 and IgG2a responses examined at 5 months post-immunization as well as the IgG2a/IgG1 ratio are shown. FIG. 12C: WNVCp-specific serum antibody was determined by immunoprecipitation/Western blot analysis. Each immobilized membrane strip was incubated with immune sera from pCWNVCp (W) or pcDNA3 (P). As a positive control, a strip was incubated with an anti-6× His monoclonal antibody (+).

FIG. 15A: Splenocytes from immunized mice were tested for CTL response using target cells treated with pooled WNV Capsid peptides. FIG. 15B: Supernatants from effectors stimulated for CTL assay were collected at day five and tested for IFN-γ production. The error bars represent standard deviation (S.D.) values for each experiment.

FIG. 16C: Identity of the muscle infiltrating cells in pCWN-VCp immunized mice. The cells were harvested as described in Example 11, and were identified by FACS using antibodies to CD4, CD8, Mac3, CD11c, CD86, and B220.

FIG. 17 shows the alignment of WNV Cp protein sequence with portions of the sequences of capsid proteins from other *Flaviviruses*. The top comparison is between the first 123 amino acids of Cp protein from Kunjin virus (KJV;

Figure 2:
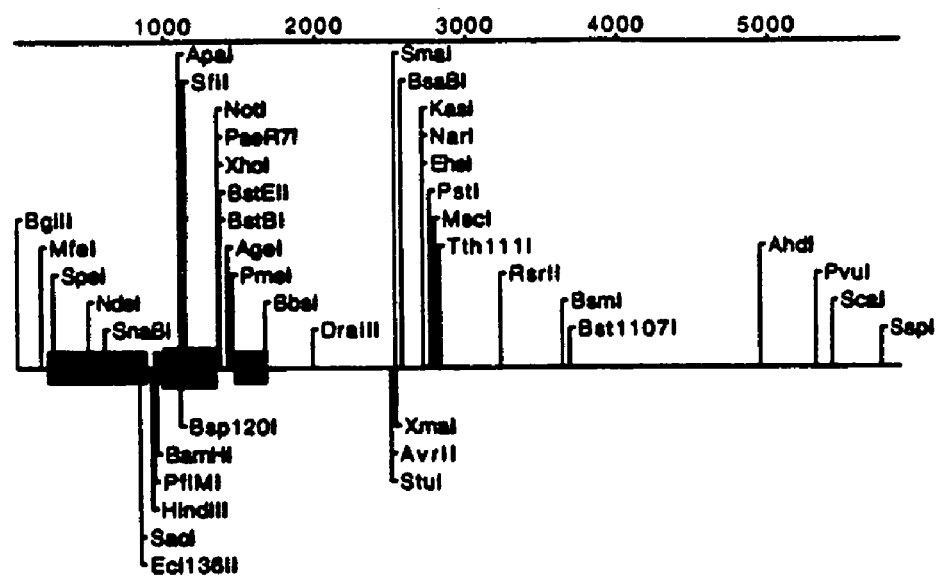
FIG. 2 presents the restriction endonuclease map of WNV capsid protein expression vector pWNVh-DJY.

GenBank accession number BAA00176 (gi:221967), which is incorporated herein by reference) (SEQ ID NO:9) and the complete 123 amino acid sequence of WNV Cp protein. The middle comparison is between the first 113 amino acids of Cp protein of a Japanese encephalitis virus (JEV; GenBank accession number NP_059434 (gi:9626461), which is incorporated herein by reference) (SEQ ID NO:10) and the first 114 amino acids of WNV Cp protein (SEQ ID NO:11). The bottom comparison is between amino acids from an internal portion of the Cp protein of a Dengue virus (DEN2; GenBank accession number AAG30730 (gi:11119732), which is incorporated herein by reference) (SEQ ID NO:12) and amino acids 10 through 98 of WNV Cp protein (SEQ ID NO:13). This alignment required looping out of a lysine (K appearing above the line) from the stretch of amino acids LTKR in the DEN2 sequence. The values in brackets are identity/homology scores, where a maximum possible score is 590. Comparisons and alignments were generated by Mac Vector.

FIG. 18 shows the alignment of the WNV Cp protein sequence with portions of the sequences of proteins from other viruses and with portions of the sequences of proapoptotic proteins. The complete sequence of the WNV Cp protein (amino acids 1-123) appears at the top in bold. Shown are 6 comparisons of WNV Cp with other viral proteins and 5 comparisons of WNV Cp with proapoptotic proteins. The viral protein comparisons are as follows: 1) amino acids from an internal portion of Human Immunodeficiency Virus-1 (HIV-1) 89.6 Vpr protein (GenBank accession number AAA81039 (gi:1055033), which is incorporated herein by reference) (SEQ ID NO:27) and amino acids 68 through 110 of WNV Cp protein (SEQ ID NO:28); 2) amino acids from an internal portion of Herpes Simplex Virus major capsid protein (GenBank accession number AAC57106 (gi:1718277), which is incorporated herein by reference) (SEQ ID NO:29) and amino acids 8 through 117 of WNV Cp protein (SEQ ID NO:30); 3) amino acids from an internal portion of Ebola virus nuclear protein (GenBank accession number AAG40164 (gi: 11761746), which is incorporated herein by reference) (SEQ ID NO:31) and amino acids 10 through 117 of WNV Cp protein (SEQ ID NO:32); 4) amino acids from an internal portion of Ebola virus glycoprotein (GenBank accession number AAA96744 (gi:1141779), which is incorporated herein by reference) (SEQ ID NO:33) and amino acids 4 through 23 of WNV Cp protein (SEQ ID NO:34); 5) amino acids from another internal portion of Ebola virus glycoprotein (SEQ ID NO:35) and amino acids 50 through 73 of WNV Cp protein (SEQ ID NO:36); and 6) amino acids from an internal portion of Rubella virus capsid protein (GenBank accession number GNWVR4 (gi:74519), which is incorporated herein by reference) (SEQ ID NO:37) and amino acids 64 through 114 of WNV Cp protein (SEQ ID NO:38). The proapoptotic protein comparisons are as follows: 1) amino acids from an internal portion of the human BAK protein (GenBank accession number Q16611 (gi:2493274), which is incorporated herein by reference) (SEQ ID NO:39) and amino acids 17 through 63 of WNV Cp protein (SEQ ID NO:40); 2) amino acids from an internal portion of the human Bc-12 associated X protein (GenBank accession number XP_009093 (gi:15304386), which is incorporated herein by reference) (SEQ ID NO:41) and amino acids 109 through 123 of WNV Cp protein (SEQ ID NO:42); 3) amino acids from an internal portion of the human BIK protein (GenBank accession number XP_015353 (gi:13655199), which is incorporated herein by reference) (SEQ ID NO:43) and amino acids 75 through 118 of WNV Cp protein (SEQ ID NO:44); 4) amino acids from an internal portion of the human BID protein (GenBank accession number XP_009825 (gi: 13647251), which is incorporated herein by reference) (SEQ ID NO:45) and amino acids 84 through 95 of WNV Cp protein (SEQ ID NO:46); and 5) amino acids from an internal portion of the human Bad protein (GenBank accession number CAC22429 (gi: 12309966), which is incorporated herein by reference) (SEQ ID NO:47) and amino acids 15 through 23 of WNV Cp protein (SEQ ID NO:48). The values in brackets are identity/homology scores, where a maximum possible score is 590. Comparisons and alignments were generated by Mac Vector.

FIG. 19 shows the alignment of the HIV-1 89.6 Vpr protein sequence with portions of the sequences of proteins from other viruses and with portions of the sequences of proapoptotic proteins. The complete sequence of the HIV-1 89.6 Vpr protein (amino acids 1-96) appears at the top in bold. Shown are 7 comparisons of HIV-1 89.6 Vpr protein with other viral proteins and 6 comparisons of HIV-1 89.6 Vpr protein with proapoptotic proteins. The viral protein comparisons are as follows: 1) amino acids from an internal portion of the p230 nonstructural protein of Sindbis virus (GenBank accession number NP_062889 (gi:9790318), which is incorporated herein by reference) (SEQ ID NO:49) and amino acids 22 through 59 of H-1 89.6 Vpr protein (SEQ ID NO:50); 2) amino acids 68 through 110 of WNV Cp protein (see description for FIG. 18 above) and amino acids 54 through 95 of HIV-1 89.6 Vpr protein (SEQ ID NO:51); 3) amino acids from an internal portion of the 2A protein of Cucumber mosaic virus (GenBank accession number CAB75953 (gi:7105855), which is incorporated herein by reference) (SEQ ID NO:52) and amino acids 77 through 89 of HIV-1 89.6 Vpr protein (SEQ ID NO:53); 4) amino acids from another internal portion of the 2A protein of Cucumber mosaic virus (SEQ ID NO:54) and amino acids 49 through 67 of HIV-1 89.6 Vpr protein (SEQ ID NO:55); 5) amino acids from an internal portion of the Rubella virus capsid protein (SEQ ID NO:56) and amino acids 38 through 47 of HIV-1 89.6 Vpr protein (SEQ ID NO:57); 6) amino acids from an internal portion of the Nipah virus fusion protein (GenBank accession number NP_112026 (gi: 13559813), which is incorporated herein by reference) (SEQ ID NO:58) and amino acids 60 through 72 of HIV-1 89.6 Vpr protein (SEQ ID NO:59); and 7) amino acids from an internal portion of the reovirus core-minor form Mu2 protein (GenBank accession number AAK54467 (gi:14149150), which is incorporated herein by reference) (SEQ ID NO:60) and amino acids 60 through 72 of HIV-1 89.6 Vpr protein (SEQ ID NO:61). The proapoptotic protein comparisons are as follows: 1) amino acids from an internal portion of the mouse BIM protein (GenBank accession number NP_033884 (gi:6753192), which is incorporated herein by reference) (SEQ ID NO:62) and amino acids 7 through 74 of HIV-1 89.6 Vpr protein (SEQ ID NO:63); 2) amino acids from an internal portion of the rat BOD protein (GenBank accession number AAC23593 (gi:3228566), which is incorporated herein by reference) (SEQ ID NO:64) and amino acids 23 through 74 of HIV-1 89.6 Vpr protein (SEQ ID NO:65); 3) amino acids from an internal portion of the mouse Mtd protein (GenBank accession number AAC53582 (gi:2689660), which is incorporated herein by reference) (SEQ ID NO:66) and amino acids 16 through 67 of HIV-1 89.6 Vpr protein (SEQ ID NO:67); 4) amino acids from an internal portion of the human Bcl-2 associated X protein (SEQ ID NO:68) and amino acids 18 through 75 of HIV-189.6 Vpr protein (SEQ ID NO:69); 5) amino acids from another internal portion of the human Bcl-2 associated X protein (SEQ ID NO:70) and amino acids 18 through 42 of HIV-1 89.6 Vpr protein (SEQ ID NO:71); and 6) amino acids from an internal portion of the human Bad protein (SEQ ID NO:72) and amino acids 33 through 44 of HIV-1 89.6 Vpr protein (SEQ ID NO:73). The values in brackets are identity/homology scores, where a maximum possible score is 590. Comparisons and alignments were generated by Mac Vector.

DETAILED DESCRIPTION OF THE PREFERRED EMBODIMENTS

The present invention arises out of the discovery of the apoptosis-inducing activity of the WNV capsid (Cp) protein in tumor-derived cells. It has been discovered that expression of WNV capsid protein in cells in culture leads to the induction of an apoptotic pathway and, ultimately, to the death of hyperproliferating cells. It has also been observed that a 22 amino acid residue peptide from the carboxy-terminal region of WNV Cp protein has apoptosis-inducing activity. The apoptosis-inducing activity of WNV capsid protein renders Cp protein, and functional fragments thereof, useful in methods of killing rapidly growing cells, including cancer cells, and in screening systems to identify compounds that inhibit the apoptosis-inducing activity, which may be used for treatment of WNV infection. The virus family Flaviviridae is composed of positive-sense, single-stranded RNA genome viruses classified into three genuses: *Pestiviruses*, which include bovine diarrhea virus (BVDV), "Hepatitis C-like viruses," which include hepatitis C virus (HCV), and Flaviruses. The *Flavivirus* genus includes at least ten serologically-defined subgenus groups, as well as unclassified viruses. WNV is a member of the mosquito-borne Japanese encephalitis virus group, which also includes, among others, Japanese encephalitis virus (JEV) and St. Louis encephalitis virus (SLEV), that are highly related to WNV. Other *Flaviviruses* include Yellow fever virus (YFV) and Dengue viruses (DENV), which are in different subgenus groups. Nucleotide and amino acid sequence analyses reveal conservation of sequences within and between serogroups. The WNV Cp protein shares homology with capsid and other proteins of other viruses, including, but not limited to, viruses in the Flaviviridae family, and viruses from many other virus families. The WNV Cp protein also shares homology and with other proteins, including, non-viral proteins, including proapoptotic proteins of mammalian origin.

In some embodiments of the invention, the capsid protein is derived from a *Pestivirus*. In some embodiments of the invention, the *Pestivirus* from which the capsid protein is derived is BVDV. In some embodiments of the invention, the capsid protein is derived is from a *Flavivirus*. In some embodiments of the invention, the *Flavivirus* from which the capsid protein is derived is JEV. In some embodiments of the invention, the *Flavivirus* from which the capsid protein is derived is SLEV. In some embodiments of the invention, the *Flavivirus* from which the capsid protein is derived is YFV. In some embodiments of the invention, the *Flavivirus* from which the capsid protein is derived is DENV. In some embodiments of the invention, the *Flavivirus* from which the capsid protein is derived is WNV.

The invention provides, inter alia, methods of inducing the death of cells using capsid proteins and other proteins from viruses including *Flavivirus* or *Pestivirus*, or functional fragments thereof. In some embodiments the capsid protein, or functional fragments thereof are from WNV. The invention also provides methods of screening for compounds that inhibit the cell killing activity of capsid protein and other proteins from viruses including *Flavivirus* or *Pestivirus*, or functional fragments thereof. In some embodiments of the invention, methods are provided for screening for compounds that inhibit the cell killing activity of WNV capsid protein, or functional fragments thereof. The invention further provides pharmaceutical compositions comprising capsid proteins or other proteins from viruses including *Flaviviruses* or *Pestiviruses*, or functional fragments thereof, or nucleic acids encoding capsid proteins or other proteins from viruses including *Flaviviruses* or *Pestiviruses*, or functional fragments thereof, and methods of treating individuals having diseases characterized by hyperproliferating cells with these pharmaceutical compositions. The invention further provides vaccine compositions comprising capsid proteins or other proteins, or fragments thereof, or nucleic acids encoding capsid proteins or other proteins, or functional fragments thereof, from WNV or from other viruses including *Flaviviruses* or *Pestiviruses* and a pharmaceutically acceptable carrier. The invention also provides diagnostic methods and kits for identifying individuals exposed to WNV or other viruses including *Flaviviruses* or *Pestiviruses*.

The practice of the present invention employs, unless otherwise indicated, conventional methods of virology, immunology, microbiology, molecular biology and recombinant DNA techniques within the skill of the art. Such techniques are explained fully in the literature. See, e.g., Sambrook et al., eds., Molecular Cloning: A Laboratory Manual ($2^{nd}$ ed.) Cold Spring Harbor Laboratory Press, Cold Spring Harbor, N.Y. (1989); Ausubel et al., eds., Current Protocols in Molecular Biology, John Wiley & Sons, New York, N.Y. (2000); Glover, ed., DNA Cloning: A Practical Approach, Vols. I & II; Colowick & Kaplan, eds., Methods in Enzymology, Academic Press; Weir & Blackwell, eds., Handbook of Experimental Immunology, Vols. I-IV, Blackwell Scientific Pubs. (1986); Fields, Knipe, & Howley, eds., Fields Virology ($3^{rd}$ ed.) Vols. I & II, Lippincott Williams & Wilkins Pubs. (1996); Coligan et al., eds., Current Protocols in Immunology, John Wiley & Sons, New York, N.Y. (2000), each of which is incorporated herein by reference.

Various definitions are made throughout this document. Most words have the meaning that would be attributed to those words by one skilled in the art. Words specifically defined either below or elsewhere in this document have the meaning provided in the context of the present invention as a whole and as typically understood by those skilled in the art.

As used herein, the terms "induce" and "inducing" in reference to cell death or apoptosis refer to activities that initiate events that lead to cell death, including activities that initiate cellular events that are part of an apoptotic pathway that contribute to cell death.

As used herein, the term "apoptosis" refers to the form of eukaryotic cellular death, which is distinct form necrosis, and which includes cytoskeletal disruption, cytoplasmic shrinkage and condensation, expression of phosphatidylserine on the outer surface of the cell membrane and blebbing, resulting in the formation of cell membrane bound vesicles or apoptotic bodies. For a review of apoptotic cell death see, e.g., Utz & Anderson, 2000, Life and death decisions: regulation of apoptosis by proteolysis of signaling molecules, Cell Death Differ., 7:589-602, which is incorporated herein by reference.

As used in this specification and the appended claims, the singular forms "a," "an" and "the" include plural references unless the content clearly dictates otherwise. Thus, for example, reference to "a cell" includes a mixture of two or more cells.

As used herein, the phrases "amount effective to induce cell death" and "level effective to induce cell death" in reference to capsid protein, or functional fragments thereof, means that the amount of capsid protein, or functional fragment thereof, in contact with a cell, or the level of capsid protein, or functional fragment thereof, expressed in the cell, is effective to trigger the events that will kill the cell.

As used herein, the term "protein" refers to a polymer of amino acid residues, and is not limited to a minimum length. Polypeptides, peptides, oligopeptides, dimers, multimers, and the like, are included in the definition. Both full length proteins and fragments thereof are contemplated by the definition. The term also includes post-expression modifications to the protein, including, but not limited to, glycosylation, acetylation, phosphorylation.

As used herein, the phrase "functional fragment thereof" in reference to capsid protein, refers to fragments of less than the full length of the protein that maintain the function of the capsid protein, and are capable of inducing cell death or inducing apoptosis.

As used herein, the phrase "immunogenic fragment thereof" in reference to capsid protein, refers to fragments of less than the full length of the protein against which an immune response can be induced.

As used herein, "nucleic acid" includes DNA and RNA, as well as modified forms thereof, including modified sugars, bases, or backbone.

As used herein, the phrase "free from an entire *Flavivirus* or *Pestivirus* genome" used in reference to a nucleic acid encoding a capsid protein, or functional fragment thereof, indicates that the nucleic acid is in a form that is in a recombinant form or construct, or that it is otherwise isolated from its natural state in a *Flavivirus* or *Pestivirus* genome.

As used herein, the phrase "free from an entire WNV genome" used in reference to a nucleic acid encoding a capsid protein, or functional fragment thereof, indicates that the nucleic acid is in a form that is in a recombinant form or construct, or that it is otherwise isolated from its natural state in a WNV genome.

As used herein, "detectable level" in reference to apoptosis, means that the level or amount of apoptosis elicited is at a threshold level that can be detected or measured by techniques known to those of skill in the art Detection techniques depend on the identification of the presence or increased presence of "markers of apoptosis."

As used herein, "marker of apoptosis" refers to cellular factors or morphological changes that serve as indicators that apoptosis has been triggered and that cells are undergoing apoptotic death. "Markers of apoptosis" include, but are not limited to, exposed cellular membrane phosphatidylserine (PS), free 3'-hydroxy DNA termini, and cytoplasmic nucleosomes.

As used herein, the term "compound" in reference to inhibitors of WNV or other viruses including *Flaviviruses* or *Pestiviruses* capsid or other protein apoptosis-inducing activity includes, but is not limited to, any identifiable chemical or molecule, including, but not limited to small molecules, peptides, polypeptides, proteins, sugars, nucleotides, or nucleic acids. Such compounds can be natural or synthetic.

As used herein, "inhibit" in reference to WNV or other viruses including *Flaviviruses* or *Pestiviruses* capsid or other protein apoptosis-inducing activity, refers to any interference with this activity. For example, the term "inhibit" includes both the elimination and reduction of apoptosis-inducing activity. The inhibition of capsid protein apoptosis-inducing activity can be monitored in many ways, including, but not limited to, use of the TUNEL (TdT-mediated dUTP-X nick end labeling) assay and monitoring of PS with annexin V.

As used herein, "injectable pharmaceutical composition" refers to pharmaceutically acceptable compositions for use in patients that are sterile, pyrogen-free, and free of any particulates. See, *Remington's Pharmaceutical Sciences*, 18$^{th}$ Ed., Gennaro, ed., Mack Publishing Co., Easton, Pa., 1990 and U.S.P., the standards of the U.S. Pharmacopeia, which is incorporated herein by reference.

As used herein, "pharmaceutically acceptable carrier" includes any carrier that does not itself induce a harmful effect to the individual receiving the composition. For example, a "pharmaceutically acceptable carrier" should not induce the production of antibodies harmful to the recipient. Suitable "pharmaceutically acceptable carriers" are known to those of skill in the art and are described in *Remington's Pharmaceutical Sciences*, supra.

As used herein, "hyperproliferating cells" refers to cells that are growing, dividing, or is proliferating at an inappropriate or non-normal time or place, and includes cells that have entered the cell cycle when they should be in $G_0$ or in a quiescent state. For example, tumor cells are included within the meaning of "hyperproliferating cells." Diseases or conditions characterized by or associated with "hyperproliferating cells" include cancer, autoimmunity, non-malignant growths, and psoriasis.

As used herein, "treating" includes the amelioration and/or elimination of a disease or condition. The term "treating" is used in reference to individuals suffering from a disease or condition characterized by or associated with hyperproliferating cells and is also used in reference to individuals exposed to and/or infected with WNV or other viruses including *Flaviviruses* or *Pestiviruses*.

As used herein, the phrase "effective amount" in reference to treating an individual having a disease or condition, means a quantity sufficient to effectuate treatment and ameliorate and/or eliminate the disease or condition.

As used herein, the phrase "immunologically effective amount" in reference to vaccine compositions, means a quantity sufficient to induce a therapeutic or prophylactic immune response.

As used herein, the phrase "prophylactic immune response" in reference to treating an individual against infection from a virus, means an immune response that is prophylactic and protects from challenge with the virus.

As used herein, the phrase "therapeutic immune response" in reference to treating an individual infected with a virus, means an immune response that ameliorates and/or eliminates the viral infection.

As used herein, the phrase "therapeutically effective amount" in reference to the amount of a vaccine administered to an individual, means a quantity sufficient to induce a therapeutic immune response in the individual.

As used herein, the phrase "prophylactically effective amount" in reference to the amount of a vaccine administered to an individual, means a quantity sufficient to induce a prophylactic immune response in the individual.

As used herein, "individual" refers to human and non-human animals that can be treated with pharmaceutical compositions or vaccine compositions of the invention.

As used herein, the term "administering" includes, but is not limited to, intra-tumoral injection, transdermal, parenteral, subcutaneous, intramuscular, oral, and topical delivery.

As used herein, "intra-tumoral injection" in reference to administration of pharmaceutical compositions refers to the direct introduction of the pharmaceutical composition into a tumor site by injection.

Several aspects of the invention relate to the ability of capsid protein from WNV or other viruses including *Flaviviruses* or *Pestiviruses*, or functional fragments thereof, to inhibit cell proliferation. Several aspects of the invention also relate to the ability of other viral proteins from other viruses including *Flaviviruses* or *Pestiviruses*, or functional fragments thereof, to inhibit cell proliferation. The capsid or other protein induces cells to undergo apoptosis. In some embodiments, capsid protein from WNV or other virus including *Flaviviruses* or *Pestiviruses*, or a functional fragment thereof, and/or a nucleic acid molecule that encodes it, is used in a pharmaceutical composition to treat individuals suffering from diseases characterized by or associated with undesirable cells, particularly hyperproliferating cells such as cancer. The WNV or other virus including *Flavivirus* or *Pestivirus* capsid or other protein presents a target for the interruption of a vital viral function. Accordingly, in one aspect of the invention, anti-viral and/or anti-WNV and/or anti-*Flavivirus* or anti-*Pestivirus* compounds may be identified by identifying compounds that inhibit the apoptosis-inducing activity of WNV or other viruses including *Flaviviruses* or *Pestiviruses* capsid or other protein, or functional fragments thereof.

The present invention also relates to the use of functional fragments of WNV or other viruses including *Flaviviruses* or *Pestiviruses* capsid or other protein, and/or a nucleic acid encoding functional fragments of WNV or other viruses including *Flaviviruses* or *Pestiviruses* capsid or other protein, to induce apoptosis in cells, and to pharmaceutical compositions that comprise functional fragments of WNV or other viruses including *Flaviviruses* or *Pestiviruses* capsid or other protein, and/or a nucleic acid encoding functional fragments of WNV or other viruses including *Flaviviruses* or *Pestiviruses* capsid or other protein. As used herein, a "functional fragment" of "capsid protein from WNV or a related *Flavivirus* or *Pestivirus* "refers to a fragment of WNV or related *Flavivirus* or *Pestivirus* capsid protein which retains its ability to induce apoptosis of cells. As used herein, a "functional fragment" of "capsid or other protein from WNV or other virus including *Flavivirus* or *Pestivirus* "refers to a fragment of WNV other viruse including *Flavivirus* e or *Pestivirus* e which retains its ability to induce apoptosis of cells. Functional fragments of WNV or other virus including *Flavivirus* or *Pestivirus* capsid or other protein are at least about 10 amino acids in length, derived from WNV or other virus including *Flavivirus* or *Pestivirus* capsid or other protein, and may comprise amino acid sequences that are not derived from the capsid or other protein from WNV or other viruses including *Flavivirus* or *Pestivirus*.

Figure 10:
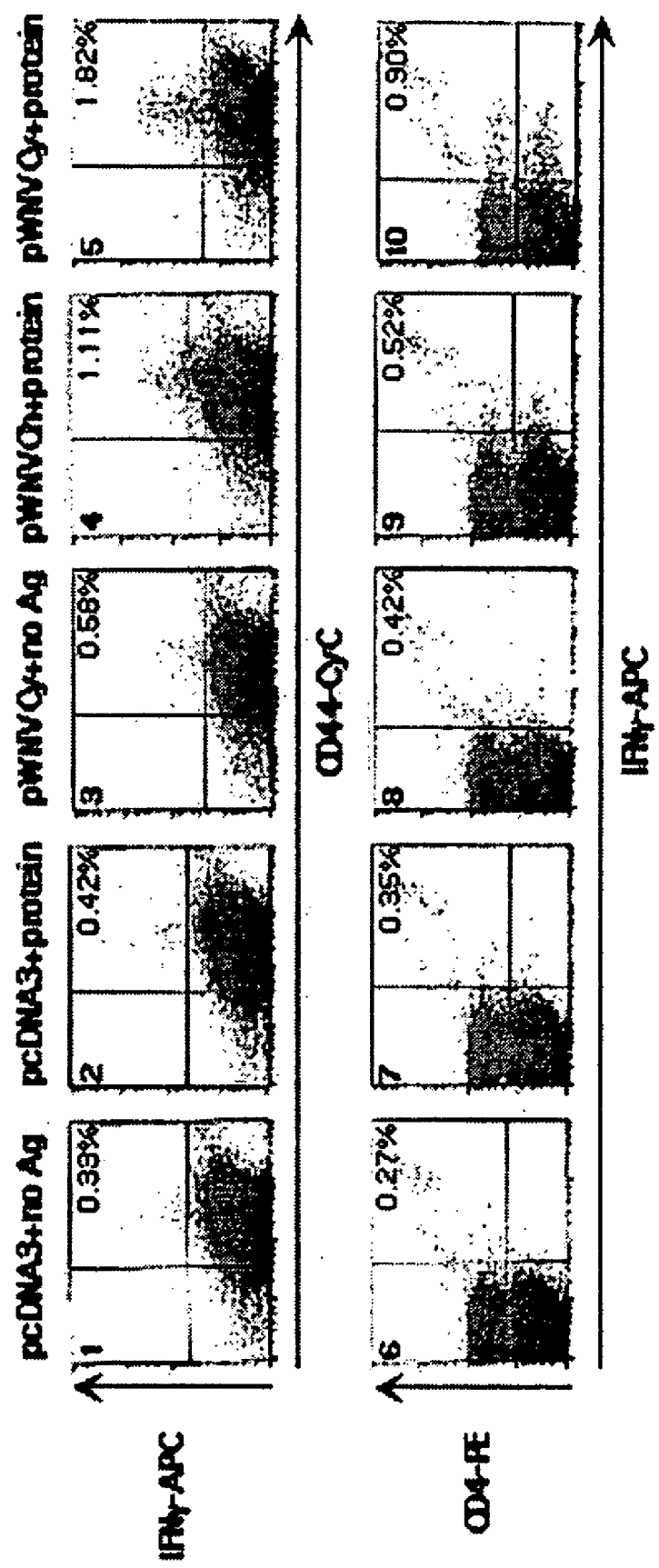
FIG. 10 presents the flow cytometry analysis of intracellular IFN-γ expression in in vitro stimulated splenocytes from DNA immunized mice. Values presented are the percentage dual positive cells. In the upper panels, the cells were stained for INF-γ and CD44; in the lower panels the cells were stained for CD4 and IFN-γ. The labeling across the top indicates the vector used to immunize the mice plus the stimulus used for the in vitro restimulation of the splenocytes. The immunizing vectors were pcDNA3 (pcDNA3.1), pWNVh-DJY (pWNVCh), and pWNVy-DJY (pWNVCy). "No Ag" indicates that the splenocytes were incubated with an in vitro translation control (described in Example 3), "protein" indicates that the splenocytes were incubated with in vitro translated Cp protein product from the pWNVy-DJY expression construct.
Figure 11:
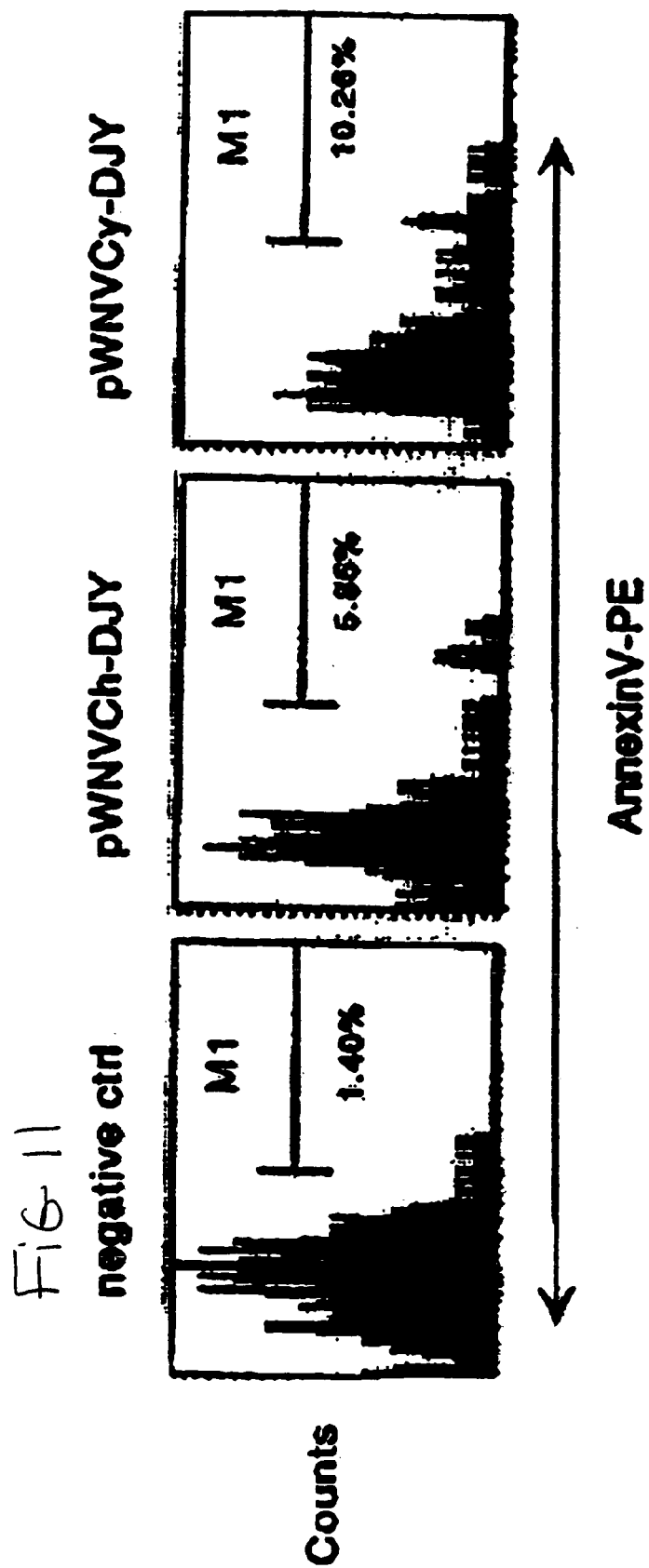
FIG. 11 depicts the results of annexin V flow cytometry analysis of HeLa cells following transfection with enhanced green fluorescent protein (EGFP) expression vector pEGFP2-N1 alone, or in combination with pWNVh-DJY or pWNVy-DJY. Values represent percentage annexin V-positive cells within the EGFP-positive (transfected cells) population.

It has also been observed that a 22 amino acid residue peptide from the carboxy-terminal region of WNV Cp protein has apoptosis-inducing activity for certain embodiments of the invention. This peptide ("WNVC-P3", also referred to herein as "Peptide 3") is shown in FIG. 10, and represents amino acid residues 90 through 110 of the WNV Cp protein. In particular, according to some embodiments of the invention, a functional fragment of WNV Cp protein includes peptide WNVC-P3, or a fragment thereof. The fragment of peptide WNVC-P3 comprises at least 3 amino acids. The fragment of peptide WNVC-P3 can be 3, 4, 5, 6, 7, 8, 9, 10, 11, 12, 13, 14, 15, 16, 17, 18, 19, 20, or 21 amino acid residues in length. Peptide WNVC-P 3 of WNV Cp protein, a fragment thereof, a fragment of Cp protein that includes peptide WNVC-P3 or fragment thereof, the Cp protein or a fusion protein, comprising Cp protein sequences and non-Cp protein sequences, can all be tested to determine whether they possess the apoptotic function of the wild type Cp protein.

Capsid protein from WNV Cp also shares homology with capsid and other proteins of other viruses, including, but not limited to, viruses in the Flaviviridae family, and viruses from many other virus families. The WNV Cp protein also shares homology and with non-viral proteins, including proapoptotic proteins of mammalian origin. Regions of homology/identity have been identified between the WNV Cp and the HIV-1 Vpr protein (which has apoptosis activity), Cp protein from Kunjin virus, Cp protein from Japanese encephalitis virus, Cp protein from Dengue virus, major capsid protein from herpes simplex virus, Ebola virus nuclear protein, Ebola virus glycoprotein, Rubella virus capsid protein, and with the following proapoptotic, non-viral proteins: human BAK protein, human Bcl-2 associated X protein, human BIK protein, human BID protein, and human Bad protein. Moreover, regions of homology/identity have been identified between HIV-1 Vpr protein and the p230 nonstructural protein of Sindbis virus, the 2A protein of cucumber mosaic virus, Rubella virus capsid protein, Nipah virus fusion protein, reovirus core-minor form Mu2 protein, and with the following the proapoptotic proteins: mouse BIM protein, rat BOD protein, mouse Mtd protein, human Bcl-2 associated X protein, and human Bad protein.

One having ordinary skill in the art can readily determine whether a protein or peptide is a functional fragment of WNV or other viruses including *Flavivirus* or *Pestivirus* capsid protein by examining its sequence and testing its ability to induce apoptosis in cells without undue experimentation. Truncated versions of WNV or other viruses including *Flavivirus* or *Pestivirus* capsid protein may be prepared and tested using routine methods and readily available starting material. As used herein, the term "functional fragment" is also meant to refer to peptides, polypeptides, and amino acid sequences linked by non-peptide bonds, or proteins which comprise an amino acid sequence that is identical to, or substantially homologous to at least a portion of the WNV or other viruses including *Flavivirus* or *Pestivirus* capsid protein amino acid sequence, and which are capable of inducing apoptosis. The term "substantially homologous" refers to an amino acid sequence that has conservative substitutions. One having ordinary skill in the art can produce functional fragments of WNV or other viruses including *Flavivirus* or *Pestivirus* capsid protein following the disclosure provided herein and well known techniques. The functional fragments thus identified may be used and formulated in place of full length WNV or other viruses including *Flavivirus* or *Pestivirus* capsid protein without undue experimentation.

The present invention also relates to vaccines comprising immunogenic fragments of WNV or other viruses including *Flavivirus* or *Pestivirus* capsid protein, and/or a nucleic acid encoding immunogenic fragments of WNV or other viruses including *Flavivirus* or *Pestivirus* capsid protein, to induce prophylactic or therapeutic immune responses in individuals. As used herein, an "immunogenic fragment" of "capsid protein from WNV or a other viruses including *Flavivirus* or *Pestivirus* " refers to a fragment of WNV or other viruses including *Flavivirus* or *Pestivirus* capsid protein which is capable of inducing an immune response. Immunogenic fragments of WNV or other viruses including *Flavivirus* or *Pestivirus* capsid protein are at least about 10 amino acids in length, derived from WNV or other viruses including *Flavivirus* or *Pestivirus* capsid protein, and may comprise amino acid sequences that are not derived from WNV or other viruses including *Flavivirus* or *Pestivirus* capsid protein. One having ordinary skill in the art can readily determine whether a protein or peptide is an immunogenic fragment of WNV or other viruses including *Flavivirus* or *Pestivirus* capsid protein by the use of classical immunological assays to screen for antibody production in response to immunizations with fragments of WNV or other viruses including *Flavivirus* or *Pestivirus* capsid protein. These include, for example, 1) enzyme-linked immunosorbent assay (ELISA), 2) proliferation assays of cells from lymphoid organs, and 3) evaluation of the number of cells producing antibodies to a given antigen. Detailed protocols for these standard assays can be found in such manuals on immunology as Weir & Blackwell, eds., Handbook of Experimental Immunology, supra and Coligan et al., eds., Current Protocols in Immunology, supra. One having ordinary skill in the art can produce and identify immunogenic fragments of WNV or other viruses including *Flavivirus* or *Pestivirus* capsid protein following the disclosure provided herein and well known techniques. The immunogenic fragments thus identified may be used and formulated in place of full length WNV or other viruses including *Flavivirus* or *Pestivirus* capsid protein without undue experimentation.

Therapeutic aspects of the invention include use of WNV or other viruses including *Flavivirus* or *Pestivirus* capsid protein, a functional fragment of WNV or other viruses including *Flavivirus* or *Pestivirus* capsid protein, nucleic acid molecules encoding WNV or other viruses including *Flavivirus* or *Pestivirus* capsid protein, or nucleic acid molecules encoding a functional fragment of WNV or other viruses including *Flavivirus* or *Pestivirus* capsid protein in pharmaceutical compositions useful to treat an individual suffering from diseases characterized by or associated with hyperproliferating cells, such as cancer or psoriasis.

One aspect of the present invention is to use WNV or other viruses including *Flavivirus* or *Pestivirus* capsid protein, or a functional fragment thereof, or nucleic acid molecules encoding WNV or other viruses including *Flavivirus* or *Pestivirus* capsid protein, or a functional fragment thereof, in a pharmaceutical composition to combat diseases that are characterized by undesirable cells such as, but not limited to, those diseases characterized by the hyperproliferation of cells, such as cancer or psoriasis. According to the invention, pharmaceutical compositions are provided which comprise either WNV or other viruses including *Flavivirus* or *Pestivirus* capsid protein, or a functional fragment thereof, or a nucleic acid molecule which comprises a DNA or RNA sequence that encodes WNV or other viruses including *Flavivirus* or *Pestivirus* capsid protein, or a functional fragment thereof.

Another aspect of the present invention relates to pharmaceutical compositions that comprise WNV or other viruses including *Flavivirus* or *Pestivirus* capsid protein, or a functional fragment thereof, and/or a nucleic acid molecule encoding WNV or other viruses including *Flavivirus* or *Pestivirus* capsid protein, or a functional fragment thereof, and a pharmaceutically acceptable carrier or diluent. Pharmaceutical compositions comprising WNV or other viruses including *Flavivirus* or *Pestivirus* capsid protein, or a functional fragment thereof, and/or a nucleic acid molecule encoding WNV or other viruses including *Flavivirus* or *Pestivirus* capsid protein, or a functional fragment thereof, are useful for treating an individual having a pathology or condition characterized by hyperproliferating cells. As described herein, pharmaceutical compositions useful for treating diseases characterized by undesirable cells such as hyperproliferating cells may include WNV or other viruses including *Flavivirus* or *Pestivirus* capsid protein, or a functional fragment thereof, and/or a nucleic acid molecule encoding *Flavivirus* or *Pestivirus* capsid protein, or a functional fragment thereof, since WNV or other viruses including *Flavivirus* or *Pestivirus* capsid protein, or a functional fragment thereof, are by definition, agents which induce apoptotic death in cells. Pharmaceutical compositions of the present invention are particularly useful for treating cancer characterized by solid tumors. The ability to stimulate hyperproliferating cells to undergo apoptotic death provides a means to disrupt the hyperproliferation of the cells, thereby decreasing the tumor. In diseases such as cancer and psoriasis which are characterized by the inappropriate hyperproliferation of cells, the pharmaceutical composition is useful to arrest the hyperproliferation through an induction of an apoptotic cell death, thereby effectuating a treatment of the disease.

Accordingly, another aspect of the present invention is a method of treating an individual suffering from a disease associated with hyperproliferating cells, which comprises the step of administering to said individual an amount of WNV or other viruses including *Flavivirus* or *Pestivirus* capsid protein, or functional fragment thereof, and/or a nucleic acid molecule encoding WNV or other viruses including *Flavivirus* or *Pestivirus* capsid protein, or a functional fragment thereof, sufficient to induce the apoptosis of said cells.

Another aspect of the present invention is a method of treating an individual suffering from a disease associated by undesirable cells such as autoimmune diseases, which comprises the step of administering to said individual an amount of WNV or other viruses including *Flavivirus* or *Pestivirus* capsid protein, or functional fragment thereof, and/or a nucleic acid molecule encoding WNV or other viruses including *Flavivirus* or *Pestivirus* capsid protein, or a functional fragment thereof, sufficient to induce the apoptosis of said cells.

Another aspect of the present invention relates to vaccine compositions that comprise WNV or other viruses including *Flavivirus* or *Pestivirus* capsid protein, or an immunogenic fragment thereof, and/or a nucleic acid molecule encoding WNV or other viruses including *Flavivirus* or *Pestivirus* capsid protein, or an immunogenic fragment thereof, and a pharmaceutically acceptable carrier or diluent Vaccine compositions comprising capsid protein from WNV or a other viruses including *Flavivirus* or *Pestivirus*, or an immunogenic fragment thereof, are useful for immunizing an individual against WNV or a other viruses including *Flavivirus* or *Pestivirus*. The immunity may be prophylactic (to prevent infection) or therapeutic (to treat infection). Where the immunity is prophylactic, the individual is protected against challenge with the virus. Where the immunity is therapeutic, the individual's current viral infection is treated.

Accordingly, an aspect of the present invention is a method of treating an individual suffering from WNV or a other viruses including *Flavivirus* or *Pestivirus* infection, which comprises the step of administering to said individual an amount of capsid protein, or an immunogenic fragment thereof, from WNV or a other viruses including *Flavivirus* or *Pestivirus*, sufficient to stimulate a therapeutic immune response.

Another aspect of the present invention is a method of preventing WNV or a other viruses including *Flavivirus* or *Pestivirus* infection in an individual, which comprises the step of administering to said individual an amount of capsid protein, or an immunogenic fragment thereof, from WNV or a other viruses including *Flavivirus* or *Pestivirus*, sufficient to stimulate a prophylactic immune response.

When capsid protein, or an immunogenic fragment thereof, from WNV or other viruses including *Flavivirus* or *Pestivirus*, is delivered to an individual as a component in a vaccine (either directly as protein or by subsequent expression from a nucleic acid delivered in the vaccine), the capsid protein, or immunogenic fragment thereof, becomes a target against which the individual develops an immune response, protecting from infection (prophylactic), or treating an infection (therapeutic). Those of skill in the art will recognize that the immune response can be both therapeutic and prophylactic, in that following a therapeutic treatment, the individual may be protected from further challenge with the virus.

Capsid Protein

WNV capsid protein, or functional fragments thereof, may be produced by routine means using readily available starting materials as described above. The nucleic acid sequence encoding WNV capsid protein as well as the amino acid sequence of the protein are well known. The entire genome for a number of WNV isolates are published and available in GenBank, including isolate 2741 (accession number AF206518), strain NY99-flamingo382-99 (accession number AF196835), the complete polyprotein gene of strain HNY1999 (accession number AF202541) and the isolate identified as accession number M12294, each of which is incorporated herein by reference. There are a variety of publications relating to sequence information for the WNV genome, citations of which are linked to the sequence information in GenBank. Each of these references, including the publicly available sequence information, is incorporated herein by reference.

Sequence information for capsid proteins and nucleic acids from other *Flaviviruses* or *Pestiviruses* can also be found in GenBank. By way of non-limiting examples, complete genome sequences of strains and isolates provided in GenBank include, JEV (accession number M18370, D90194, and D90195), SLEV (accession number M16614), YFV (accession numbers AF094612, U17067, U17066, U54798, U21055, U21056, and X03700), DENV (accession numbers M23027, U88535, U88536, and U88537), and BVDV (accession number M31182), each of which is incorporated herein by reference.

Provision of a suitable DNA sequence encoding a desired protein permits the production of the protein using recombinant techniques now known in the art. The coding sequence can be obtained by, for example, cloning it from infected cells, using PCR primers designed based upon the publicly available sequence information. The DNA sequence may also be prepared chemically using a DNA synthesizer. When the coding DNA is prepared synthetically, advantage can be taken of known codon preferences of the intended host where the DNA is to be expressed. Additionally, changes may be introduced into the coding sequence, such as point mutations, insertions, or deletions, to create controls and other modified forms of the capsid protein.

One having ordinary skill in the art can, using well known techniques, obtain a DNA molecule encoding the WNV capsid protein or a other viruses including *Flavivirus* or *Pestivirus* capsid protein and insert that DNA molecule into a commercially available expression vector for use in well known expression systems. For example, the commercially available plasmid pSE420 (Invitrogen, San Diego, Calif.) may be used for capsid protein production in *E. coli* bacteria cells. The commercially available plasmid pYES2 (Invitrogen, San Diego, Calif.) may be used for production in yeast cells, such as *S. cerevisiae*. The commercially available MaxBac 2.0 Kit (Invitrogen, San Diego, Calif.), with the pBlueBac4 vector, is a complete baculovirus expression system that may be used for the production of capsid protein in insect cells, such as Sf9 cells. The commercially available plasmid pcDNA I (nitrogen, San Diego, Calif.) may be used for the production of capsid protein in mammalian cells, such as Chinese hamster ovary cells.

One having ordinary skill in the art can use these commercial expression vectors systems or others to produce WNV and other viruses including *Flavivirus* or *Pestivirus* capsid proteins using routine techniques and readily available starting materials.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See, e.g., Ausubel et al., eds., Current Protocols in Molecular Biology, supra. Thus, the desired proteins can be prepared in both prokaryotic and eukaryotic systems, resulting in a spectrum of processed forms of the protein.

The most commonly used prokaryotic system remains *E. coli*, although other systems such as *Bacillus subtilis* and *Pseudomonas* are also useful. Suitable control sequences for prokaryotic systems include both constitutive and inducible promoters including, but not limited to, the lac promoter, the trp promoter, hybrid promoters such as the tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but are not limited to, yeast cells, fungal cells, insect cells, mammalian cells, avian cells, and cells of higher plants. Suitable promoters are available which are compatible and operable for use in each of these host cell types. Also available, are termination sequences and enhancers, such as, for example, the baculovirus polyhedron promoter. As described above, promoters can be either constitutive or inducible. For example, in mammalian systems, the mouse metallothionine promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art One having ordinary skill in the art can, using well known techniques, isolate the WNV or other viruses including *Flavivirus* or *Pestivirus* capsid protein produced using such expression systems.

In addition to producing these proteins by recombinant techniques, automated amino acid synthesizers may also be employed to produce WNV or other viruses including *Flavivirus* or *Pestivirus* capsid protein, or functional fragments thereof. It should be further noted that if the proteins herein are made synthetically, substitution by amino acids which are not encoded by the gene may also be made. Alternative residues include, for example, the amino acids of the formula $H_2N(CH_2)_nCOOH$ wherein n is 2-6. These are neutral, nonpolar amino acids, as are sarcosine (Sar), t-butylalanine (t-BuAla), t-butylglycine (t-BuGly), N-methyl isoleucine (N-MeIle), and norleucine (Nleu). Phenylglycine, for example, can be substituted for Trp, Tyr or Phe, an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

Portions of this disclosure relate to pharmaceutical compositions and other portions of the disclosure relate to therapeutic or prophylactic vaccines. The pharmaceutical compositions of the invention are intended to be administered to an individual for the purpose of killing cells and the vaccine compositions of the invention are intended to be administered to an individual for the purpose of inducing a prophylactic or therapeutic immune response against virus infection. The pharmaceutical compositions of the invention are administered in an amount effective for inducing apoptosis and killing cells. The vaccine compositions of the invention are administered in an amount effective for the purpose of inducing an immune response.

Whether the compositions are being prepared as pharmaceuticals or vaccines, many aspects of the composition, formulation, dosing, and administration of the pharmaceutical compositions and vaccine compositions of the invention are related, and can be identical, as will be readily appreciated by those of skill in the art For example, both pharmaceutical compositions and vaccines of the invention may comprise WNV or other viruses including *Flavivirus* or *Pestivirus* capsid protein, or a fragment thereof. The capsid protein, or fragment thereof, in the pharmaceutical composition will be functional in apoptosis activity, whereas, the capsid protein, or fragment thereof, in the vaccine will be immunogenic. Portions of the disclosure concerning related aspects are considered to be relevant to both pharmaceutical compositions and to vaccines.

Pharmaceutical compositions used for treating diseases characterized by hyperproliferating cells comprising a WNV or other viruses including *Flavivirus* or *Pestivirus* capsid protein, or functional fragment thereof, and a pharmaceutically acceptable carrier or diluent may be formulated by one of skill in the art with compositions selected depending upon the chosen mode of administration. Suitable pharmaceutical carriers are described in *Remington's Pharmaceutical Sciences*, supra., a standard reference text in this field.

A common requirement for any route of administration is efficient and easy delivery. In one embodiment of the invention, the pharmaceutical compositions are administered by injection. In a preferred embodiment, the compositions are administered by intra-tumoral injection. Other means of administration include, but are not limited to, transdermal, transcutaneous, subcutaneous, intraperitoneal, mucosal, or general persistent administration.

For parenteral administration, the WNV or other viruses including *Flavivirus* or *Pestivirus* capsid protein, or functional fragment thereof, can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

Although individual needs may vary, the determination of optimal ranges for effective amounts of formulations is within the skill of the art. Human doses can also readily be extrapolated from animal studies (Katocs et al., Chapter 27 In: *Remington's Pharmaceutical Sciences*, $18^{th}$ Ed., Gennaro, ed., Mack Publishing Co., Easton, Pa., 1990, which is incorporated herein by reference). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3 In: *Goodman & Gilman's The Pharmacological Basis of Therapeutics*, $9^{th}$ Ed., Hardman et al., eds., McGraw-Hill, New York, N.Y., 1996, which is incorporated herein by reference). Usually, a daily dosage of WNV or other viruses including *Flavivirus* or *Pestivirus* capsid protein, or functional fragment thereof, can be about 1 µg to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

The pharmaceutical compositions according to the present invention may be administered as a single doses or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions comprising WNV or other viruses including *Flavivirus* or *Pestivirus* capsid protein, or functional fragments or derivatives thereof, may be administered by any means that enables the active agent to reach the agent's site of action in the body of the recipient. Because proteins are subject to digestion when administered orally, parenteral administration, i.e., intravenous, subcutaneous, intramuscular, would ordinarily be used to optimize absorption. In addition, the pharmaceutical compositions of the present invention may be injected at a site at or near hyperproliferative growth. For example, administration may be by direct injection into a solid tumor mass or in the tissue directly adjacent thereto. If the individual to be treated is suffering from psoriasis, the WNV or other viruses including *Flavivirus* or *Pestivirus* capsid protein, or functional fragment thereof, may be formulated with a pharmaceutically acceptable topical carrier and the formulation may be administered topically as a creme, lotion or ointment for example.

Vaccine compositions, used for prophylactic or therapeutic treatment against WNV or other viruses including *Flavivirus* or *Pestivirus* infection in an individual, comprising a WNV or other viruses including *Flavivirus* or *Pestivirus* capsid protein, or functional fragment thereof, and a pharmaceutically acceptable carrier or diluent, may be formulated by one of skill in the art with compositions selected depending upon the chosen mode of administration. Suitable pharmaceutical carriers for vaccines are described in *Remington's Pharmaceutical Sciences*, supra., a standard reference text in this field, and can include any carrier that does not itself induce the production of antibodies harmful to the individual receiving the composition. Suitable carriers include large, slowly metabolized macromolecules, such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. Additionally, these carriers may function as immunostimulating agents ("adjuvants"). Furthermore, the antigen may be conjugated to a bacterial toxoid, such as a toxoid from diphtheria or tetanus.

Adjuvants that can be used with the vaccine compositions of the invention include, but are not limited to, (1) aluminum salts (alum), such as aluminum hydroxide, aluminum phosphate, aluminum sulfate, etc.; (2) oil-in-water emulsion formulations, such as for example, (a) Synthetic Adjuvant Formulation (SAF), available from Chiron (Emeryville, Calif.), and (b) Ribi Adjuvant System (RAS), (Corixa, Seattle, Wash.) containing detoxified endotoxin and mycobacterial cell wall components in 2% squalene; (3) water-in-oil formulations such as TiterMax, available from CytRx (Norcross, Ga.); (4) saponin adjuvants, such as Stimulon (Cambridge Bioscience, Worcester, Mass.) may be used or particles generated therefrom such as ISCOMS (immune-stimulating complexes); (4) Freund's Complete Adjuvant (FCA) and Freund's Incomplete Adjuvant (FIA); (5) cytokines, such as interleukins (IL-1, IL-2, etc.), macrophage colony stimulating factor (M-CSF), and tumor necrosis factor (INF), etc; and (6) other substances that act as immunostimulating agents to enhance the immunological effectiveness of the vaccine composition.

Vaccine compositions of the invention typically will contain diluents, such as water, saline, glycerol, ethanol, etc.

Additionally, auxiliary substances, such as wetting or emulsifying agents, pH-buffering substances, and the like, may be present in such vehicles.

Vaccine compositions of the invention typically are prepared as injectables, either as liquid solutions or suspensions. Solid formulations, suitable for dissolving in, or suspending in, liquid vehicles prior to injection, may also be prepared. The preparation also may be emulsified or encapsulated in liposomes for enhanced adjuvant effect, as discussed above under pharmaceutically acceptable carriers.

The vaccine compositions of the present invention comprise an immunologically effective amount of WNV or other viruses including *Flavivirus* or *Pestivirus* capsid protein, or functional fragments or derivatives thereof, and may be administered by any means that enables the recipient's immune system to generate a prophylactic or therapeutic immune response. The immunologically effective amount of WNV or other viruses including *Flavivirus* or *Pestivirus* capsid protein, or functional fragments or derivatives thereof, is the quantity administered to an individual, either in a single dose or as part of a series, that is effective for therapeutic or prophylactic treatment of the individual. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating physician's assessment of the medical situation, and other relevant factors. It is expected that the amount will fall in a relatively broad range that can be determined through routine trials.

A common requirement for any route of administration is efficient and easy delivery. In one embodiment of the invention, the vaccine compositions are administered parenterally, e.g., by injection, either subcutaneous or intramuscular injection. Other means of administration include, but are not limited to, transdermal, transcutaneous, intraperitoneal, mucosal, or general persistent administration. Dosage treatment may be a single dose schedule or a multiple dose schedule. The vaccine may be administered in conjunction with other immunoregulatory agents and/or in conjunction with other vaccines.

Nucleic Acid

Another aspect of the present invention relates to pharmaceutical compositions that comprise a nucleic acid molecule that encodes WNV or other viruses including *Flavivirus* or *Pestivirus* capsid protein, or a functional fragment thereof, and a pharmaceutically acceptable carrier or diluent. According to the present invention, genetic material that encodes WNV or other viruses including *Flavivirus* or *Pestivirus* capsid protein, or a functional fragment thereof, is delivered to an individual in an expressible form. The genetic material, DNA or RNA, is taken up by the cells of the individual and expressed. The WNV or other viruses including *Flavivirus* or *Pestivirus* capsid protein, or functional fragment thereof, that is thereby produced can induce the apoptotic death of the hyperproliferating cells. Thus, pharmaceutical compositions comprising genetic material that encodes WNV or other viruses including *Flavivirus* or *Pestivirus* capsid protein, or functional fragment thereof, are useful in the same manner as pharmaceutical compositions comprising WNV or other viruses including *Flavivirus* or *Pestivirus* capsid protein, or functional fragments thereof: for treating an individual having a pathology or condition characterized by or associated with hyperproliferating cells.

Pharmaceutical compositions of the present invention are particularly useful for treating cancer characterized by solid tumors.

Thus, a further aspect of the present invention relates to a method of treating an individual suffering from a disease associated with hyperproliferating cells which comprises the step of administering to said individual an amount of nucleic acid that comprises a nucleotide sequence that encodes WNV or other viruses including *Flavivirus* or *Pestivirus* capsid protein, or a functional fragment thereof, operably linked to regulatory elements necessary for expression.

Another aspect of the present invention relates to vaccine compositions that comprise a nucleic acid molecule that encodes capsid protein, or immunogenic fragment thereof, from WNV or a other viruses including *Flavivirus* or *Pestivirus*, and a pharmaceutically acceptable carrier or diluent. According to the present invention, genetic material that encodes capsid protein, or an immunogenic fragment thereof, is delivered to an individual in an expressible form. The genetic material, DNA or RNA, is taken up by the cells of the individual and expressed. The capsid protein, or immunogenic fragment thereof, that is thereby produced serves to induce an immune response in the individual. Thus, vaccine compositions comprising genetic material that encodes capsid protein, or an immunogenic fragment thereof, from WNV or other viruses including *Flavivirus* or *Pestivirus*, are useful in the same manner as vaccine compositions comprising capsid protein: for immunizing individuals. The immunity can be prophylactic if the individual is uninfected and therapeutic if the individual is infected. Accordingly, further aspects of the present invention relate to a method of preventing infection or treating infected individuals.

Nucleotide sequences that encode WNV or other viruses including *Flavivirus* or *Pestivirus* capsid protein, or a functional fragment thereof, operably linked to regulatory elements necessary for expression in the individual's cell, may be delivered as pharmaceutical compositions using gene therapy strategies which include, but are not limited to, either viral vectors such as adenovirus or retrovirus vectors or direct nucleic acid transfer. Methods of delivery of nucleic acids encoding proteins of interest, using viral vectors are widely reported. A recombinant viral vector such as a retroviral vector, adenovirus or adeno-associated viral vector is prepared using routine methods and starting materials. The recombinant viral vector comprises a nucleotide sequence that encodes WNV or other viruses including *Flavivirus* or *Pestivirus* capsid protein, or a functional fragment thereof. Such a vector is combined with a pharmaceutically acceptable carrier or diluent. The resulting pharmaceutical preparation may be administered to an individual. Once an individual is infected with the viral vector, WNV or other viruses including *Flavivirus* or *Pestivirus* capsid protein, or a functional fragment thereof, is produced in the infected cells.

Nucleotide sequences that encode WNV or other viruses including *Flavivirus* or *Pestivirus* capsid protein, or immunogenic fragments thereof, operably linked to regulatory elements necessary for expression in the individual's cell, may be delivered as vaccine compositions comprising viral vectors, such as adenovirus, adeno-associated virus, vaccinia virus or retrovirus vectors, or bacterial or mycobacterial vectors. Furthermore, the nucleotide sequences can be incorporated within live and/or attenuated vaccines.

Alternatively, a molecule which comprises a nucleotide sequence that encodes WNV or other viruses including *Flavivirus* or *Pestivirus* capsid protein, or a functional or immunogenic fragment thereof, can be administered as a pharmaceutical composition or vaccine by direct nucleic acid transfer, without the use of infectious vectors. The nucleic acid molecule may be DNA or RNA, preferably DNA. The DNA molecule may be linear or circular; it is preferably a plasmid. The nucleic acid molecule is combined with a pharmaceutically acceptable carrier or diluent.

As described above, many aspects of the composition, formulation, dosing, and administration of the pharmaceutical compositions and vaccines of the invention are related, and can be identical. For example, both pharmaceutical compositions and vaccines of the invention may comprise a nucleic acid encoding WNV or other viruses including *Flavivirus* or *Pestivirus* capsid protein, or fragment thereof. The encoded capsid protein, or fragment thereof, in the pharmaceutical composition will be functional in apoptosis activity, whereas, the encoded capsid protein, or fragment thereof, in the vaccine will be immunogenic. Portions of the disclosure concerning related aspects are considered to be relevant to both pharmaceutical compositions and to vaccines.

Importantly, in pharmaceutical compositions, the amount of nucleic acid must be sufficient so that it will be sufficiently expressed to induce cell death. If the nucleic acid encodes a fragment, the fragment must be a functional fragment. The immunogenicity is not a relevant feature in the pharmaceutical composition. In the vaccine compositions, on the other hand, the immunogenicity is critical. The primary activity of vaccines is in the induction of a prophylactic or therapeutic immune response. If a fragment is encoded by the nucleic acid it must be an immunogenic fragment.

According to the invention, the pharmaceutical composition or vaccine comprising a nucleic acid sequence that encodes WNV or a other viruses including *Flavivirus* or *Pestivirus* capsid protein, or a functional fragment thereof, may be administered directly into the individual. The genetic material is introduced into cells which are present in the body of the individual. Preferred routes of administration include intramuscular, intraperitoneal, intradermal and subcutaneous injection. Alternatively, the pharmaceutical composition may be introduced by various means into cells that are removed from the individual. Such means include, for example, transfection, electroporation and microprojectile bombardment. After the nucleic acid molecule is taken up by the cells, they are reimplanted into the individual. It is contemplated that otherwise non-immunogenic cells that have genetic constructs incorporated therein can be implanted into the individual even if the vaccinated cells were originally taken from another individual.

Genetic constructs may be administered by means including, but not limited to, traditional syringes, needleless injection devices, or "microprojectile bombardment gene guns." According to some embodiments of the present invention, the genetic construct is administered to an individual using a needleless injection device. According to some embodiments of the present invention, the genetic construct is simultaneously administered to an individual intradermally, subcutaneously and intramuscularly using a needleless injection device. Needleless injection devices are well known and widely available. One having ordinary skill in the art can, following the teachings herein, use needleless injection devices to deliver genetic material to cells of an individual. Needleless injection devices are well suited to deliver genetic material to all tissue. They are particularly useful to deliver genetic material to skin and muscle cells. In some embodiments, a needleless injection device may be used to propel a liquid that contains DNA molecules toward the surface of the individual's skin. The liquid is propelled at a sufficient velocity such that upon impact with the skin the liquid penetrates the surface of the skin, permeates the skin and muscle tissue therebeneath. Thus, the genetic material is simultaneously administered intradermally, subcutaneously and intramuscularly. In some embodiments, a needleless injection device may be used to deliver genetic material to tissue of other organs in order to introduce a nucleic acid molecule to cells of that organ.

According to the invention, the genetic vaccine may be administered directly into the individual to be immunized or ex vivo into removed cells of the individual which are reimplanted after administration. By either route, the genetic material is introduced into cells which are present in the body of the individual. Routes of administration include, but are not limited to, intramuscular, intraperitoneal, intradermal, subcutaneous, intravenous, intraarterially, intraoccularly and oral as well as transdermally or by inhalation or suppository. Preferred routes of administration include intramuscular, intraperitoneal, intradermal and subcutaneous injection.

The pharmaceutical or vaccine compositions according to the present invention comprise about 1 nanogram to about 2000 micrograms of DNA. In some preferred embodiments, pharmaceutical or vaccine compositions according to the present invention comprise about 5 nanogram to about 1000 micrograms of DNA. In some preferred embodiments, the pharmaceutical or vaccine compositions contain about 10 nanograms to about 800 micrograms of DNA. In some preferred embodiments, the pharmaceutical or vaccine compositions contain about 0.1 to about 500 micrograms of DNA. In some preferred embodiments, the pharmaceutical or vaccine compositions contain about 1 to about 350 micrograms of DNA. In some preferred embodiments, the pharmaceutical or vaccine compositions contain about 25 to about 250 micrograms of DNA. In some preferred embodiments, the pharmaceutical or vaccine compositions contain about 100 to about 200 micrograms DNA.

The pharmaceutical or vaccine compositions according to the present invention are formulated according to the mode of administration to be used. In cases where pharmaceutical or vaccine compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

In some embodiments, nucleic acid molecules are delivered to the cells in conjunction with administration of a polynucleotide function enhancer or a "genetic vaccine facilitator" (GVF) agent Polynucleotide function enhancers are described in U.S. Pat. Nos. 5,593,972, 5,981,505, and International Application Serial Number PCT/US94/00899, filed Jan. 26, 1994, which are each incorporated herein by reference. GVF agents are described in U.S. Pat. Nos. 5,739,118, 5,837,533, and International Application Serial Number PCT/US99/04332, international filing date Feb. 26, 1999, each of which is incorporated herein by reference.

The co-agents, which are administered in conjunction with nucleic acid molecules, may be administered as a mixture with the nucleic acid molecule, or may be administered separately, simultaneously, before, or after administration of the nucleic acid molecules. In addition, other agents which may function as transfecting agents and/or replicating agents and/or inflammatory agents, and which may be co-administered with or without a GVF, include growth factors, cytokines, and lymphokines, such as α-interferon, γ-interferon, platelet derived growth factor (PDGF), tumor necrosis factor (TNF), epidermal growth factor (EGF), interleukin-1 (IL-1), IL-2, IL-4, IL-6, IL-8, IL-10, and IL-12, as well as fibroblast growth factor, surface active agents, such as immune-stimulating complexes (ISCOMS), Freund's incomplete adjuvant, lipopolysaccharide (LPS) analogs, including monophosphoryl Lipid A (MPL), muramyl peptides, quinone analogs, vesicles, squalene, and squalene and hyaluronic acid. In some embodiments, an immunomodulating protein may be used as a GVF.

Nucleic acid molecules which are delivered to cells according to the invention may serve as genetic templates for proteins that function as prophylactic and/or therapeutic immunizing agents. In preferred embodiments, the nucleic acid the nucleic acid molecules comprise the necessary regulatory sequences for transcription and translation of the coding region in the cells of the animal.

The present invention relates to improved attenuated live vaccines and improved vaccines which use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, each of which is incorporated herein by reference. Gene constructs are provided which include the nucleotide sequence that encodes the capsid protein is operably linked to regulatory sequences that can function in the vaccines to effect expression. The gene constructs are incorporated in the attenuated live vaccines and recombinant vaccines to produce vaccines according to the invention.

The pharmaceutical and vaccine compositions according to this aspect of the present invention comprise about 0.1 µg to about 1000 µg of DNA. In some preferred embodiments, the pharmaceutical and vaccine compositions contain about 1 µg to about 500 µg of DNA. In some preferred embodiments, the pharmaceutical and vaccine compositions contain about 25 µg to about 250 µg of DNA. Most preferably, the pharmaceutical and vaccine compositions contain about 100 µg DNA.

The pharmaceutical and vaccine compositions according to this aspect of the present invention are formulated according to the mode of administration to be used, as discussed above. One having ordinary skill in the art can readily formulate a nucleic acid molecule that encodes WNV or other viruses including *Flavivirus* or *Pestivirus* capsid protein, or a functional fragment thereof. In cases where intramuscular injection is the chosen mode of administration, an isotonic formulation is used. Generally, additives for isotonicity can include sodium chloride, dextrose, mannitol, sorbitol and lactose. Isotonic solutions such as phosphate buffered saline may be used. Stabilizers include gelatin and albumin. In vaccine compositions, the addition of adjuvants or immunostimulating agents may be desirable.

Apoptosis Assay

Another aspect of the present invention relates to a method of identifying compounds which inhibit the WNV Cp or capsid or other protein of other viruses including *Flavivirus* or *Pestivirus*, or a functional fragment thereof, from inducing cells to undergo apoptosis which comprises the steps of first contacting, in the presence of a test compound, said cells with an amount of WNV or other viruses including *Flavivirus* or *Pestivirus* capsid or other protein, or a functional fragment thereof, sufficient to induce a detectable level of apoptosis, and then observing said cells to determine if apoptosis occurs in the presence of the test compound. Compounds which interfere with the apoptosis-inducing activity of WNV or other viruses including *Flavivirus* or *Pestivirus* capsid or other protein, or functional fragments thereof, may be useful as drugs for combating the virus and treating WNV and other virus infections including *Flavivirus* or *Pestivirus* infections.

According to this aspect of the invention, compounds are identified which inhibit the ability of WNV or other viruses including *Flavivirus* or *Pestivirus* capsid protein, or functional fragments thereof, to induce apoptosis in hyperproliferating cells. An assay is provided which compares apoptosis induction by WNV or other viruses including *Flavivirus* or *Pestivirus* capsid protein, or functional fragment thereof, in the presence or absence of test compounds. Using this assay, compounds can be identified that inhibit the apoptosis-inducing activity of WNV or other viruses including *Flavivirus* or *Pestivirus* capsid protein, or functional fragments thereof. Such compounds may be useful as anti-WNV and/or anti-*Flavivirus* or anti-*Pestivirus* therapeutics.

The method of the present invention comprises the step of contacting cells with WNV or other viruses including *Flavivirus* or *Pestivirus* capsid protein, or functional fragment thereof, in the presence of a test compound. The cells can then be observed to determine if the WNV or other viruses including *Flavivirus* or *Pestivirus* capsid protein, or functional fragment thereof, induces apoptosis. A control may be provided in which cells are contacted with WNV or other viruses including *Flavivirus* or *Pestivirus* capsid protein, or functional fragment thereof, in the absence of test compound. A further control may be provided in which the test compound is contacted with cells in the absence of WNV or other viruses including *Flavivirus* or *Pestivirus* capsid protein, or functional fragment thereof. If the cells contacted with WNV or other viruses including *Flavivirus* or *Pestivirus* capsid protein, or functional fragment thereof, in the presence of the test compound do not undergo apoptosis, then an anti-apoptotic activity is indicated for the test compound. This can be confirmed if cells contacted with WNV or other viruses including *Flavivirus* or *Pestivirus* capsid protein, or functional fragment thereof, in the absence of the test compound detectably undergo apoptosis and the cells contacted with the test compound in the absence of WNV or other viruses including *Flavivirus* or *Pestivirus* capsid protein, or functional fragment thereof, do not.

A test compound is provided, preferably in solution. Serial dilutions of test compounds may be used in a series of assays. Test compounds may be added at concentrations from 0.01 µM to 1M. A preferred range of final concentrations of a test compound is from 10 µM to 100 µM.

WNV or other viruses including *Flavivirus* or *Pestivirus* capsid protein, or functional fragment thereof, may be added into the assay by a variety of means. In some embodiments of the invention, it is combined with cells as a protein. The WNV or other viruses including *Flavivirus* or *Pestivirus* capsid protein, or functional fragment thereof, may be added directly to cell culture medium. WNV or other viruses including *Flavivirus* or *Pestivirus* capsid protein, or functional fragment thereof, may be produced from widely available starting materials using well known techniques, such as those described above. A preferred concentration range of the WNV or other viruses including *Flavivirus* or *Pestivirus* capsid protein, or functional fragment thereof, used is about 1 g/ml to 1 mg/ml.

In other embodiments of the invention, WNV or other viruses including *Flavivirus* or *Pestivirus* capsid protein, or functional fragment thereof, is expressed from a nucleic acid, in the cells in the assay. In an non-limiting example, WNV or other viruses including *Flavivirus* or *Pestivirus* capsid protein, or functional fragment thereof may be expressed within the cells of the assay from a nucleic acid, under the control of an inducible promoter.

The observation of apoptosis in the cells is carried out by methods that detect the hallmark cellular changes or "markers of apoptosis." For example, early during apoptosis, alterations to the cellular membrane result in an externalization of phosphatidylserine (PS) in the cell membrane prior to eventual cell death. The constant exposure of PS during apoptosis makes it a useful "marker of apoptosis," and an attractive target for a variety of detection techniques. Annexin V, which is an endogenous human protein having a high affinity for PS, presents a convenient reagent for identifying cells undergoing apoptosis. Fluorescence-labeled annexin V can be used for histologic and cell-sorting studies to identify apoptotic cells. For example, annexin V can be conjugated to phycoerythrin (PE), a large molecule containing 25 fluors, and one of the brightest dyes used today. PE can be purchased commercially, or isolated from algae by known isolation techniques. Conjugation techniques are known to those skilled in that art, and conjugation kits can be purchased from various vendors, including ProZyme, Inc. (San Leandro, Calif.). For further details and protocols on conjugating fluorescent proteins for use in flow cytometry and other applications, see Hardy, R., Purification and coupling of fluorescent proteins for use in flow cytometry, in Handbook of Experimental Immunology, $4^{th}$ ed., Weir, Herzenberg, & Herzenberg, eds., Blackwell Scientific Pubs., Boston, 1986, which is incorporated herein by reference. Additionally, radiolabeled annexin V is useful for radiopharmaceutical imaging of apoptosing cells within tumors in the body.

Another "marker of apoptosis" is represented by the free 3'-hydroxy DNA termini, generated by the internucleosomal fragmentation of the cellular DNA by selectively activated DNases. Such free 3'-hydroxy DNA termini are not present in the intact genomic DNA of healthy cells, nor are they present when cells die via necrosis. Apoptosis-associated free 3'-hydroxy DNA termini can be detected in situ by the terminal deoxynucleotidyl transferase (TdT)-mediated dUTP nick-end labeling (TUNEL) assay. For a review of techniques for detecting DNA cleavage during apoptosis, see Kaufmann et al., 2000, Methods Enzymol., 322:3-15, which is incorporated herein by reference.

The internucleosomal fragmentation associated with apoptosis can also be detected by a sandwich assay that uses a pair of monoclonal antibodies specific for two nucleosomal epitopes to capture and detect cytoplasmic nucleosomes onto an enzyme-linked immunosorbent assay (ELISA) plate. Salgame, et al., 1997, Nucleic Acids Res., 25:680-681, which is incorporated herein by reference. This assay is particularly amenable to large scale screening of tissue culture cells.

The apoptosis detection assay may be performed using many different types of cells and delivery of *Flavivirus* or *Pestivirus* capsid protein, or functional fragment thereof, through a variety of means. One having ordinary skill in the art, following the teachings of the Specification, can readily appreciate the several ways to practice this aspect of the present invention. In preferred embodiments of the invention, the assay is performed using tumor-derived cell lines, such as the adenocarcinoma-derived HeLa cell line and the rhabdomyosarcoma-derived RD cell line, or using transformed cells, such as the adenovirus DNA-transformed kidney cell line 293.

A further aspect of the present invention relates to kits for practicing the above described method of identifying compounds which inhibit WNV or other viruses including *Flavivirus* or *Pestivirus* capsid protein, or functional fragment thereof, apoptosis-inducing activity. Kits according to this aspect of the invention comprise a container comprising WNV or other viruses including *Flavivirus* or *Pestivirus* capsid protein, or functional fragment thereof, and at least one of the following: instructions, controls, and photos or figures depicting data. Additionally, a kit may comprise a second container comprising a reagent for detecting apoptosis, such as phycoerythrin (PE)-conjugated annexin V. Alternately, the instructions can direct the user of the kit to utilize any of the many known methods of detecting markers of apoptosis. The kit may also provide the user with the cells to carry out the assay. For example, a vial of cryopreserved tumor cells may be included with the kit.

Diagnostics

There is a great need to develop diagnostic tests by which to detect the presence of antibodies to proteins from WNV or other viruses including *Flavivirus* or *Pestivirus*.

The present invention relates to a diagnostic test in which the presence and/or amount of capsid protein from WNV or other viruses including *Flavivirus* or *Pestivirus* in a test sample is determined. The present invention provides anti-capsid protein antibodies that recognize capsid protein from WNV or other viruses including *Flavivirus* or *Pestivirus*. The presence of capsid protein in a test sample from an individual may also be an excellent indicator of infection.

The present invention relates to methods of identifying individuals exposed to WNV or other viruses including *Flavivirus* or *Pestivirus* by detecting presence of capsid protein in a sample. The antibodies are preferably monoclonal antibodies. The antibodies are preferably raised against capsid protein made in human cells, CHO cells, insect cells or yeast cells. Quantification of the amount of capsid protein present in a sample of an individual may be used in determining the prognosis of an infected individual.

The present invention relates to antibodies which spefically bind to capsid protein from WNV or other viruses including *Flavivirus* or *Pestivirus*. The antibodies are preferably monoclonal antibodies. The antibodies are preferably raised against capsid protein made in human cells, CHO cells, insect cells or yeast cells.

The present invention relates to kits for identifying individuals exposed to WNV or other viruses including *Flavivirus* or *Pestivirus* comprising a first container which contains antibodies which specifically bind to capsid protein from WNV or other viruses including *Flavivirus* or *Pestivirus* and a second container which contains capsid protein as a positive control. The antibodies are preferably monoclonal antibodies. The antibodies are preferably raised against capsid protein made in human cells, CHO cells, insect cells or yeast cells. The capsid protein is preferably made in human cells, CHO cells, insect cells or yeast cells. The kits may be adapted for quantifying of the amount of capsid protein present in a sample of an individual.

Another aspect of the invention is a diagnostic test in which the presence and/or amount of anti-capsid protein from WNV or other viruses including *Flavivirus* or *Pestivirus* antibodies in a test sample is determined. In the diagnostic method of the present invention, the presence of anti-capsid protein antibodies in a test sample from an individual is an indicator of infection.

The present invention relates to methods of identifying individuals exposed to WNV or other viruses including *Flavivirus* or *Pestivirus* by detecting presence of antibodies against capsid protein from WNV or other viruses including *Flavivirus* or *Pestivirus* in sample using capsid protein. The capsid protein is preferably produced in human cells, CHO cells' insect cells or yeast cells. Quantification of the amount of anti-capsid protein antibodies present in a sample of an individual may be used in determining the prognosis of an infected individual.

The present invention relates to isolated capsid protein. The capsid protein is preferably produced in human cells, CHO cells, insect cells or yeast cells.

The present invention relates to kits for identifying individuals exposed to WNV or other viruses including *Flavivirus* or *Pestivirus* comprising a first container which contains antibodies which specifically bind to capsid protein from WNV or other viruses including *Flavivirus* or *Pestivirus* and a second container which contains capsid protein. The capsid protein is preferably produced in human cells, CHO cells, insect cells or yeast cells. The antibodies are preferably raised against capsid made in human cells, CHO cells, insect cells or yeast cells. The kits may be adapted for quantifying the amount of anti-capsid protein antibodies present in a sample of an individual. Such information may be used in determining the prognosis of an infected individual.

Kits for the detection of capsid protein from WNV or other viruses including *Flavivirus* or *Pestivirus* and anti-capsid protein from WNV or other viruses including *Flavivirus* or *Pestivirus* antibodies are useful for research as well as diagnostic and prognostic purposes.

The means to detect the presence of a protein or an antibody in a test sample are routine and one having ordinary skill in the art can detect the presence or absence of a protein or an antibody using well known methods. One well known method of detecting the presence of a protein or an antibody is in a binding assay. One having ordinary skill in the art can readily appreciate the multitude of ways to practice a binding assay to detect the presence of a protein or an antibody. For example, antibodies are useful for immunoassays which detect or quantitate a specific protein. Antigens are useful for immunoassays which detect or quantitate a specific antibody. Some immunoassays comprise allowing proteins in the test sample to bind a solid phase support or to antibodies fixed to a solid phase. Detectable antibodies are then added which selectively binding to either the protein of interest or the uncomplexed antibody. Detection of the detectable antibody indicates the presence of the protein of interest if the detectable antibody is specific for the protein or the absence of the protein of interest if the detectable antibody is specific for uncomplexed antibody. Some immunoassays comprise allowing antibodies in the test sample to bind to an antigen that is fixed to a solid phase support and detecting the antigen/antibody complex using a detectable antibody—which binds to either the antibody of interest or the antigen. Various immunoassay procedures are described in *Immunoassays for the* 80's, A. Voller et al., eds., University Park Press, Baltimore (1981), which is incorporated herein by reference.

Simple binding assays may be performed in which a solid phase support is contacted with the test sample. Any proteins present in the test sample bind the solid phase support and can be detected by a specific, detectable antibody preparation. Such a technique is the essence of the dot blot, Western blot and other such similar assays. The presence of specific antibodies in a test sample may also be detected in a similar manner. A target protein, to which the specific antibody binds, is contacted with the test sample and the subsequent binding to antibodies, if present in the test sample, is analyzed by a variety of methods known to those skilled in the art. Any antibodies present in the test sample bind the solid phase support and can be detected by detectable antigen or a specific, detectable antibody preparation.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control. Such "two-site" or "sandwich" assays are described by Wide, *Radioimmune Assay Method*, Kirkham, ed., E. & S. Livingstone, Edinburgh (1970) pp. 199-206, which is incorporated herein by reference.

The "forward" assay may also be adapted for the detection of antibodies that may be present in a test sample, henceforth referred to as "sample antibodies." The specific target protein to which the sample antibodies bind is bound to the solid phase support and contacted with the test sample. After a suitable incubation period, the solid phase support is washed to remove unbound sample antibodies. A first antibody that binds to the Fc portion of the sample antibodies is added. This first antibody is preferably detectable. Alternative, in the case where the first antibody is not detectable, a second detectable antibody which binds the first antibody must be used to detect the binding. After a second incubation period to permit the detectable antibody to complex with the sample antibody bound to the target protein/solid phase support, the solid phase support is washed a second time to remove the unbound detectable antibody. This type of "forward sandwich" assay may also be a simple yes/no assay to determine whether binding has occurred or may be made quantitative by comparing the measure of detectable antibody with that obtained in a control.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The first component of the immunometric assay may be added to nitrocellulose or other solid phase support which is capable of immobilizing proteins. The first component for determining the presence of capsid protein from WNV or other viruses including *Flavivirus* or *Pestivirus* in a test sample is anti-capsid protein antibody, whereas the first component for examining for the presence of anti-capsid protein antibodies in a test sample is capsid protein. By "solid phase support" or "support" is intended any material capable of binding proteins. Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

To detect the presence of a protein, in this case either capsid protein or anti-capsid protein antibodies, detectable antibodies, such as anti-capsid protein antibodies or anti-human antibodies, are used. Several methods are well known for the detection of antibodies.

One method in which the antibodies can be detected is by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. One skilled in the art would readily recognize other enzymes which may also be used.

Another method in which antibodies can be detected is by linking the antibodies to radioactive isotopes for subsequent use in a radioimmunoassay (RIA) (see, for example, Work, T. S. et al., *Laboratory Techniques and Biochemistry in Molecular Biology*, North Holland Publishing Co., NY (1978), which is incorporated herein by reference). The radioactive isotope can be detected by such means as the use of a gamma counter or a scintillation counter or by autoradiography. Isotopes which are particularly useful for the purpose of the present invention are $^{3}H$, $^{125}I$, $^{131}I$, $^{35}S$, and $^{14}$C. Preferably $^{125}$I is the isotope. One skilled in the art would readil recognize other radioisotopes which may also be used.

It is also possible to label the antibody with a fluorescent compound. When the fluorescent-labeled antibody is exposed to light of the proper wave length, its presence can be detected due to its fluorescence. Among the most commonly used fluorescent labeling compounds are fluorescein isothiocyanate, rhodamine, phycoerythrin, phycocyanin, allophycocyanin, α-phthaldehyde and fluorescamine. One skilled in the art would readily recognize other fluorescent compounds which may also be used.

Antibodies can also be detectably labeled using fluorescence-emitting metals such as $^{152}$Eu, or others of the lanthanide series. These metals can be attached to the protein-specific antibody using such metal chelating groups as diethylenetriaminepentaacetic acid (DTPA) or ethylenediamine-tetraacetic acid (EDTA). One skilled in the art would readily recognize other fluorescence-emitting metals as well as other metal chelating groups which may also be used.

Antibodies can also be detectably labeled by coupling to a chemiluminescent compound. The presence of the chemiluminescent-labeled antibody is determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. One skilled in the art would readily recognize other chemiluminescent compounds which may also be used.

Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase, and aequorin. One skilled in the art would readily recognize other bioluminescent compounds which may also be used.

Detection of the protein-specific antibody, fragment or derivative may be accomplished by a scintillation counter if, for example, the detectable label is a radioactive gamma emitter.

Alternatively, detection may be accomplished by a fluorometer if, for example, the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

The binding activity of a given lot of antibodies may be determined according to well known methods. Those skilled in the art will be able to determine operative and optimal assay conditions for each determination by employing routine experimentation.

Positive and negative controls may be performed in which known amounts of protein and no protein, respectively, are added to the assay. One skilled in the art would have the necessary knowledge to perform the appropriate controls. To determine the quantity of capsid protein or anti-capsid protein antibodies in a test sample, the amount of protein detected in the test sample is compared to the amount of protein detected in the positive control. A standard curve is generated from the positive control values and the amount of protein in the test sample is extrapolated from said standard curve. One skilled in the art would have the knowledge to construct a standard curve and extrapolate the value of the test sample. Test samples include those samples that are obtained from individuals suspected of being infected by WNV or other viruses including *Flavivirus* or *Pestivirus* may consist of blood, cerebral spinal fluid, amniotic fluid, lymph, semen, vaginal fluid or other body fluids. Test samples also include those samples prepared in the laboratory, such as those used for research purposes. Cells, if present, may be removed by methods such as centrifugation or lysis. One skilled in the art would readily appreciate the variety of test samples that may be examined for capsid protein and anti-capsid protein antibodies. Test samples may be obtained by such methods as withdrawing fluid with a needle or by a swab. One skilled in the art would readily recognize other methods of obtaining test samples.

An "antibody composition" refers to the antibody or antibodies required for the detection of the protein. For example, the antibody composition used for the detection of capsid protein in a test sample comprises a first antibody that binds to capsid protein as well as a second or third detectable antibody that binds the first or second antibody, respectively.

To examine a test sample for the presence of anti-capsid protein antibodies, a standard immunometric assay may be performed. 10-50 μg/ml of capsid protein is added to a solid phase support, such as a 96-well microtiter plate, in a volume of buffer. 50 μl are added per well. The solid phase support is incubated for a period of time sufficient for binding to occur and subsequently washed with phosphate-buffered saline (PBS) to remove unbound capsid protein. Examples of appropriate conditions are 2 hours at room temperature or 4° C. overnight. The solid phase support is then blocked with a PBS/BSA solution to prevent proteins in the test sample from nonspecifically binding the solid phase support. Serial dilutions of test sample are added to the solid phase support which is subsequently incubated for a period of time sufficient for binding to occur. The solid phase support is washed with PBS to remove unbound protein. Labeled anti-human antibodies, which recognize the Fc region of human antibodies, are added to the solid phase support mixture. The plate is incubated for a period of time sufficient for binding to occur and subsequently washed with PBS to remove unbound labeled anti-human antibody. The amount of bound labeled anti-human antibodies is subsequently determined by standard techniques. The anti-human antibodies that may be used include horseradish peroxidase-labeled, goat anti-human antibodies (Boehringer Mannheim), used at 1:12,000 according to the manufacturer's directions.

To examine a test sample for the presence of capsid protein, a standard immunometric assay such as the one described below may be performed. A first anti-capsid protein antibody, which recognizes a specific portion of capsid protein is added to a 96-well microtiter plate in a volume of buffer. The plate is incubated for a period of time sufficient for binding to occur and subsequently washed with PBS to remove unbound anti-capsid protein antibody. The plate is then blocked with a PBS/BSA solution to prevent sample proteins from nonspecifically binding the microtiter plate. Serial dilutions of test sample are subsequently added to the wells and the plate is incubated for a period of time sufficient for binding to occur. The wells are washed with PBS to remove unbound protein. Labeled anti-capsid protein antibodies, which recognize portions of capsid protein not recognized by the first anti-capsid protein antibody are added to the wells. The plate is incubated for a period of time sufficient for binding to occur and subsequently washed with PBS to remove unbound, labeled anti-capsid protein antibody. The amount of bound labeled anti-capsid protein antibody is subsequently determined by standard techniques. A rabbit anti-capsid antibody that recognizes capsid protein is used at 1:1000. Examples of appropriate conditions are 2 hours at room temperature or 4° C. overnight.

Kits which are useful for the detection of capsid protein in a test sample, comprise solid support, positive and negative controls, buffer, appropriate anti-capsid protein antibodies and instructions for carrying out the capture ELISA assay essentially as previously described. Kits which are useful for the detection of anti-capsid protein antibodies in a test sample, comprise solid support, positive and negative controls, buffer, capsid protein and instructions for carrying out the capture ELISA assay essentially as previously described.

While the portions of the disclosure herein which relate to therapeutic compositions and methods primarily relate to therapeutics and methods of treating humans, the compositions and methods of the present invention can be applied to veterinary medical uses as well. It is within the scope of the present invention to provide methods of treating non-human as well as human individuals. Accordingly, the present invention relates to a method of treating all animals, particularly mammalian species including human, bovine, ovine, porcine, equine, canine and feline species.

The invention is further illustrated by way of the following examples which are intended to elucidate the invention. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

EXAMPLES

Example 1

Capsid Protein Expression Constructs

Two WNV capsid protein (Cp) expression vectors (pWNVh-DJY and pWNVy-DJY) were constructed, based on the reported polyprotein gene sequence for the New York 1999 human isolate of the virus (WNV-HNY1999) (GenBank accession number AF202541, Jia et al., 1999, Lancet, 354:1971-1972). The genomic organization of WNV-HNY1999 is presented in the top portion of FIG. 1. The construction of the vectors is presented schematically in the bottom portion of FIG. 1. Each construct contains the coding sequence for a signal peptide (leader sequence) from a human IgE (sIgE) fused 5' upstream of the Cp open reading frame (ORF), minus the coding sequence for the first amino acid of Cp (the first amino acid residue (met) is deleted). The clones were constructed using an overlapping PCR approach with three separate PCR reactions, using primer sets designed to introduce species-optimized codons (Kim et al., 1997, Gene, 199:293-301, which is incorporated herein by reference) into the final constructs. The pWNVh-DJY construct contains human-optimized codons for the entire fused sIgE signal peptide/Cp coding sequence. The pWNVy-DJY construct contains yeast-optimized codons for the signal peptide and codons for Cp protein amino acid residues 2 through 6, and human-optimized codons for the rest of the Cp coding sequence. In addition, a proper Kozak sequence was introduced upstream of the signal peptide coding sequence, by use of the PCR primers. Each coding sequence was cloned into pcDNA3.1/V5-HisC (Invitrogen, San Diego, Calif.), between the HindIII and NotI polycloning sites, to yield expression constructs under the control of the CMV promoter that will express a Cp-His tag fusion protein. Both constructs encode identical proteins having an amino-terminal sIgE leader peptide, fused to amino acids 2 through 123 of WNV Cp protein, followed by the V5 epitope, and a polyhistidine carboxy-terminal tail.

The overlapping PCR construction made use of the following ten primers:

```
Primer 1. sIgh-VChU1+ (90 mer)
                                        (SEQ ID NO: 14)
ATGGACTGGACCTGGATCCTGTTCCTGGTGGCCGCCGCCACCCGCGTGCA
CAGCTCTAAGAAACCAGGAGGCCCCGGCAAGAGCCGCGCC.

Primer 2. sIgy-VCyU1.1+ (90 mer)
                                        (SEQ ID NO:15)
ATGGATTGGACTTGGATCTTATTTTTAGTTGCTGCTGCTACTAGAGTTCA
TTCTTCTAAAAAACCAGGTGGCCCCGGCAAGAGCCGCGCC.

Primer 3. sIgh-VChL1- (88 mer)
                                        (SEQ ID NO:16)
GGCTCAGCATGGCGCGCTTCAGGCCAATCAGGCTCAGCACGCGGGGCATG
CCGCGCTTCAGCATGTTCACGGCGCGGCTCTTGCCGGG.

Primer 4. sIgh-VChU2+ (90 mer)
                                        (SEQ ID NO: 17)
GGCCTGAAGCGCGCCATGCTGAGCCTGATCGACGGCAAGGGCCCCATACG
CTTCGTGCTGGCCCTGCTGGCCTTCTTCCGCTTCACCGCC.

Primer 5. sIgh-VChL2- (89 mer)
                                        (SEQ ID NO: 18)
GGTGCTTCATGGCGGTCTGCTTGTTCACGCCGCGCCAGCGGTCCAGCACG
GCGCGGGTGGGGGCAATGGCGGTGAAGCGGAAGAAGGCC.

Primer 6. sIgh-VChU3+ (89 mer)
                                        (SEQ ID NO: 19)
CCGCCATGAAGCACCTGCTGAGCTTCAAGAAGGAGCTGGGCACCCTGACC
AGCGCCATCAACCGCCGCAGCAGCAAGCAGAAGAAGCGC.

Primer 7. sIgh-VChL3- (81 mer)
                                        (SEQ ID NO:20)
CGCGCCCACGCTGGCGATCAGGCCAATCATCACGGCAATGCCGGTCTTGC
CGCCGCGCTTCTTCTGCTTGCTGCTGCGGCG.

Primer 8. sIgh-VChFS1+ (39 mer)
                                        (SEQ ID NO:21)
CCCAAGCTTGCCGCCACCATGGACTGGACCTGGATCCTG.

Primer 9. sIgy-VCyFS1.1+ (33 mer)
                                        (SEQ ID NO:22)
CCCAAGCTTGCCGCCACCATGGATTGGACTTGG.

Primer 10. sIgh-VChFAS2- (37 mer)
                                        (SEQ ID NO:23)
ATAGTTTAGCGGCCGCGCCCACGCTGGCGATCAGGCC.
```

Figure 3:
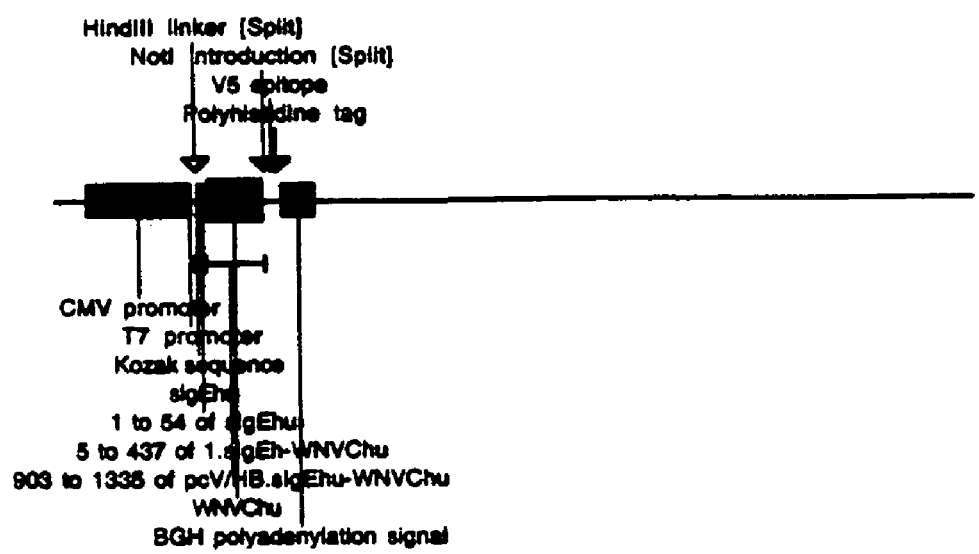
FIG. 3 presents the feature map of WNV capsid protein expression vector pWNVh-DJY.
Figure 5:
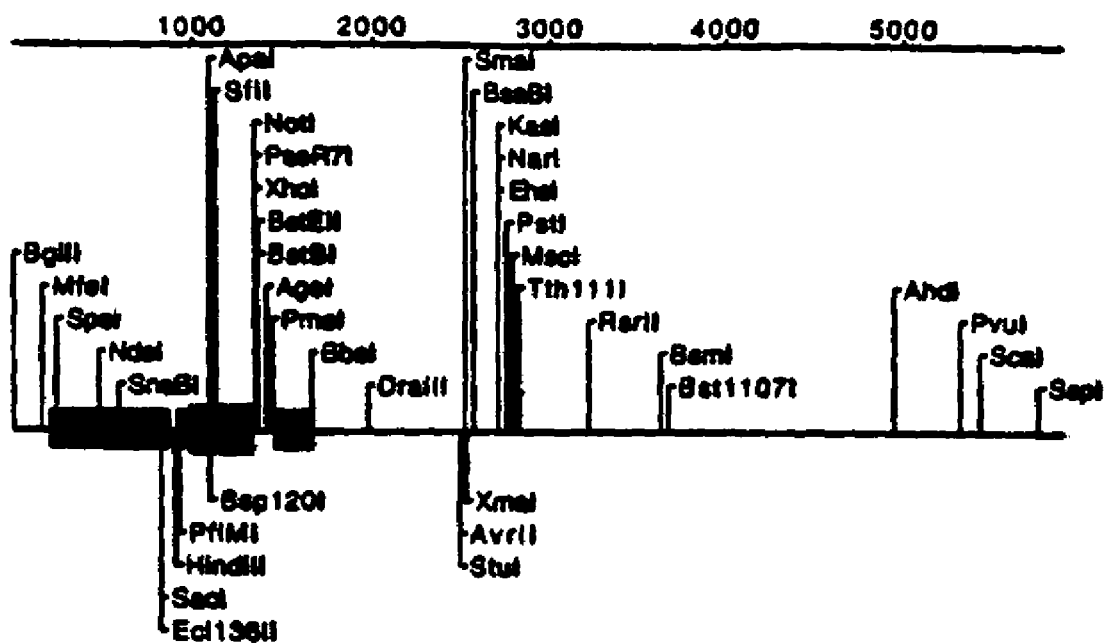
FIG. 5 presents the restriction endonuclease map of WNV capsid protein expression vector pWNVy-DJY.
Figure 6:
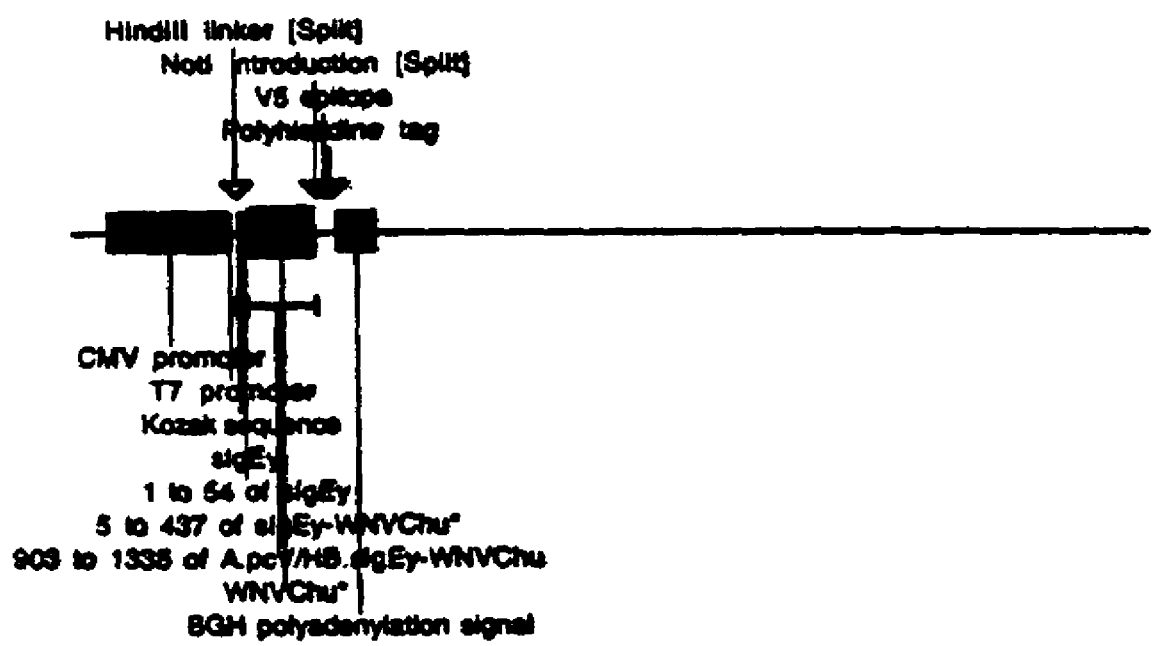
FIG. 6 presents the feature map of WNV capsid protein expression vector pWNVy-DJY.

Three sets of primers were paired for PCR reactions to generate three overlapping PCR products as follows: primers 1 and 3 (for pWNVh-DJY) or primers 2 and 3 (for pWNVy-DJY), primers 4 and 5, and primers 6 and 7. Each set of primers was self-annealed and extended by Pfu DNA polymerase (Stratagene, La Jolla, Calif.). The final, full-length inserts were amplified with a primer set of primers 8 and 10 (to generate the insert for pWNVh-DJY) or primers 9 and 10 (to generate the insert for pWNVy-DJY), and subsequently tailed with HindIII (5' end) and NotI (3' end) endonuclease restriction sites. These final insert products were restricted with HindIII and NotI, and cloned into HindIII/NotI-digested pcDNA3.11V5-H is C. The resultant recombinant vectors (pWNVh-DJY and pWNVy-DJY) were confirmed by sequencing. FIGS. 2 and 5 present the restriction endonuclease maps of pWNVh-DJY and pWNVy-DJY, respectively. FIGS. 3 and 6 present the feature maps of pWNVh-DJY and pWNVy-DJY, respectively. FIGS. 4 and 7 present the complete, annotated nucleotide sequences for pWNVh-DJY and pWNVy-DJY, respectively.

Example 2

Biological Characterization of WNV Capsid Protein Expressed from pWNVy-DJY and pWNVh-DJY Expression of Cp Protein from pWNVy-DJY and pWNVh-DJY in Tissue Culture Cells HeLa, RD, or 293 cells, seeded onto two-chamber slides, were transfected by the $CaPO_4$ precipitation method with 2 µg of purified plasmid DNA (either pWNVy-DJY or pWNVh-DJY). Following transfection, the cells were fixed cells and incubated with mouse anti-His mAb and then incubated with FITC-conjugated goat anti-mouse IgG Ab. The gene expression was examined with UV lamp microscope. Expression of Cp protein was achieved in all three cell lines from both constructs pWNVy-DJY and pWNVh-DJY, and the protein was localized in the cytoplasm. Immunofluoresence analysis of the expression of Cp protein in RD cells transfected with pWNVh-DJY revealed a green signal representing localized Cp protein using a FITC filter. The images were also captured with a dual filter of FITC and rhodamine to distinguish between specific and background signals. Green fluorescence under the dual filter confirmed the presence of Cp protein. A DAPI filter was used to reveal the nuclei of the cells, which were stained with DAPI (4',6-diamidine-2'-phenylindole, dihydrochloride), and cellular morphology was revealed when the image was captured with a DAPI filter in the light field.

In Vitro Translation of WNV Capsid Protein $^{35}$S-labeled protein products were prepared using the TNT-T7 coupled Transcription/Translation System (Promega, Madison, Wis.). Ten µl of radiolabeled protein samples and 1 µl of anti-His (C-term) (Invitrogen, San Diego, Calif.) antibody were added to 300 µl of RIPA buffer and mixed gently. After an incubation at 4° C. for 90 minutes, Protein A-Sepharose beads (LKB-Pharmacia Biotech) were added to the protein-antibody complexes at a final concentration of 5 µg per tube and the samples were incubated at 4° C. for 90 minutes in a rotating shaker. The beads were washed three times with RIPA buffer and suspended in 2×SDS sample buffer. The immunoprecipitated protein complexes were eluted from the Sepharose beads by brief boiling and resolved in SDS-PAGE (15%) gels. The mobilities of the protein samples were compared with that of commercially available, $^{14}$C-methylated molecular weight markers (Sigma). The gel was fixed, treated briefly with 1M sodium salicylate solution and dried in a gel dryer (BioRad). The dried gel was exposed overnight to X-ray film (Kodak). The in vitro translated proteins had an apparent molecular size of 21.5 kDa (FIG. 8).

Example 3

Evaluation of Immune Response Against WNV Capsid Protein Expressed from pWNVy-DJY and pWNVh-DJY Peptides Three major histocompatibility (MHC) class 1'-restricted epitopes of the WNV Cp amino acid sequence were chosen using Mac Vector software (Oxford Molecular Group, MA), which is capable of predicting antigenic determinants and hydrophilic regions. The peptides were synthesized by standard peptide synthesis, and were as follows:

| Peptide Name | WNV Cp Protein Residues | Amino Acid Sequence | SEQ ID NO |
|---|---|---|---|
| WNVC-P1 | 2-23 | SKKPGGPGKSRAVNMLKRGMPR | SEQ ID NO:6 |
| WNVC-P2 | 31-49 | KRAMLSLIDGKGPIRFVLA | SEQ ID NO:7 |
| WNVC-P3 | 90-111 | TLTSAINRRSSKQKKRGGKTGI | SEQ ID NO:8 |

FIG. 8 presents these peptides aligned along the length of the WNV Cp protein.

In Vitro Translated Protein

Non-radioactive, in vitro translated Cp protein was also generated as described above in Example 2, using the TNT-T7 coupled Transcription/Translation System (Promega, Madison, Wis.) with non-radioactive components. An in vitro translation control was generated using the in vitro translation kit with the pcDNA3.1 vector (Invitrogen, San Diego, Calif.), lacking an expressible insert DNA Inoculation of Mice To evaluate the T cell-mediated immune response against the WNV Cp gene product, an in vivo mouse experiment was set up. The quadriceps muscles of 6- to 8-week-old female BALB/c mice (Harlan Sprague Dawley, Inc., Indianapolis, Ind.) were injected with 100 µg of pWNVh-DJY, pWNVy-DJY, or pcDNA3.1 (without an insert) in PBS and 0.25% bupivacaine-HCl (Sigma, St Louis, Mo.). Two weeks later, the mice received a boost of another 100 µg DNA injections. Thirteen days after the boost injection, the mice were sacrificed, the spleens were harvested, and the lymphocytes were isolated and tested for cellular immune responses.

Lymphoproliferative Assay

Harvested splenic lymphocytes were pooled for two mice in each immunized group and suspended to a concentration of $5 \times 10^6$ cells/ml. A 100 µl aliquot, containing $5 \times 10^5$ cells, was immediately added to each well of a 96-well, flat bottom microtiter plate. Reconstituted peptide, in vitro translated protein, or in vitro translation control were added to the wells, at concentrations of 5 µg/ml and 1 µg/ml (and 0.5 µg/ml for in vitro translated protein and in vitro translation control protein). Concanavalin A (Con A) was used as a positive proliferation control. The assay conditions were set up in triplicate. The cells were incubated at 37° C. in 5% $CO_2$ for three days. One µCi of tritiated thymidine was added to each well and the cells were incubated for 18 hours at 37° C. The plate was harvested and the amount of incorporated tritiated thymidine was measured in a Beta Plate reader (Wallac, Turku, Finland). Stimulation Index was determined from the formula:

Stimulation Index (SI)=(experimental count/spontaneous count).

Spontaneous count wells included 5% fetal bovine serum which served as an irrelevant protein control. The results are presented in Table 1.

Splenocytes isolated from mice immunized with either pWNVy-DJY or pWNVh-DJY ("H" or "Y") and incubated with WNVC-P3 ("Peptide 3") or a mixture of all three Cp peptides ("Peptide 123") yielded SI values significantly higher than did splenocytes isolated from mice in the group immunized with the base vector pcDNA3.1.

TABLE 1

| Antigen or Stimulus | Splenocyte Source | Concentration of Protein or Peptide | | |
|---|---|---|---|---|
| | | 5 µg/ml | 1 µg/ml | 0.5 µg/ml |
| Peptide 1 | H | 0.5 | 0.7 | |
| | Y | 0.8 | 1.2 | |
| | pcDNA3.1 | 0.9 | 1.3 | |
| Peptide 2 | H | 1.7 | 1.3 | |
| | Y | 1.6 | 1.8 | |
| | pcDNA3.1 | 0.9 | 1.0 | |
| Peptide 3 | H | 1.5 | 2.0 | |
| | Y | 1.1 | 1.4 | |
| | pcDNA3.1 | 0.8 | 0.7 | |
| Peptide 123 | H | 2.6 | 3.9 | |
| | Y | 1.8 | 2.1 | |
| | pcDNA3.1 | 0.7 | 1.2 | |
| Y protein | H | 0.0 | 0.8 | 1.7 |
| | Y | 0.0 | 0.6 | 1.7 |
| | pcDNA3.1 | 0.0 | 1.2 | 1.2 |
| Ctrl pro | H | 0.0 | 0.5 | 2.7 |
| | Y | 0.3 | 0.4 | 1.8 |
| | pcDNA3.1 | 3.8 | 1.8 | 1.9 |
| Con A | H | 686.5 | | |
| | Y | 366.9 | | |
| | pcDNA3.1 | 71.8 | | |

Table 1 presents the results of the lymphoproliferation assay. The values presented for each condition are stimulation indices averaged over triplicate wells. For each immunization group tested, splenocytes were pooled from two mice within the group. "H" indicates splenocytes from the pWNVh-DJY-immunized group. "Y" indicates splenocytes from the pWNVh-DJY-immunized group of mice. "pcDNA3.1" indicates splenocytes from the pcDNA3.1-immunized control group of mice. Peptides 1, 2, and 3 are the WNVC-P1, WNVC-P2, and WNVC-P3 peptides described above. "Peptide 123" indicates a mixture of peptide 1, 2, and 3. "Y protein" indicates the Cp protein in vitro translated from the pWNVy-DJY construct. "Ctrl pro" indicates the in vitro translation control, generated with pcDNA3.1 vector containing no expressible insert, as described above.

Detection of Intracellular IFN-γ by Flow Cytometry

100 μl RPMI-1640, supplemented with 5% fetal bovine serum (FBS) (R5 medium), containing 50 U/ml recombinant human interleukin-2 (rHuIL-2) (Intergen, Purchase, NY), 10 μg/ml brefeldin A (BD PharMingen, San Diego, Calif.), 100 ng/ml phorbol 12-myristate 13-acetate (PMA) (Sigma, St. Louis, Mo.), and 1 μg/ml ionomycin (Sigma), was added to each well of a round-bottom 96-well plate. In vitro translated Cp protein or in vitro translated control protein, at 4 μg/ml, was added in 50 μl of R5 medium. After adding the protein antigens (Ag), isolated splenocytes were added to each well at $1\times10^6$ cells in 50 μl of R5 medium. For the compensation in flow cytometry, splenocytes from naïve mice were incubated with only IL-2 and brefeldin A. The plates were incubated in a 37° C., 5% $CO_2$ incubator for 5 to 6 hours. As a control, splenocytes were also incubated without Ag. After incubation, plates were spun at 1200 rpm for 5 minutes and supernatants were discarded. The cells in each well were resuspended with 200 μl of PBS, supplemented with 1% bovine serum albumin (BSA), put on ice for 15 minutes, spun at 1200 rpm, and resuspended with in 50 μl PBS/1% BSA containing 0.1 μg of PE-conjugated, anti-CD4 mAb and 0.1 μg CyC-conjugated anti-CD44 nmAb (both from BD PharMingen, San Diego, Calif.). After incubating for 30 minutes at 4° C., the cells were washed twice with PBS/1% BSA, the cell pellets were resuspended with 100 μl of Cytofix/Cytoperm solution (BD PharMingen, San Diego, Calif.), and incubated for 20 minutes at 4° C. The cells were washed twice with 1× Perm/Wash (BD PharMingen, San Diego, Calif.), and resuspended with 50 μl of Perm/Wash solution containing allophycocyanin (APC)-conjugated anti-IFN-γ antibody (BD PharMingen, San Diego, Calif.) at 0.1 μg/sample concentration. After incubation for 30 minutes at 4° C., the cells were washed twice with 1× Perm/Wash solution and fixed with 2% paraformaldehyde and stored at 4° C. until being analyzed by flow cytometry.

CD44 expression is used as an activation marker. CD44 is a cell adhesion receptor, widely expressed on hematopoietic and non-hematopoietic cells. BALB/c mice have relatively large subsets of CD44H+ T cells. In the periphery, the level of CD44 expression increases upon activation of B cells, CD4+ T cells, CD8+ T cells, and memory cells, which can be identified by their CD44hi phenotype (expressing high levels of CD44H isoform). $CD4^+$ T cell-dependent intracellular IFN-1 production was quantitated by flow cytometry. The results, as presented in FIG. 10, show an antigen-specific, IFN-γ response for splenocytes from mice immunized with base vector pcDNA3.1 or Cp protein expression constructs pWNVh-DJY or pWNVy-DJY. Splenocytes isolated from pWNVy-DJY-immunized mice, expressed higher levels of IFN-γ upon stimulation with in vitro translated Cp protein, than did the splenocytes isolated from pWNVh-DJY-immunized mice.

Example 4

Examination of Apoptosis by the TUNEL Assay

Apoptosis in individual cells was determined by the TUNEL assay, in three different cell lines: HeLa cells, RD cells, and 293 cells. Cells were transfected with either the pWNVh-DJY or pWNVy-DJY construct and examined for apoptosis by the TUNEL assay. Both constructs induced apoptosis in all three cell lines.

The TUNEL assay was carried out using the "In situ Cell Death Detection Kit, Fluorescein" (Roche Molecular Biochemicals, Indianapolis, Ind.), according to the manufacturer's protocol. DNA cleavage was detected by terminal transferase (TdT) labeling of free 3'-hydroxy termini in genomic DNA with fluorescein-dUTP. Briefly, cells were fixed and permeabilized with PBS, supplemented with 0.1% Triton-X, 0.1% sodium citrate, and then the cells were incubated with "TUNEL reaction mixture," containing TdT and fluorescein-dUTP. The fluorescein-linked, incorporated dUTP was detected by fluorescence microscopy.

The data for analysis of HeLa cells, RD cells, and 293 cells transfected with either pWNVh-DJY or pWNVy-DJY construct were captured with different filters in the microscope to identify specific signals. A green signal represented incorporated fluorescein into the apoptotic cells, as revealed by a FITC filter. Images of the cells were also captured with a dual filter of FITC and rhodamine to distinguish between specific apoptotic signals and background signals. Green fluorescence under the dual filter reflected a true fluorescent signal from incorporated fluorescein-dUTP. A DAPI filter was used to reveal the nuclei of the cells, which were stained with DAPI. Not all cells were TUNEL positive. Cellular morphology was revealed when the image was captured with a DAPI filter in the light field, and showed that the nuclei of the apoptotic cells were condensed.

Similar results have been obtained with the pWNVy-DJY construct in the human neuroblastoma cell line (ATCC # CRL-2266).

Example 5

Annexin V Flow Cytometry Analysis

HeLa cells were transfected with the enhanced green fluorescent protein (EGFP) expression vector pEGFP2-N 1 (Clontech) alone, as a marker of transfection, or with pEGFP2-N1 in combination with either pWNVh-DJY or pWNVy-DJY. Two days post transfection, the cells were stained with phycoerythrin (PE)-conjugated annexin V. Stained cells were analyzed by flow cytometry. Annexin V positive cell populations were counted from the gate of EGFP-positive events, and the data were acquired using CellQuest software. Up to ten-fold induction of apoptosis over the control cells was observed by treatment with WNV-Cp (FIG. 13).

Example 6

Analysis of Apoptosis-Inducing Domains of WNV Cp Protein

Peptide WNVC-P3, as described in Example 3 and FIG. 11 above, was tested for its ability to induce apoptosis in cells in culture. Peptide WNVC-P3 was incubated with SH-SY5Y neuroblastoma cells (ATCC; Manassas, Va.) at a concentration of 10 μg peptide per $1\times10^5$ cells. After 24 hours, TUNEL analyses were carried out TUNEL-positive cells were identified for cells treated with the WNVC-P3 peptide, but not for cells treated with a control peptide from prostate-specific antigen (PSA).

Example 7

Immunization with pCWNVCp Induces Antigen-Specific Humoral Immune Responses

To investigate the levels of in vivo immune responses generated by the DNA vaccine, mice were immunized intramuscularly with pCWNVCp or pcDNA3 control plasmid. The quadriceps muscles of 6 to 8 weeks old female BALB/c mice (Harlan Sprague Dawley, Inc., Indianapolis, Ind.) were injected with 100 μg of each DNA construct of interest formulated in phosphate buffered saline (PBS) and 0.25% bupivacaine-HCl (Sigma, St. Louis, Mo.), at 0, 4, and 8 weeks. Prior to injection and at various time points following injection, the mice were bled retro-orbitally and the sera were collected for later analysis. The collected sera samples were analyzed for specific antibody responses against Cp peptide (WNVC-P3: TLTSAINRRSSKQKKRG-GKTGI) by ELISA at 1:100, 1:400, 1:800, and 1:1600 dilution. 50 μl of WNVC-P3, diluted in PBS to a concentration of 10 μg/ml, was adsorbed onto microtiter wells overnight at 4° C., as previously described in Kim et al., 1998, CD8 positive T cells controls antigen-specific immune responses through the expression of chemokines, J. Clin. Invest., 102:1112-1124, which is incorporated herein by reference. The plates were washed with PBS-0.05% Tween-20 and blocked with 3% BSA in PBS with 0.05% Tween-20 for one hour at 37° C. Mouse antisera was diluted with 0.05% Tween-20 and incubated for one hour at 37° C., then incubated with HRP-conjugated goat anti-mouse IgG (Sigma, St. Louis, Mo.). The plates were washed and developed with 3'3'5'5' TMB (Sigma) buffer solution.

The pre-injection sera (collected at day 0) did not show any Cp-specific antibody response (Data not shown). The mice immunized with pcDNA3 control did not show any Cp-specific antibody response, but potent Cp-specific antibody responses were detected for mice immunized with pCWNVCp (FIG. 12A). Notably, the level of Cp-specific antibody response generated by DNA immunization was more potent than that of the positive hyper-immune mouse sera obtained from ATCC (Manassas, Va.).

Additionally, the subclasses of WNVCp-specific IgGs induced by the DNA vaccines were determined. It has been reported that production of IgG1 isotype is induced by Th2 type cytokines, whereas the IgG2a isotype is regulated by Th1 type cytokines (Finkelman et al., 1990, Lymphokine control of in vivo immunoplobulin isotype selection, Ann. Rev. Immunol., 8:303-333, which is incorporated herein by reference). For the determination of relative levels of Cp-specific IgG subclasses, anti-murine IgG1 and IgG2a conjugated with HRP (Zymed, San Francisco, Calif.) were substituted for anti-murine IgG-HRP. This was followed by addition of the ABTS substrate solution (Chemicon, Temecula, Calif.). In each step, plates were washed 3 times with the wash buffer (PBS+0.05% Tween-20). The plates were read on a Dynatech MR5000 plate reader with the optical density at 450 nm. As shown in FIG. 12B, most of the IgG response generated from DNA immunization with pCWTVCp was of the IgG2a isotype. This strong Th1-type bias was demonstrated by both the magnitude of IgG2a and the relative ratio of IgG2a to IgG1 (Th1 to Th2).

WNVCp-specific serum antibody was determined by immunoprecipitation/Western blot analysis. WNVCp protein, translated in vitro without radioisotope, was immunoprecipitated with an anti-6×His (C-term) polyclonal Ab (MBL, Nagoya, Japan) and resolved on a 15% of SDS-PAGE gel and transferred to a PDVF membrane (Millipore), which was cut into strips. Each strip was incubated with mouse immune sera from pCWNVCp or pcDNA3 immunized mice (at 1:100 dilution) and hybridized with horseradish peroxidase (HRP) conjugated anti-mouse IgG at a concentration of 1:2000. After rinsing, the strips were developed with ECL Chemiluminescent detection Kit (Amersham) (FIG. 12C).

Example 8

Immunization with pCWNVCp Induces Potent Antigen-Specific Th1-Type Cellular Immune Responses The level of cytokines released by T cells reflects the direction and magnitude of the immune response. The level of Th1 (IFN-γ and IL-2) and Th2 (IL-4) type cytokines produced by stimulated T cells were examined. IFN-γ, a prototypical Th1-type cytokine, is produced predominantly by CD4+ Th1 cells and CD8+ T cells. The level of IFN-γ expressed by stimulated T cells reflects the magnitude of the T cell response. IL-2 is a Th1-type cytokine produced primarily by T cells activated by external stimulation; it is critical for the proliferation and clonal expansion of antigen-specific T cells (Morgan et al., 1976, Selective in vitro growth of T lymphocytes from normal human bone narrows, Science, 193:1007-1008, which is incorporated herein by reference). On the other hand, IL-4 is a prototypical Th2- type cytokine that plays a dominant role in B cell-mediated immune responses (Seder & Paul, 1994, Acquisition of lymphokine-producing phenotype by CD4+ T cells. Annu. Rev. Immunol., 12:635-673, which is incorporated herein by reference).

The level of CD4+ T helper cell-mediated immune responses following immunization was also examined. Mice received two DNA immunizations (100 µg each) separated by two weeks. At one week after the second injection, the mice were euthanized, the spleens harvested. Lymphocytes were harvested from spleens and prepared as effector cells by removing the erythrocytes and by washing several times with fresh media as described in Kim et al., 1997, Engineering of in vivo immune responses to DNA immunization via co-delivery of costimulatory molecule genes, Nat. Biotechnol., 15:641-646, which is incorporated herein by reference. The isolated cell suspensions were resuspended to a concentration of $5 \times 10^6$ cells/ml. A 100 µl aliquot containing $5 \times 10^5$ cells was immediately added to each well of a 96 well microtiter flat bottom plate. WNV capsid-specific peptide pools (WNVC-P1: SKKPGGPGKSRAVNMLKRGMPR; WNVC-P2: KRAMLSLIDGKGPIRFVLA; WNVC-P3: TLTSAINRRSSKQKKRGGKTGI) at the final concentration of 5 µg/ml were added to wells in triplicate. The cells were incubated at 37° C. in 5% $CO_2$ for 4 days. Supernatants from these wells were collected at day 4 and tested for tested for the release of IFN-γ, IL-2, or IL-4 by cytokine ELISA using ELISA kits (Biosource, Camarillo, Calif.; R&D Systems, Minneapolis, Minn.).

Figure 13:
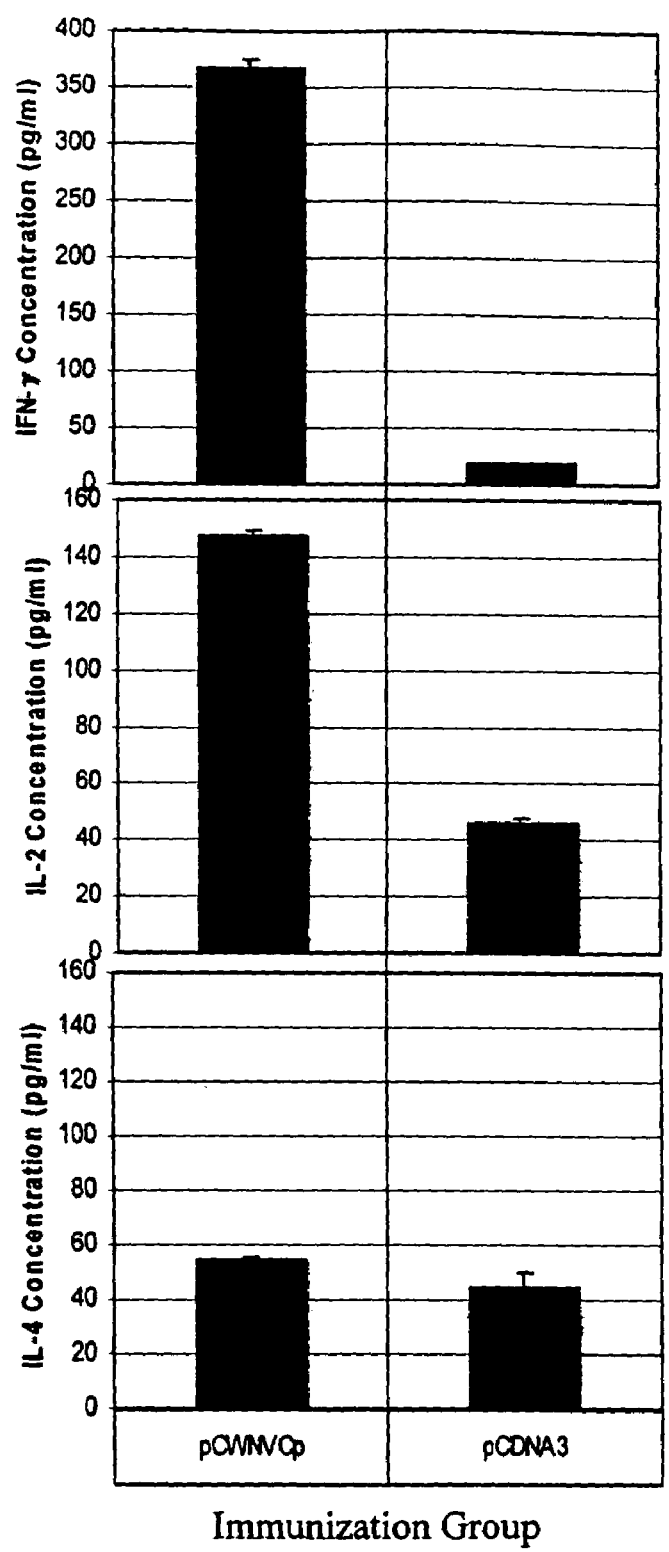
FIG. 13 shows production of IFN-γ (Th1), IL-2 (Th1) and IL-4 (Th2) by stimulated T cells. Mice were immunized and their splenocytes were prepared as described in Example 8. The isolated lymphocytes were stimulated for 3 days with WNV Cp pooled peptides. Supernatants were collected and assayed for IFN-γ, IL-2, and IL-4 profiles using ELISA kits. The error bars represent standard deviation (S.D.) values for each experiment.

As shown in FIG. 13, significant expression levels of IFN-γ and IL-2 were observed from pCWNVCp-immunized mice, while only background levels were observed from control-immunized mice. On the other hand, the level of IL-4 released from all immunized groups was similar. These results show that DNA vaccination resulted in induction of specific and potent Th1-type cellular immune responses in immunized mice.

Example 9

Figure 14:
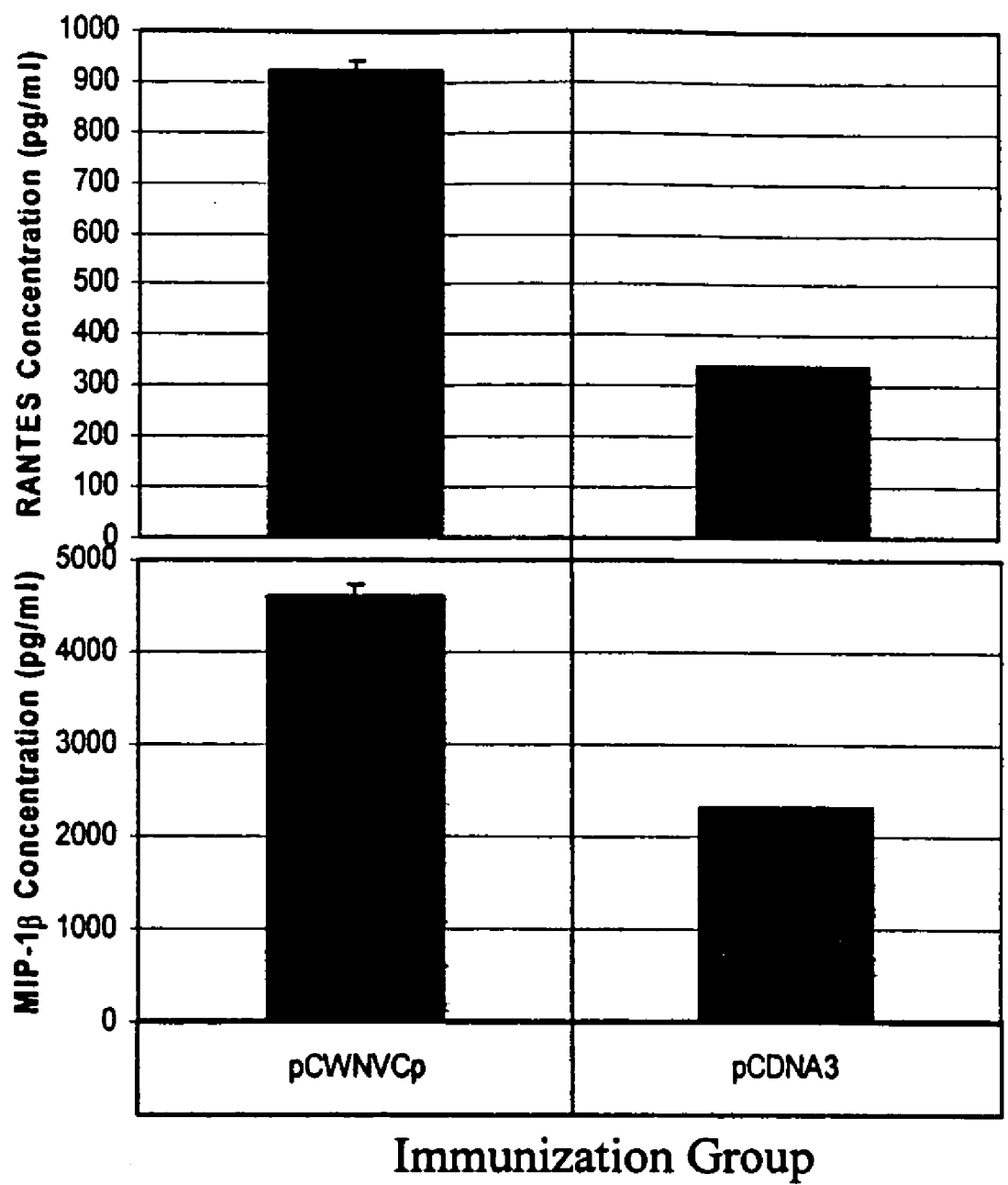
FIG. 14 shows the production of chemokines by stimulated T cells. Mice were immunized and their splenocytes were prepared as described in Example 8. The isolated lymphocytes were stimulated for 3 days with WNV Cp-specific peptide pools. Supernatants were collected and assayed for chemokine profiles using ELISA kits for RANTES and MIP-1β. The error bars represent standard deviation (S.D.) values of each experiment.

Immunization with pCWNVCp Induces Antigen-Specific Production of Chemokines MIP-1β and RANTES The characterization of vaccine-induced cellular immune reponses was extended by examining the expression profiles of β-chemokines (MIP-1 and RANTES) from stimulated T cells. Chemokines are important modulators of immune and inflammatory responses. They are especially important in the molecular regulation of trafficking of leukocytes from the vessels to the peripheral sites of host defense. T cell-produced chemokines have been reported to play a critical role in cellular immune expansion (Kim et al., 1998, J. Clin. Invest., supra; Kim et al., 2000, Macrophage-colony stimulating factor (M-CSF) can modulate immune responses and attract dendritic cells in vivo, Human Gene Therapy, 11:305-321, which is incorporated herein by reference). Therefore, the level of chemokines produced by stimulated T cells may provide additional insight on the level and the quality of antigen-specific cellular immune responses. Supernatant from the T cells stimulated as described in Example 8 was tested for the release of β-chemokines MIP-1β and RANTES using ELISA kits (Biosource, Camarillo, Calif.; R&D Systems, Minneapolis, Minn.). Immunization with pCWNVCp vaccine induced significantly greater levels of expression of MIP-1β and RANTES over those of control vector immunization (FIG. 14). These increased levels of MIP-1β and RANTES from pCWNVCp immunized animals further support the conclusion that pCWNVCp immunization induced the antigen-specific T cell responses observed above.

Example 10

Immunization with pCWNVCp Induces an Antigen-Specific CTL Response

The level of antigen-specific cytotoxic T lymphocyte (CTL) responses following immunization was also examined. A five hour $^{51}Cr$ release bulk CTL assay was performed, as previously described Kim et al., 1997, Nat. Biotechnol., supra, with in vitro stimulation of effector splenocytes prior to measuring chromium release from specific and non-specific peptide treated targets. Effector splenocytes were stimulated in vitro with a pool of WNV Capsid peptides (KGPIRFVL (SEQ ID NO:24), GGPGKSRA (SEQ ID NO:25), and IAPTRAVL (SEQ ID NO:26)) at a concentration of 10 µg/ml for five days in CTL culture media at $5 \times 10^6$ cells/ml. CTL culture media consists of RPMI 1640 (Gibco-BRL, Grand Island, N.Y.), 10% fetal calf serum (Gibco-BRL) and 10% RAT-T-STIM without Con A (Becton Dickinson Labware, Bedford, Mass.). Peptide treated targets were prepared by incubating P815 mouse mastocytoma cells (ATCC, Manassas, Va.) with 10 µg/ml concentration of the peptide pool. The target cells were labeled with 100 µCi/ml $Na_2^{51}CrO_4$ for 120 minutes and incubated with the stimulated effector splenocytes for six hours at 37° C. CTL lysis was determined at 100:1 and 50:1 effector:target (E:T) ratios. Percent specific lysis was determined from the formula:

100×(experimental release−spontaneous release)/ (maximum release−spontaneous release)

Figure 15A:
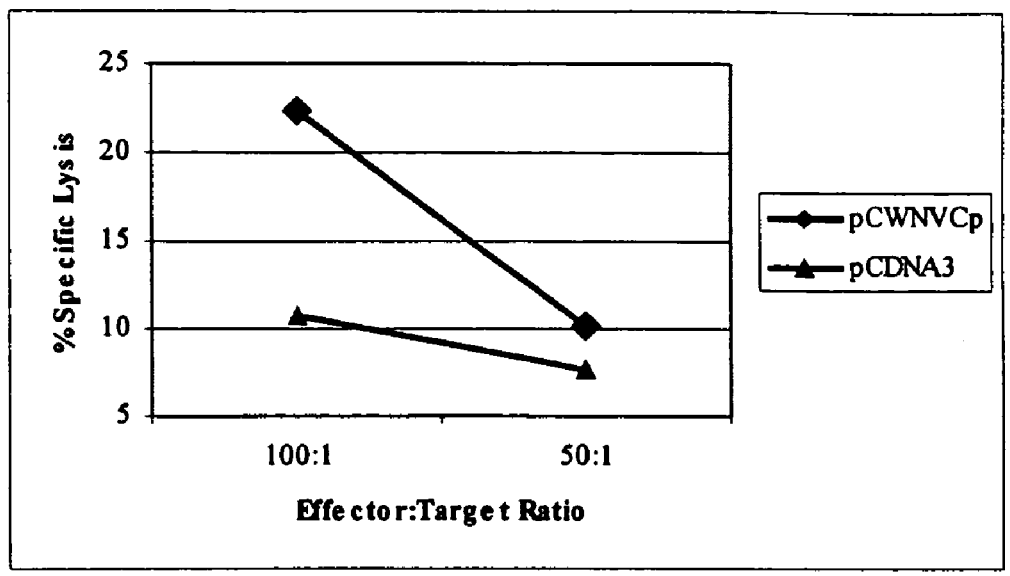
FIG. 15A and FIG. 15B show the induction of positive antigen-specific CTL response.
Figure 15B:
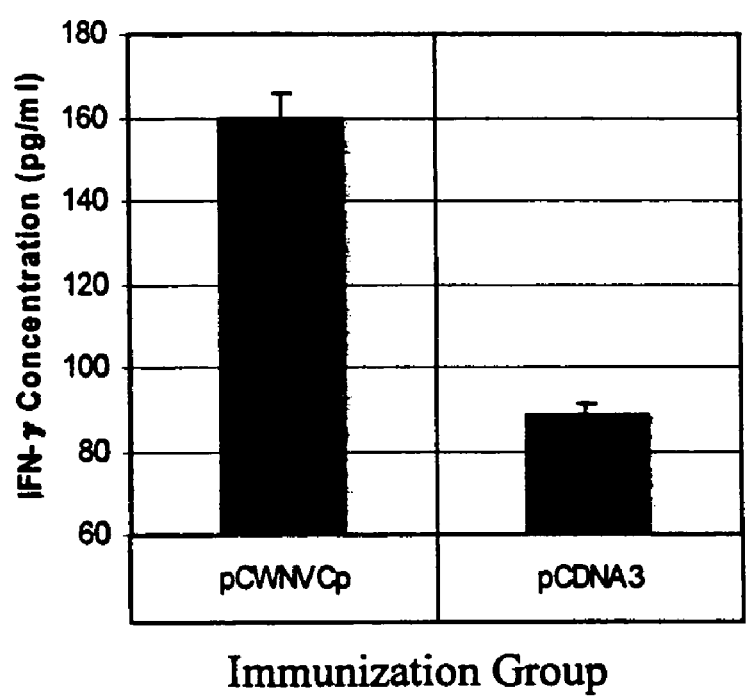

Maximum release was determined by lysis of target cells in 1% Triton X-100 containing medium. An assay was not considered valid if the value for the 'spontaneous release' counts were in excess of 20% of the 'maximum release.' A background level of specific killing was observed from the control animals immunized with pcDNA3. However, the animals immunized with pCWNVCp showed positive CTL activities at 100:1 and 50:1 effector to target (E:T) ratios (FIG. 15A). In addition, an analysis of the supernatant from the in vitro stimulated effector cells for the CTL assay demonstrated an increased level of IFN-γ production from pCWNCp-immunized mice (FIG. 15B).

Example 11

Immunization with pCWNVCp Induces Infiltration of Lymphocytes into the Muscle of Immunized Animals The magnitude of vaccine-induced cell-mediated immune responses in HIV and HSV DNA immunization models has been found to correlate well with the level of cellular infiltration at the site of vaccine injection (Kim et al., 2000, Human Gene Therapy, supra; Chattergoon et al., 2000, Targeted antigen delivery to antigen-presenting cells including dendritic cells by engineered Fas-mediated apoptosis, Nat. Biotechnol., 18:974-979, which is incorporated herein by reference; Agadjanyan et al., 1999, CD86 (B7-2) can function to drive MHC-restricted antigen-specific cytotoxic T lymphocyte responses in vivo., J. Immunol., 162:3417-3427, which is incorporated herein by reference). To further investigate the potency of immune activation induced by pCWNVCp immunization, the muscle tissues of immunized mice were examined immunohistochemically at the site of injection.

Figure 16A:
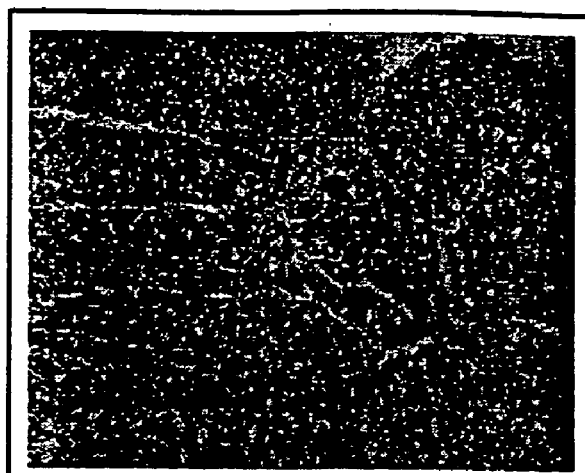
FIGS. 16A, 16B, and 16C show the analyses of muscle tissue. Frozen muscle sections were prepared from DNA injected animals and stained with hematoxylin and eosin (H&E) stain. Slides from pcDNA3 (control) immunized mice (FIG. 16A) and pCWNVCp immunized mice (FIG. 16B) are shown. The panels shown are at 40× magnification.
Figure 16B:
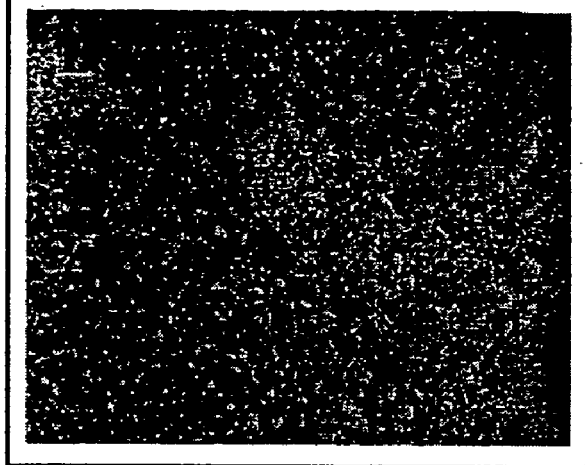

Six- to eight-week-old female Balb/c mice (Charles River Laboratories, Inc., Wilmington, Mass.) were injected intramuscularly (into the tibialis muscle) with 100 μg of pCWNVCp or pcDNA3 in phosphate buffered saline (PBS) and 0.25% bupivacaine-HCl (Sigma, St. Louis, Mo.). After 48 hr of transfection, the tibialis muscle was harvested. The fresh muscle tissue was then frozen in O.C.T. compound (Sakura Finetek USA, Inc., Torrance, Calif.). Four micron frozen sections were made using a Leica 1800 cryostat (Leica Inc., Deerfield, Ill.). To detect the presence of lymphocytes in muscle, the slides were stained with hematoxylin and eosin (H&E) stain (Vector Labs). The slides were viewed with a Nikon OPTIPHOT fluorescence microscope (Nikon Inc., Tokyo, Japan) using a 40× objective (Nikon Fluo 40X Ph3D2). Slide photographs were obtained using Nikon camera FX35DX with exposure control by Nikon UFX-II and Kodak Ektachrome 160T slide film. A dramatic infiltration of immune cells into the muscle of mice immunized with pCWNVCp is shown in FIG. 16B.

Figure 16C:
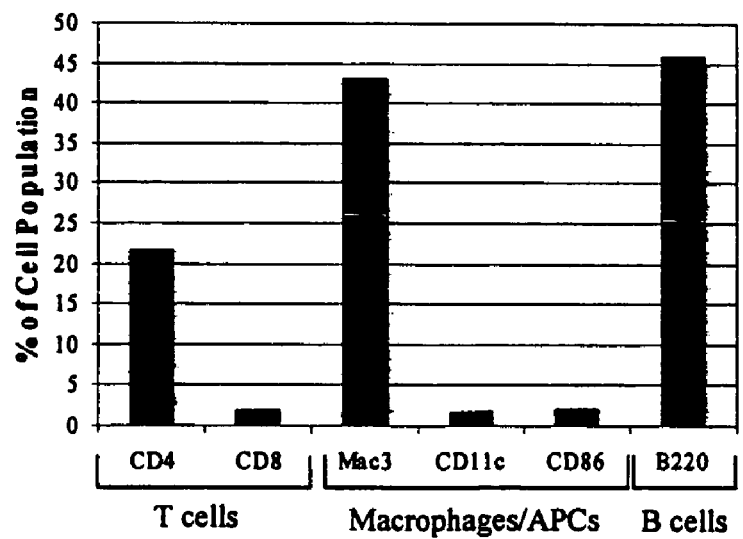

The infiltrating cells were characterized by FACS analysis. The infiltrating cells were harvested from muscle by dissecting out the whole leg muscle and mincing with mechanical force as previously described in Kim et al., 2000, Human Gene Therapy, supra. The cells were recovered by filtering them through a funnel with a glass wool plug. The infiltrating cells were identified by FACS using antibodies to CD4, CD8, Mac-3, CD11c, CD86, and B220 (Pharmingen) as previously described in Kim et al., 2000, Human Gene Therapy, supra and Chattergoon et al., 1990, J. Immunol., 160:5707-5718, which is incorporated herein by reference. Samples were analyzed using a Coulter EPICS®XL-MCL flow cytometer. The infiltrating cells from the mice immunized with pCWNVCp included T cells (both CD4+ and CD8+) and macrophages (detected with anti-Mac3 antibodies) (FIG. 16C). The high levels of CD4+ and CD8+ T cells in the immunized muscle provides further evidence of a high level of T cell activation. On the other hand, the muscle section extracted from the mice immunized with pcDNA3 (control) did not show any sign of cellular infiltration. Taken together, these results demonstrate that antigen-specific immune responses can be efficiently generated via DNA vaccination.

Example 12

Alignment of WNV Capsid Protein with Other *Flavivirus* Capsid Proteins

FIG. 17 shows the alignment of WNV Cp protein with portions of capsid proteins from other *Flaviviruses*, including Kunjin virus (KJV), Japanese ecephalitis virus (JEV), and dengue virus (DEN2), indicating that there is a high degree of identity among these proteins.

Example 13

WNV Cp Protein Induces Apoptosis In Vivo and In Vitro Through the Mitochondrial Pathway The West Nile virus Cp protein, in the absence of other WNV gene products induces rapid nuclear condensation and cell death in tissue culture. Apoptosis is induced through the mitochondrial pathway, as the observed changes in mitochodrial membrane potential were accompanied by Caspase 9 activation and downstream Caspase 3 activation. Moreover, the apoptosis determinant domain was identified to reside in the 3' terminus of the WNV Cp protein by deletion mutation analysis. Following intramuscular injection of a WNV Cp expression cassette, apoptosis in muscle tissue was clearly observed. Most importantly, WNV Cp gene delivery into the striatum of mouse brain resulted in cell death through capsid induced apoptosis in vivo. These studies suggest that the capsid protein of the WNV is responsible for aspects of viral pathogenesis through induction of the apoptotic cascade, supporting the idea that inhibiting this apoptotic function can be exploited as a viable therapeutic approach for the treatment of WNV infection. Additionally, there is sequence identity/homology between the WNV capsid protein and a known apoptosis-inducing region of the HIV-1 vpr gene product (Ayyavoo et al., 1997, Nat. Med., 3:1117-1123; Stewart et al., 1997, J. Virol., 71:5579-5592, each of which is incorporated by reference) (FIGS. 18 and 19).

Example 14

Comparison of WNV Cp and HIV Vpr with the Proteins of Other Apoptosis-Associated Viruses A Medline search for the terms "apoptosis," "encephalitis," and "meningitis" yielded a list of various viruses identified with such symptoms in infected individuals. The amino acid sequences of the proteins of these viruses were compared with the amino acid sequence for WNV capsid protein or HIV-1 89.6 Vpr protein.

Alignments with WNV Capsid Protein (FIG. 19)
1. HIV-1—The WNV capsid protein and the HIV-1 Vpr, a known apoptosis-inducing protein, share sequence homology.
2. Herpes Simplex Virus (HSV)—Sequence alignment of the major capsid protein of the HSV with the WNV Cp indicated possible apoptotic inducing capabilities. Interestingly, destruction via encephalitis has been implicated to correlate with the outcome of the disease.
3. Ebola Virus is a member of the *Filovirus* genus within the Filoviridae family. This pathogen has been implicated with inducing hemorrhagic fever. The alignment of WNV capsid protein and the Ebola nucleocapsid protein indicated detectable amino acid homology within the WNV and nef apoptosis domains. The glycoprotein alignment with the WNV capsid protein also displayed pro-apoptotic domain homology.
4. Rubella Virus is a member of the Togaviridae family, and has been implicated in inducing apoptosis from an in vitro standpoint. Sequence alignment of the Rubella virus capsid protein indicated homology with the WNV capsid protein, as well as with HIV-1 Vpr protein (see FIG. 19), and Tat proteins (data not shown) within the apoptotic domains.

Alignment with HIV-1 89.6 Vpr (FIG. 19)
1. Sindbis Virus—Published data report the apoptotic nature of the Sindbis Virus, especially leading to neuronal cell death. Alignment of the p230 nonstructural protein of Sindbis Virus with HIV-1 Vpr protein (and with Tat protein (data not shown)), indicated isolated homology within the Bcl-2 associated apoptotic regions. Interestingly, recently published data implicated inhibition of Sindbis apoptosis via Bax.

2. Cucumber Mosaic Virus—Previously published reports have implicated cucumber mosaic virus in inducing profound cell killing by necrosis. However, recent data have indicated apoptotic characteristics associated with cell death within tomatoes. Interestingly, our sequence alignment with the vpr 89.6 with the CMV 2A protein also displayed apoptotic domain homology. Comparison with the Tat HIV gene also gave pro-apoptotic homology with the CMV capsid protein.
3. HTLV—Comparisons of this virus with the Tat protein of HIV-1 provided possible insights in apoptotic inducing capability of this virus. Sequence alignment of Tat with the HTLV-1 p27 protein exhibited sequence homology within an apoptotic domain.
4. Nipah Virus—This virus is a member of the Paramyxoviridae family and can be highly lethal in humans. A recent outbreak was observed in Singapore, thus increasing the possibilities of transference into the United States. In addition, the virus seems to have similar clinical outcomes to the West Nile Virus and to other viruses that target the cerebrospinal fluid and cause neural encephalitis. A comparison of the fusion protein of Nipah virus with HIV 89.6 Vpr protein gave an interesting correlation. Strong homology was seen in a cell cycle arrest domain within the Nipah fusion protein. This surface protein could be a strong DNA vaccine candidate; the implications are that it plays a crucial role in the development of apoptosis and cell cycle arrest.
5. Reovirus—Reovirus induces TRAIL-dependent apoptosis in neuronal cells and cell cycle arrest in G2/M phase. Homology was identified between a portion of the core-minor form Mu2 protein of reovirus and HIV 89.6 Vpr protein.

The foregoing examples are meant to illustrate the invention and are not to be construed to limit the invention in any way. Those skilled in the art will recognize modifications that are within the spirit and scope of the invention.

All references cited herein are hereby incorporated by reference in their entirety.

The invention claimed is:

1. A method of inducing cell death comprising the step of contacting a cell with an amount of an isolated West Nile virus (WNV) capsid protein, or a functional fragment thereof, effective to induce cell death, wherein the functional fragment comprises SEQ ID NO:8.

2. The method of claim 1, wherein the cell is a tumor cell.

3. The method of claim 1, wherein the cell is contacted with the West Nile virus (WNV) capsid protein.

* * * * *

SEQUENCE LISTING

<160> NUMBER OF SEQ ID NOS: 73

<210> SEQ ID NO 1
<211> LENGTH: 5864
<212> TYPE: DNA
<213> ORGANISM: Artificial Sequence
<220> FEATURE:
<223> OTHER INFORMATION: Plasmid

<400> SEQUENCE: 1

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagt     900
taagcttgcc gccaccatgg actggacctg atcctgttc ctggtggccg ccgccacccg     960
cgtgcacagc tctaagaaac caggaggccc cggcaagagc cgcgccgtga acatgctgaa    1020
gcgcggcatg cccgcgtgc tgagcctgat tggcctgaag cgcgccatgc tgagcctgat    1080
cgacggcaag ggccccatac gcttcgtgct ggccctgctg gccttcttcc gcttcaccgc    1140
cattgccccc acccgcgccg tgctggaccg ctggcgcggc gtgaacaagc agaccgccat    1200
```

-continued

```
gaagcacctg ctgagcttca agaaggagct gggcaccctg accagcgcca tcaaccgccg   1260
cagcagcaag cagaagaagc gcggcggcaa gaccggcatt gccgtgatga ttggcctgat   1320
cgccagcgtg ggcgcggccg ctcgaggtca cccattcgaa ggtaagccta tccctaaccc   1380
tctcctcggt ctcgattcta cgcgtaccgg tcatcatcac catcaccatt gagtttaaac   1440
ccgctgatca gcctcgactg tgccttctag ttgccagcca tctgttgttt gcccctcccc   1500
cgtgccttcc ttgaccctgg aaggtgccac tcccactgtc ctttcctaat aaaatgagga   1560
aattgcatcg cattgtctga gtaggtgtca ttctattctg gggggtgggg tgggcagga    1620 cagcaagggg gaggattggg aagacaatag caggcatgct ggggatgcgg tgggctctat   1680
ggcttctgag gcgaaagaa ccagctgggg ctctaggggg tatccccacg cgccctgtag    1740
cggcgcatta agcgcggcgg gtgtggtggt tacgcgcagc gtgaccgcta cacttgccag   1800
cgccctagcg cccgctcctt tcgctttctt cccttccttt ctcgccacgt tcgccggctt   1860
tccccgtcaa gctctaaatc ggggcatccc tttagggttc cgatttagtg ctttacggca   1920
cctcgacccc aaaaaacttg attagggtga tggttcacgt agtgggccat cgccctgata   1980
gacggttttt cgccctttga cgttggagtc cacgttcttt aatagtggac tcttgttcca   2040
aactggaaca acactcaacc ctatctcggt ctattctttt gatttataag gattttggg    2100 gatttcggcc tattggttaa aaatgagct gatttaacaa aaatttaacg cgaattaatt    2160
ctgtggaatg tgtgtcagtt agggtgtgga aagtccccag gctccccagg caggcagaag   2220
tatgcaaagc atgcatctca attagtcagc aaccaggtgt ggaaagtccc caggctcccc   2280
agcaggcaga gtatgcaaa gcatgcatct caattagtca gcaaccatag tcccgcccct    2340
aactccgccc atcccgcccc taactccgcc cagttccgcc cattctccgc ccatggctg    2400 actaatttt tttatttatg cagaggccga ggccgcctct gcctctgagc tattccagaa    2460
gtagtgagga ggcttttttg gaggcctagg cttttgcaaa aagctcccgg gagcttgtat   2520
atccattttc ggatctgatc aagagacagg atgaggatcg tttcgcatga ttgaacaaga   2580
tggattgcac gcaggttctc cggccgcttg ggtggagagg ctattcggct atgactgggc   2640
acaacagaca atcggctgct ctgatgccgc cgtgttccgg ctgtcagcgc aggggcgccc   2700 ggttctttt gtcaagaccg acctgtccgg tgccctgaat gaactgcagg acgaggcagc    2760
gcggctatcg tggctggcca cgacgggcgt tccttgcgca gctgtgctcg acgttgtcac   2820
tgaagcggga agggactggc tgctattggg cgaagtgccg gggcaggatc tcctgtcatc   2880
tcaccttgct cctgccgaga agtatccat catggctgat gcaatgcggc ggctgcatac    2940
gcttgatccg gctacctgcc cattcgacca ccaagcgaaa catcgcatcg agcgagcacg   3000
tactcggatg gaagccggtc ttgtcgatca ggatgatctg gacgaagagc atcaggggct   3060
cgcgccagcc gaactgttcg ccaggctcaa ggcgcgcatg cccgacggcg aggatctcgt   3120
cgtgacccat ggcgatgcct gcttgccgaa tatcatggtg aaaatggcc gcttttctgg    3180 attcatcgac tgtggccggc tgggtgtggc ggaccgctat caggacatag cgttggctac   3240
ccgtgatatt gctgaagagc ttggcggcga atgggctgac cgcttcctcg tgctttacgg   3300
tatcgccgct cccgattcgc agcgcatcgc cttctatcgc cttcttgacg agttcttctg   3360
agcgggactc tggggttcgc gaaatgaccg accaagcgac gcccaacctg ccatcacgag   3420
atttcgattc caccgccgcc ttctatgaaa ggttgggctt cggaatcgtt ttccgggacg   3480
ccggctggat gatcctccag cgcggggatc tcatgctgga gttcttcgcc caccccaact   3540
```

```
tgtttattgc agcttataat ggttacaaat aaagcaatag catcacaaat ttcacaaata    3600
aagcattttt ttcactgcat tctagttgtg gtttgtccaa actcatcaat gtatcttatc    3660
atgtctgtat accgtcgacc tctagctaga gcttggcgta atcatggtca tagctgtttc    3720
ctgtgtgaaa ttgttatccg ctcacaattc cacacaacat acgagccgga agcataaagt    3780
gtaaagcctg gggtgcctaa tgagtgagct aactcacatt aattgcgttg cgctcactgc    3840
ccgctttcca gtcgggaaac ctgtcgtgcc agctgcatta atgaatcggc caacgcgcgg    3900
ggagaggcgg tttgcgtatt gggcgctctt ccgcttcctc gctcactgac tcgctgcgct    3960
cggtcgttcg gctgcggcga gcggtatcag ctcactcaaa ggcggtaata cggttatcca    4020
cagaatcagg ggataacgca ggaaagaaca tgtgagcaaa aggccagcaa aaggccagga    4080
accgtaaaaa ggccgcgttg ctggcgtttt tccataggct ccgcccccct gacgagcatc    4140
acaaaaatcg acgctcaagt cagaggtggc gaaacccgac aggactataa agataccagg    4200
cgtttccccc tggaagctcc ctcgtgcgct ctcctgttcc gaccctgccg cttaccggat    4260
acctgtccgc ctttctccct tcgggaagcg tggcgctttc tcaatgctca cgctgtaggt    4320
atctcagttc ggtgtaggtc gttcgctcca agctgggctg tgtgcacgaa ccccccgttc    4380
agcccgaccg ctgcgcctta tccggtaact atcgtcttga gtccaacccg gtaagacacg    4440
acttatcgcc actggcagca gccactggta acaggattag cagagcgagg tatgtaggcg    4500
gtgctacaga gttcttgaag tggtggccta actacggcta cactagaagg acagtatttg    4560
gtatctgcgc tctgctgaag ccagttacct tcggaaaaag agttggtagc tcttgatccg    4620
gcaaacaaac caccgctggt agcggtggtt tttttgtttg caagcagcag attacgcgca    4680
gaaaaaaagg atctcaagaa gatcctttga tcttttctac ggggtctgac gctcagtgga    4740
acgaaaactc acgttaaggg attttggtca tgagattatc aaaaaggatc ttcacctaga    4800
tccttttaaa ttaaaaatga agttttaaat caatctaaag tatatatgag taaacttggt    4860
ctgacagtta ccaatgctta atcagtgagg cacctatctc agcgatctgt ctatttcgtt    4920
catccatagt tgcctgactc cccgtcgtgt agataactac gatacgggag ggcttaccat    4980
ctggccccag tgctgcaatg ataccgcgag acccacgctc accggctcca gatttatcag    5040
caataaacca gccagccgga agggccgagc gcagaagtgg tcctgcaact ttatccgcct    5100
ccatccagtc tattaattgt tgccgggaag ctagagtaag tagttcgcca gttaatagtt    5160
tgcgcaacgt tgttgccatt gctacaggca tcgtggtgtc acgctcgtcg tttggtatgg    5220
cttcattcag ctccggttcc caacgatcaa ggcgagttac atgatccccc atgttgtgca    5280
aaaaagcggt tagctccttc ggtcctccga tcgttgtcag aagtaagttg gccgcagtgt    5340
tatcactcat ggttatggca gcactgcata attctcttac tgtcatgcca tccgtaagat    5400
gcttttctgt gactggtgag tactcaacca agtcattctg agaatagtgt atgcggcgac    5460
cgagttgctc ttgcccggcg tcaatacggg ataataccgc gccacatagc agaactttaa    5520
aagtgctcat cattggaaaa cgttcttcgg ggcgaaaact ctcaaggatc ttaccgctgt    5580
tgagatccag ttcgatgtaa cccactcgtg cacccaactg atcttcagca tcttttactt    5640
tcaccagcgt ttctgggtga gcaaaaacag gaaggcaaaa tgccgcaaaa aagggaataa    5700
gggcgacacg gaaatgttga atactcatac tcttcctttt tcaatattat tgaagcattt    5760
atcagggtta ttgtctcatg agcggataca tatttgaatg tatttagaaa aataaacaaa    5820 tagggggttcc gcgcacattt ccccgaaaag tgccacctga cgtc                   5864
```

-continued

<210> SEQ ID NO 2
<211> LENGTH: 18
<212> TYPE: PRT
<213> ORGANISM: Artificial Sequence
<220> FEATURE:
<223> OTHER INFORMATION: Novel Sequence

<400> SEQUENCE: 2

Met Asp Trp Thr Trp Ile Leu Phe Leu Val Ala Ala Thr Arg Val
1               5                   10                  15

His Ser

<210> SEQ ID NO 3
<211> LENGTH: 122
<212> TYPE: PRT
<213> ORGANISM: Artificial Sequence
<220> FEATURE:
<223> OTHER INFORMATION: Novel Sequence

<400> SEQUENCE: 3

Ser Lys Lys Pro Gly Gly Pro Gly Lys Ser Arg Ala Val Asn Met Leu
1               5                   10                  15

Lys Arg Gly Met Pro Arg Val Leu Ser Leu Ile Gly Leu Lys Arg Ala
                20                  25                  30

Met Leu Ser Leu Ile Asp Gly Lys Gly Pro Ile Arg Phe Val Leu Ala
            35                  40                  45

Leu Leu Ala Phe Phe Arg Phe Thr Ala Ile Ala Pro Thr Arg Ala Val
        50                  55                  60

Leu Asp Arg Trp Arg Gly Val Asn Lys Gln Thr Ala Met Lys His Leu
65                  70                  75                  80

Leu Ser Phe Lys Lys Glu Leu Gly Thr Leu Thr Ser Ala Ile Asn Arg
                85                  90                  95

Arg Ser Ser Lys Gln Lys Lys Arg Gly Gly Lys Thr Gly Ile Ala Val
                100                 105                 110

Met Ile Gly Leu Ile Ala Ser Val Gly Ala
            115                 120

<210> SEQ ID NO 4
<211> LENGTH: 5864
<212> TYPE: DNA
<213> ORGANISM: Artificial Sequence
<220> FEATURE:
<223> OTHER INFORMATION: Plasmid

<400> SEQUENCE: 4
gacggatcgg gagatctccc gatccctat ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660

```
actcacgggg atttccaagt ctccacccca ttgacgtcaa tgggagtttg ttttggcacc     720
aaaatcaacg gactttccaa aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagt     900
taagcttgcc gccaccatgg attggacttg gatcttattt ttagttgctg ctgctactag     960
agttcattct tctaaaaaac caggtggccc cggcaagagc cgcgccgtga acatgctgaa    1020
gcgcggcatg ccccgcgtgc tgagcctgat tggcctgaag cgcgccatgc tgagcctgat    1080
cgacggcaag ggccccatac gcttcgtgct ggccctgctg gccttcttcc gcttcaccgc    1140
cattgccccc acccgcgccg tgctggaccg ctggcgcggc gtgaacaagc agaccgccat    1200
gaagcacctg ctgagcttca agaaggagct gggcaccctg accagcgcca tcaaccgccg    1260
cagcagcaag cagaagaagc gcggcggcaa gaccggcatt gccgtgatga ttggcctgat    1320
cgccagcgtg ggcgcggccg ctcgaggtca cccattcgaa ggtaagccta tccctaaccc    1380
tctcctcggt ctcgattcta cgcgtaccgg tcatcatcac catcaccatt gagtttaaac    1440
ccgctgatca gcctcgactg tgccttctag ttgccagcca tctgttgttt gcccctcccc    1500
cgtgccttcc ttgaccctgg aaggtgccac tcccactgtc cttcctaat aaaatgagga    1560 aattgcatcg cattgtctga gtaggtgtca ttctattctg gggggtgggg tggggcagga    1620
cagcaagggg gaggattggg aagacaatag caggcatgct ggggatgcgg tgggctctat    1680
ggcttctgag gcggaaagaa ccagctgggg ctctagggg tatccccacg cgccctgtag    1740
cggcgcatta gcgcggcgg gtgtggtggt tacgcgcagc gtgaccgcta cacttgccag    1800
cgccctagcg cccgctcctt tcgctttctt cccttccttt ctcgccacgt tcgccggctt    1860
tccccgtcaa gctctaaatc ggggcatccc tttagggttc cgatttagtg ctttacggca    1920
cctcgacccc aaaaaacttg attagggtga tggttcacgt agtgggccat cgccctgata    1980
gacggttttt cgccctttga cgttggagtc cacgttcttt aatagtggac tcttgttcca    2040
aactggaaca cactcaacc ctatctcggt ctattctttt gatttataag ggattttggg    2100
gatttcggcc tattggttaa aaaatgagct gatttaacaa aaatttaacg cgaattaatt    2160
ctgtggaatg tgtgtcagtt agggtgtgga aagtccccag gctccccagg caggcagaag    2220
tatgcaaagc atgcatctca attagtcagc aaccaggtgt ggaaagtccc caggctcccc    2280
agcaggcaga agtatgcaaa gcatgcatct caattagtca gcaaccatag tcccgcccct    2340
aactccgccc atcccgcccc taactccgcc cagttccgcc cattctccgc cccatggctg    2400
actaattttt tttatttatg cagaggccga ggccgcctct gcctctgagc tattccagaa    2460
gtagtgagga ggcttttttg gaggcctagg cttttgcaaa aagctcccgg gagcttgtat    2520
atccattttc ggatctgatc aagagacagg atgaggatc tttcgcatga ttgaacaaga    2580
tggattgcac gcaggttctc cggccgcttg ggtggagagg ctattcggct atgactgggc    2640
acaacagaca atcggctgct ctgatgccgc cgtgttccgg ctgtcagcgc aggggcgccc    2700
ggttcttttt gtcaagaccg acctgtccgg tgccctgaat gaactgcagg acgaggcagc    2760
gcggctatcg tggctggcca cgacgggcgt tccttgcgca gctgtgctcg acgttgtcac    2820
tgaagcggga agggactggc tgctattggg cgaagtgccg gggcaggatc tcctgtcatc    2880
tcaccttgct cctgccgaga aagtatccat catggctgat gcaatgcggc ggctgcatac    2940
gcttgatccg gctacctgcc cattcgacca ccaagcgaaa catcgcatcg agcgagcacg    3000
```

```
tactcggatg aagccggtc ttgtcgatca ggatgatctg gacgaagagc atcaggggct    3060
cgcgccagcc gaactgttcg ccaggctcaa ggcgcgcatg cccgacggcg aggatctcgt    3120
cgtgacccat ggcgatgcct gcttgccgaa tatcatggtg aaaatggcc gcttttctgg    3180
attcatcgac tgtggccggc tgggtgtggc ggaccgctat caggacatag cgttggctac    3240
ccgtgatatt gctgaagagc ttggcggcga atgggctgac cgcttcctcg tgctttacgg    3300
tatcgccgct cccgattcgc agcgcatcgc cttctatcgc cttcttgacg agttcttctg    3360
agcgggactc tggggttcgc gaaatgaccg accaagcgac gcccaacctg ccatcacgag    3420
atttcgattc caccgccgcc ttctatgaaa ggttgggctt cggaatcgtt ttccgggacg    3480
ccggctggat gatcctccag cgcggggatc tcatgctgga gttcttcgcc acccccaact    3540
tgtttattgc agcttataat ggttacaaat aaagcaatag catcacaaat ttcacaaata    3600
aagcattttt ttcactgcat tctagttgtg gtttgtccaa actcatcaat gtatcttatc    3660
atgtctgtat accgtcgacc tctagctaga gcttggcgta atcatggtca tagctgtttc    3720
ctgtgtgaaa ttgttatccg ctcacaattc cacacaacat acgagccgga agcataaagt    3780
gtaaagcctg gggtgcctaa tgagtgagct aactcacatt aattgcgttg cgctcactgc    3840
ccgctttcca gtcgggaaac ctgtcgtgcc agctgcatta atgaatcggc caacgcgcgg    3900
ggagaggcgg tttgcgtatt gggcgctctt ccgcttcctc gctcactgac tcgctgcgct    3960
cggtcgttcg gctgcggcga gcggtatcag ctcactcaaa ggcggtaata cggttatcca    4020
cagaatcagg ggataacgca ggaaagaaca tgtgagcaaa aggccagcaa aaggccagga    4080
accgtaaaaa ggccgcgttg ctggcgtttt tccataggct ccgcccccct gacgagcatc    4140
acaaaaatcg acgctcaagt cagaggtggc gaaacccgac aggactataa agataccagg    4200
cgtttccccc tggaagctcc ctcgtgcgct ctcctgttcc gaccctgccg cttaccggat    4260
acctgtccgc ctttctccct cgggaagcg tggcgctttc tcaatgctca cgctgtaggt    4320
atctcagttc ggtgtaggtc gttcgctcca agctgggctg tgtgcacgaa ccccccgttc    4380
agcccgaccg ctgcgcctta tccggtaact atcgtcttga gtccaacccg gtaagcacg    4440
acttatcgcc actggcagca gccactggta acaggattag cagagcgagg tatgtaggcg    4500
gtgctacaga gttcttgaag tggtggccta actacggcta cactagaagg acagtatttg    4560
gtatctgcgc tctgctgaag ccagttacct tcggaaaaag agttggtagc tcttgatccg    4620
gcaaacaaac caccgctggt agcggtggtt tttttgtttg caagcagcag attacgcgca    4680
gaaaaaaagg atctcaagaa gatcctttga tcttttctac ggggtctgac gctcagtgga    4740
acgaaaactc acgttaaggg attttggtca tgagattatc aaaaaggatc ttcacctaga    4800
tccttttaaa ttaaaaatga agttttaaat caatctaaag tatatatgag taaacttggt    4860
ctgacagtta ccaatgctta atcagtgagg cacctatctc agcgatctgt ctatttcgtt    4920
catccatagt tgcctgactc cccgtcgtgt agataactac gatacgggag ggcttaccat    4980
ctggccccag tgctgcaatg ataccgcgag acccacgctc accggctcca gatttatcag    5040
caataaacca gccagccgga agggccgagc gcagaagtgg tcctgcaact ttatccgcct    5100
ccatccagtc tattaattgt tgccgggaag ctagagtaag tagttcgcca gttaatagtt    5160
tgcgcaacgt tgttgccatt gctacaggca tcgtggtgtc acgctcgtcg tttggtatgg    5220
cttcattcag ctccggttcc caacgatcaa ggcgagttac atgatccccc atgttgtgca    5280
aaaaagcggt tagctccttc ggtcctccga tcgttgtcag aagtaagttg gccgcagtgt    5340
tatcactcat ggttatggca gcactgcata attctcttac tgtcatgcca tccgtaagat    5400
```

```
gcttttctgt gactggtgag tactcaacca agtcattctg agaatagtgt atgcggcgac    5460
cgagttgctc ttgcccggcg tcaatacggg ataataccgc gccacatagc agaactttaa    5520
aagtgctcat cattggaaaa cgttcttcgg ggcgaaaact ctcaaggatc ttaccgctgt    5580
tgagatccag ttcgatgtaa cccactcgtg cacccaactg atcttcagca tcttttactt    5640
tcaccagcgt ttctgggtga gcaaaaacag gaaggcaaaa tgccgcaaaa aagggaataa    5700
gggcgacacg gaaatgttga atactcatac tcttcctttt tcaatattat tgaagcattt    5760
atcagggtta ttgtctcatg agcggataca tatttgaatg tatttagaaa aataaacaaa    5820 tagggggttcc gcgcacattt ccccgaaaag tgccacctga cgtc                   5864
```

<210> SEQ ID NO 5
<211> LENGTH: 123
<212> TYPE: PRT
<213> ORGANISM: West Nile virus

<400> SEQUENCE: 5

```
Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala
        115                 120
```

<210> SEQ ID NO 6
<211> LENGTH: 22
<212> TYPE: PRT
<213> ORGANISM: Artificial Sequence
<220> FEATURE:
<223> OTHER INFORMATION: Novel Sequence

<400> SEQUENCE: 6

```
Ser Lys Lys Pro Gly Gly Pro Gly Lys Ser Arg Ala Val Asn Met Leu
1               5                   10                  15

Lys Arg Gly Met Pro Arg
            20
```

<210> SEQ ID NO 7
<211> LENGTH: 19
<212> TYPE: PRT
<213> ORGANISM: Artificial Sequence
<220> FEATURE:
<223> OTHER INFORMATION: Novel Sequence

<400> SEQUENCE: 7

```
Lys Arg Ala Met Leu Ser Leu Ile Asp Gly Lys Gly Pro Ile Arg Phe
1               5                   10                  15

Val Leu Ala
```

```
<210> SEQ ID NO 8
<211> LENGTH: 22
<212> TYPE: PRT
<213> ORGANISM: Artificial Sequence
<220> FEATURE:
<223> OTHER INFORMATION: Novel Sequence

<400> SEQUENCE: 8

Thr Leu Thr Ser Ala Ile Asn Arg Arg Ser Lys Gln Lys Lys Arg
 1               5                  10                  15

Gly Gly Lys Thr Gly Ile
             20

<210> SEQ ID NO 9
<211> LENGTH: 123
<212> TYPE: PRT
<213> ORGANISM: Artificial Sequence
<220> FEATURE:
<223> OTHER INFORMATION: Novel Sequence

<400> SEQUENCE: 9

Met Ser Lys Lys Pro Gly Gly Pro Gly Lys Ser Arg Ala Val Asn Met
 1               5                  10                  15

Leu Lys Arg Gly Met Pro Arg Val Leu Ser Leu Thr Gly Leu Lys Arg
                20                  25                  30

Ala Met Leu Ser Leu Ile Asp Gly Arg Gly Pro Thr Arg Phe Val Leu
            35                  40                  45

Ala Leu Leu Ala Phe Phe Arg Phe Thr Ala Ile Ala Pro Thr Arg Ala
        50                  55                  60

Val Leu Asp Arg Trp Arg Ser Val Asn Lys Gln Thr Ala Met Lys His
 65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Phe Met Ile Gly Leu Ile Ala Gly Val Gly Ala
        115                 120

<210> SEQ ID NO 10
<211> LENGTH: 113
<212> TYPE: PRT
<213> ORGANISM: Artificial Sequence
<220> FEATURE:
<223> OTHER INFORMATION: Novel Sequence

<400> SEQUENCE: 10

Met Thr Lys Lys Pro Gly Gly Pro Gly Lys Asn Arg Ala Ile Asn Met
 1               5                  10                  15

Leu Lys Arg Gly Leu Pro Arg Val Phe Pro Leu Val Gly Val Lys Arg
                20                  25                  30

Val Val Met Ser Leu Leu Asp Gly Arg Gly Pro Val Arg Phe Val Leu
            35                  40                  45

Ala Leu Ile Thr Phe Phe Lys Phe Thr Ala Leu Ala Pro Thr Lys Ala
        50                  55                  60

Leu Leu Gly Arg Trp Lys Ala Val Glu Lys Ser Val Ala Met Lys His
 65                  70                  75                  80

Leu Thr Ser Phe Lys Arg Glu Leu Gly Thr Leu Ile Asp Ala Val Asn
                85                  90                  95
```

```
Lys Arg Gly Arg Lys Gln Asn Lys Arg Gly Asn Glu Gly Ser Ile
            100                 105                 110
Met
```

<210> SEQ ID NO 11
<211> LENGTH: 114
<212> TYPE: PRT
<213> ORGANISM: Artificial Sequence
<220> FEATURE:
<223> OTHER INFORMATION: Novel Sequence

<400> SEQUENCE: 11

```
Met Ser Lys Lys Pro Gly Gly Pro Gly Lys Ser Arg Ala Val Asn Met
1               5                   10                  15
Leu Lys Arg Gly Met Pro Arg Val Leu Ser Leu Ile Gly Leu Lys Arg
            20                  25                  30
Ala Met Leu Ser Leu Ile Asp Gly Lys Gly Pro Ile Arg Phe Val Leu
        35                  40                  45
Ala Leu Leu Ala Phe Phe Arg Phe Thr Ala Ile Ala Pro Thr Arg Ala
    50                  55                  60
Val Leu Asp Arg Trp Arg Gly Val Asn Lys Gln Thr Ala Met Lys His
65                  70                  75                  80
Leu Leu Ser Phe Lys Lys Glu Leu Gly Thr Leu Thr Ser Ala Ile Asn
                85                  90                  95
Arg Arg Ser Ser Lys Gln Lys Lys Arg Gly Gly Lys Thr Gly Ile Ala
            100                 105                 110
Val Met
```

<210> SEQ ID NO 12
<211> LENGTH: 90
<212> TYPE: PRT
<213> ORGANISM: Artificial Sequence
<220> FEATURE:
<223> OTHER INFORMATION: Novel Sequence

<400> SEQUENCE: 12

```
Arg Asn Thr Pro Phe Asn Met Leu Lys Arg Glu Arg Asn Arg Val Ser
1               5                   10                  15
Thr Val Gln Gln Leu Thr Arg Phe Ser Leu Gly Met Leu Gln Lys Gly
            20                  25                  30
Arg Gly Pro Leu Lys Leu Phe Met Ala Leu Val Ala Phe Leu Arg Phe
        35                  40                  45
Leu Thr Ile Pro Pro Thr Ala Gly Ile Leu Lys Arg Trp Gly Thr Ile
    50                  55                  60
Lys Lys Ser Lys Ala Ile Asn Val Leu Arg Gly Phe Lys Lys Glu Ile
65                  70                  75                  80
Gly Arg Met Leu Asn Ile Leu Asn Arg Arg
                85                  90
```

<210> SEQ ID NO 13
<211> LENGTH: 89
<212> TYPE: PRT
<213> ORGANISM: Artificial Sequence
<220> FEATURE:
<223> OTHER INFORMATION: Novel Sequence

<400> SEQUENCE: 13

```
Lys Ser Arg Ala Val Asn Met Leu Lys Arg Gly Met Pro Arg Val Leu
1               5                   10                  15
```

```
Ser Leu Ile Gly Leu Lys Arg Ala Met Leu Ser Leu Ile Asp Gly Lys
         20                  25                  30

Gly Pro Ile Arg Phe Val Leu Ala Leu Leu Ala Phe Phe Arg Phe Thr
             35                  40                  45

Ala Ile Ala Pro Thr Arg Ala Val Leu Asp Arg Trp Arg Gly Val Asn
     50                  55                  60

Lys Gln Thr Ala Met Lys His Leu Leu Ser Phe Lys Lys Glu Leu Gly
 65                  70                  75                  80

Thr Leu Thr Ser Ala Ile Asn Arg Arg
                 85
```

```
<210> SEQ ID NO 14
<211> LENGTH: 90
<212> TYPE: DNA
<213> ORGANISM: Artificial Sequence
<220> FEATURE:
<223> OTHER INFORMATION: Novel Sequence

<400> SEQUENCE: 14
atggactgga cctggatcct gttcctggtg gccgccgcca cccgcgtgca cagctctaag      60
aaaccaggag gccccggcaa gagccgcgcc                                      90

<210> SEQ ID NO 15
<211> LENGTH: 90
<212> TYPE: DNA
<213> ORGANISM: Artificial Sequence
<220> FEATURE:
<223> OTHER INFORMATION: Novel Sequence

<400> SEQUENCE: 15
atggattgga cttggatctt attttagtt gctgctgcta ctagagttca ttcttctaaa       60
aaaccaggtg gccccggcaa gagccgcgcc                                      90

<210> SEQ ID NO 16
<211> LENGTH: 88
<212> TYPE: DNA
<213> ORGANISM: Artificial Sequence
<220> FEATURE:
<223> OTHER INFORMATION: Novel Sequence

<400> SEQUENCE: 16
ggctcagcat ggcgcgcttc aggccaatca ggctcagcac gcggggcatg ccgcgcttca      60
gcatgttcac ggcgcggctc ttgccggg                                        88

<210> SEQ ID NO 17
<211> LENGTH: 90
<212> TYPE: DNA
<213> ORGANISM: Artificial Sequence
<220> FEATURE:
<223> OTHER INFORMATION: Novel Sequence

<400> SEQUENCE: 17
ggcctgaagc gcgccatgct gagcctgatc gacggcaagg gccccatacg cttcgtgctg      60
gccctgctgg ccttcttccg cttcaccgcc                                      90

<210> SEQ ID NO 18
<211> LENGTH: 89
<212> TYPE: DNA
<213> ORGANISM: Artificial Sequence
<220> FEATURE:
<223> OTHER INFORMATION: Novel Sequence
```

```
<400> SEQUENCE: 18
ggtgcttcat ggcggtctgc ttgttcacgc cgcgccagcg gtccagcacg gcgcgggtgg      60
gggcaatggc ggtgaagcgg aagaaggcc                                        89

<210> SEQ ID NO 19
<211> LENGTH: 89
<212> TYPE: DNA
<213> ORGANISM: Artificial Sequence
<220> FEATURE:
<223> OTHER INFORMATION: Novel Sequence

<400> SEQUENCE: 19
ccgccatgaa gcacctgctg agcttcaaga aggagctggg cacectgacc agcgccatca      60 accgccgcag cagcaagcag aagaagcgc                                        89

<210> SEQ ID NO 20
<211> LENGTH: 81
<212> TYPE: DNA
<213> ORGANISM: Artificial Sequence
<220> FEATURE:
<223> OTHER INFORMATION: Novel Sequence

<400> SEQUENCE: 20
cgcgcccacg ctggcgatca ggccaatcat cacggcaatg ccggtcttgc cgccgcgctt      60
cttctgcttg ctgctgcggc g                                                81

<210> SEQ ID NO 21
<211> LENGTH: 39
<212> TYPE: DNA
<213> ORGANISM: Artificial Sequence
<220> FEATURE:
<223> OTHER INFORMATION: Novel Sequence

<400> SEQUENCE: 21
cccaagcttg ccgccaccat ggactggacc tggatcctg                             39

<210> SEQ ID NO 22
<211> LENGTH: 33
<212> TYPE: DNA
<213> ORGANISM: Artificial Sequence
<220> FEATURE:
<223> OTHER INFORMATION: Novel Sequence

<400> SEQUENCE: 22
cccaagcttg ccgccaccat ggattggact tgg                                   33

<210> SEQ ID NO 23
<211> LENGTH: 37
<212> TYPE: DNA
<213> ORGANISM: Artificial Sequence
<220> FEATURE:
<223> OTHER INFORMATION: Novel Sequence

<400> SEQUENCE: 23
atagtttagc ggccgcgccc acgctggcga tcaggcc                               37

<210> SEQ ID NO 24
<211> LENGTH: 8
<212> TYPE: PRT
<213> ORGANISM: Artificial Sequence
<220> FEATURE:
<223> OTHER INFORMATION: Novel Sequence

<400> SEQUENCE: 24
```

```
Lys Gly Pro Ile Arg Phe Val Leu
1               5

<210> SEQ ID NO 25
<211> LENGTH: 8
<212> TYPE: PRT
<213> ORGANISM: Artificial Sequence
<220> FEATURE:
<223> OTHER INFORMATION: Novel Sequence

<400> SEQUENCE: 25

Gly Gly Pro Gly Lys Ser Arg Ala
1               5

<210> SEQ ID NO 26
<211> LENGTH: 8
<212> TYPE: PRT
<213> ORGANISM: Artificial Sequence
<220> FEATURE:
<223> OTHER INFORMATION: Novel Sequence

<400> SEQUENCE: 26

Ile Ala Pro Thr Arg Ala Val Leu
1               5

<210> SEQ ID NO 27
<211> LENGTH: 40
<212> TYPE: PRT
<213> ORGANISM: Artificial Sequence
<220> FEATURE:
<223> OTHER INFORMATION: Novel Sequence

<400> SEQUENCE: 27

Thr Trp Thr Gly Val Glu Ala Leu Ile Arg Ile Leu Gln Gln Leu Leu
1               5                   10                  15

Phe Ile His Phe Arg Ile Gly Cys Arg His Ser Arg Ile Gly Ile Ile
            20                  25                  30

Gln Gln Arg Arg Thr Arg Asn Gly
        35                  40

<210> SEQ ID NO 28
<211> LENGTH: 43
<212> TYPE: PRT
<213> ORGANISM: Artificial Sequence
<220> FEATURE:
<223> OTHER INFORMATION: Novel Sequence

<400> SEQUENCE: 28

Arg Trp Arg Gly Val Asn Lys Gln Thr Ala Met Lys His Leu Leu Ser
1               5                   10                  15

Phe Lys Lys Glu Leu Gly Thr Leu Thr Ser Ala Ile Asn Arg Arg Ser
            20                  25                  30

Ser Lys Gln Lys Lys Arg Gly Gly Lys Thr Gly
        35                  40

<210> SEQ ID NO 29
<211> LENGTH: 106
<212> TYPE: PRT
<213> ORGANISM: Artificial Sequence
<220> FEATURE:
<223> OTHER INFORMATION: Novel Sequence

<400> SEQUENCE: 29

Ala Val Lys Thr Val Ala Ser Ala Leu Gln Phe Gly Val Asp Ala Leu
```

```
                1               5                   10                  15
Glu Arg Gly Leu Ile Asn Thr Val Leu Ser Val Lys Leu Arg His Ala
                20                  25                  30

Pro Pro Met Phe Ile Leu Gln Thr Leu Ala Asp Pro Thr Phe Thr Glu
                35                  40                  45

Arg Gly Phe Ser Lys Thr Val Lys Ser Asp Leu Ile Ala Met Phe Lys
        50                  55                  60

Arg His Leu Leu Glu His Ser Phe Phe Leu Asp Arg Ala Glu Asn Met
65                  70                  75                  80

Gly Ser Gly Phe Ser Gln Tyr Ser Arg Leu Ser Glu Met Val Ala Ala
                85                  90                  95

Val Ser Gly Glu Ser Val Leu Lys Gly Val
            100                 105

<210> SEQ ID NO 30
<211> LENGTH: 110
<212> TYPE: PRT
<213> ORGANISM: Artificial Sequence
<220> FEATURE:
<223> OTHER INFORMATION: Novel Sequence

<400> SEQUENCE: 30

Pro Gly Lys Ser Arg Ala Val Asn Met Leu Lys Arg Gly Met Pro Arg
1               5                   10                  15

Val Leu Ser Leu Ile Gly Leu Lys Arg Ala Met Leu Ser Leu Ile Asp
                20                  25                  30

Gly Lys Gly Pro Ile Arg Phe Val Leu Ala Leu Leu Ala Phe Phe Arg
            35                  40                  45

Phe Thr Ala Ile Ala Pro Thr Arg Ala Val Leu Asp Arg Trp Arg Gly
        50                  55                  60

Val Asn Lys Gln Thr Ala Met Lys His Leu Leu Ser Phe Lys Lys Glu
65                  70                  75                  80

Leu Gly Thr Leu Thr Ser Ala Ile Asn Arg Arg Ser Ser Lys Gln Lys
                85                  90                  95

Lys Arg Gly Gly Lys Thr Gly Ile Ala Val Met Ile Gly Leu
            100                 105                 110

<210> SEQ ID NO 31
<211> LENGTH: 106
<212> TYPE: PRT
<213> ORGANISM: Artificial Sequence
<220> FEATURE:
<223> OTHER INFORMATION: Novel Sequence

<400> SEQUENCE: 31

His Met Met Val Ile Phe Arg Leu Met Arg Thr Asn Phe Leu Ile Lys
1               5                   10                  15

Phe Leu Leu Ile His Gln Gly Met His Met Val Ala Gly His Asp Ala
                20                  25                  30

Asn Asp Ala Val Ile Ser Asn Val Ala Gln Ala Arg Phe Ser Gly Leu
            35                  40                  45

Leu Ile Val Lys Thr Val Leu Asp His Ile Leu Gln Lys Thr Glu Arg
        50                  55                  60

Gly Val Arg Leu His Pro Leu Ala Arg Thr Ala Lys Val Lys Asn Glu
65                  70                  75                  80

Val Asn Ser Phe Lys Ala Ala Leu Ser Ser Leu Ala Lys His Gly Glu
                85                  90                  95
```

```
Tyr Ala Pro Phe Ala Arg Leu Leu Asn Leu
            100                 105

<210> SEQ ID NO 32
<211> LENGTH: 108
<212> TYPE: PRT
<213> ORGANISM: Artificial Sequence
<220> FEATURE:
<223> OTHER INFORMATION: Novel Sequence

<400> SEQUENCE: 32

Lys Ser Arg Ala Val Asn Met Leu Lys Arg Gly Met Pro Arg Val Leu
1               5                   10                  15

Ser Leu Ile Gly Leu Lys Arg Ala Met Leu Ser Leu Ile Asp Gly Lys
            20                  25                  30

Gly Pro Ile Arg Phe Val Leu Ala Leu Leu Ala Phe Phe Arg Phe Thr
        35                  40                  45

Ala Ile Ala Pro Thr Arg Ala Val Leu Asp Arg Trp Arg Gly Val Asn
    50                  55                  60

Lys Gln Thr Ala Met Lys His Leu Leu Ser Phe Lys Lys Glu Leu Gly
65                  70                  75                  80

Thr Leu Thr Ser Ala Ile Asn Arg Arg Ser Lys Gln Lys Lys Arg
                85                  90                  95

Gly Gly Lys Thr Gly Ile Ala Val Met Ile Gly Leu
            100                 105

<210> SEQ ID NO 33
<211> LENGTH: 20
<212> TYPE: PRT
<213> ORGANISM: Artificial Sequence
<220> FEATURE:
<223> OTHER INFORMATION: Novel Sequence

<400> SEQUENCE: 33

Lys Pro Asp Gly Ser Glu Cys Leu Pro Ala Ala Pro Asp Gly Ile Arg
1               5                   10                  15

Gly Phe Pro Arg
            20

<210> SEQ ID NO 34
<211> LENGTH: 20
<212> TYPE: PRT
<213> ORGANISM: Artificial Sequence
<220> FEATURE:
<223> OTHER INFORMATION: Novel Sequence

<400> SEQUENCE: 34

Lys Pro Gly Gly Pro Gly Lys Ser Arg Ala Val Asn Met Leu Lys Arg
1               5                   10                  15

Gly Met Pro Arg
            20

<210> SEQ ID NO 35
<211> LENGTH: 23
<212> TYPE: PRT
<213> ORGANISM: Artificial Sequence
<220> FEATURE:
<223> OTHER INFORMATION: Novel Sequence

<400> SEQUENCE: 35

Leu Gln Leu Phe Leu Arg Ala Thr Thr Glu Leu Arg Thr Phe Ser Ile
1               5                   10                  15
```

```
Leu Asn Arg Lys Ala Ile Asp
            20

<210> SEQ ID NO 36
<211> LENGTH: 24
<212> TYPE: PRT
<213> ORGANISM: Artificial Sequence
<220> FEATURE:
<223> OTHER INFORMATION: Novel Sequence

<400> SEQUENCE: 36

Leu Leu Ala Phe Phe Arg Phe Thr Ala Ile Ala Pro Thr Arg Ala Val
1               5                   10                  15

Leu Asp Arg Trp Arg Gly Val Asn
            20

<210> SEQ ID NO 37
<211> LENGTH: 47
<212> TYPE: PRT
<213> ORGANISM: Artificial Sequence
<220> FEATURE:
<223> OTHER INFORMATION: Novel Sequence

<400> SEQUENCE: 37

Arg Ser Ala Arg His Pro Trp Arg Ile Arg Phe Gly Ala Pro Gln Ala
1               5                   10                  15

Phe Leu Ala Gly Leu Leu Ala Thr Val Ala Val Gly Thr Ala Arg
                20                  25                  30

Ala Gly Leu Gln Pro Arg Ala Asp Met Ala Ala Pro Pro Thr Leu
            35                  40                  45

<210> SEQ ID NO 38
<211> LENGTH: 52
<212> TYPE: PRT
<213> ORGANISM: Artificial Sequence
<220> FEATURE:
<223> OTHER INFORMATION: Novel Sequence

<400> SEQUENCE: 38

Arg Ala Val Leu Asp Arg Trp Arg Gly Val Asn Lys Gln Thr Ala Met
1               5                   10                  15

Lys His Leu Leu Ser Phe Lys Lys Glu Leu Gly Thr Leu Thr Ser Ala
                20                  25                  30

Ile Asn Arg Arg Ser Ser Lys Gln Lys Lys Arg Gly Gly Lys Thr Gly
            35                  40                  45

Ile Ala Val Met
        50

<210> SEQ ID NO 39
<211> LENGTH: 45
<212> TYPE: PRT
<213> ORGANISM: Artificial Sequence
<220> FEATURE:
<223> OTHER INFORMATION: Novel Sequence

<400> SEQUENCE: 39

Leu His His Cys Ile Ala Arg Trp Ile Ala Gln Arg Gly Gly Trp Val
1               5                   10                  15

Ala Ala Leu Asn Leu Gly Asn Gly Pro Ile Leu Asn Val Leu Val Val
                20                  25                  30

Leu Gly Val Val Leu Leu Gly Gln Phe Val Val Arg Arg
            35                  40                  45
```

```
<210> SEQ ID NO 40
<211> LENGTH: 47
<212> TYPE: PRT
<213> ORGANISM: Artificial Sequence
<220> FEATURE:
<223> OTHER INFORMATION: Novel Sequence

<400> SEQUENCE: 40

Leu Lys Arg Gly Met Pro Arg Val Leu Ser Leu Ile Gly Leu Lys Arg
1               5                   10                  15

Ala Met Leu Ser Leu Ile Asp Gly Lys Gly Pro Ile Arg Phe Val Leu
            20                  25                  30

Ala Leu Leu Ala Phe Phe Arg Phe Thr Ala Ile Ala Pro Thr Arg
        35                  40                  45

<210> SEQ ID NO 41
<211> LENGTH: 15
<212> TYPE: PRT
<213> ORGANISM: Artificial Sequence
<220> FEATURE:
<223> OTHER INFORMATION: Novel Sequence

<400> SEQUENCE: 41

Thr Gly Ala Leu Leu Leu Gln Gly Met Ile Ala Ala Val Asp Thr
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Novel Sequence

<400> SEQUENCE: 42

Thr Gly Ile Ala Val Met Ile Gly Leu Ile Ala Ser Val Gly Ala
1               5                   10                  15

<210> SEQ ID NO 43
<211> LENGTH: 44
<212> TYPE: PRT
<213> ORGANISM: Artificial Sequence
<220> FEATURE:
<223> OTHER INFORMATION: Novel Sequence

<400> SEQUENCE: 43

Gln Thr Glu Asp Ile Arg Asp Val Leu Arg Phe Met Asp Gly Phe Thr
1               5                   10                  15

Thr Leu Lys Glu Asn Ile Met Arg Phe Trp Arg Ser Pro Asn Pro Gly
            20                  25                  30

Ser Trp Val Ser Cys Gln Val Leu Leu Ala Leu Leu
        35                  40

<210> SEQ ID NO 44
<211> LENGTH: 45
<212> TYPE: PRT
<213> ORGANISM: Artificial Sequence
<220> FEATURE:
<223> OTHER INFORMATION: Novel Sequence

<400> SEQUENCE: 44

Lys Gln Thr Ala Met Lys His Leu Leu Ser Phe Lys Lys Glu Leu Gly
1               5                   10                  15

Thr Leu Thr Ser Ala Ile Asn Arg Arg Ser Ser Lys Gln Lys Lys Arg
            20                  25                  30
```

```
Gly Gly Lys Thr Gly Ile Ala Val Met Ile Gly Leu Ile
        35                  40                  45

<210> SEQ ID NO 45
<211> LENGTH: 12
<212> TYPE: PRT
<213> ORGANISM: Artificial Sequence
<220> FEATURE:
<223> OTHER INFORMATION: Novel Sequence

<400> SEQUENCE: 45

Phe Arg Arg Glu Leu Asp Ala Leu Gly His Glu Leu
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Novel Sequence

<400> SEQUENCE: 46

Phe Lys Lys Glu Leu Gly Thr Leu Thr Ser Ala Ile
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Novel Sequence

<400> SEQUENCE: 47

Asp Ser Phe Lys Lys Gly Leu Pro Arg
1               5

<210> SEQ ID NO 48
<211> LENGTH: 9
<212> TYPE: PRT
<213> ORGANISM: Artificial Sequence
<220> FEATURE:
<223> OTHER INFORMATION: Novel Sequence

<400> SEQUENCE: 48

Asn Met Leu Lys Arg Gly Met Pro Arg
1               5

<210> SEQ ID NO 49
<211> LENGTH: 34
<212> TYPE: PRT
<213> ORGANISM: Artificial Sequence
<220> FEATURE:
<223> OTHER INFORMATION: Novel Sequence

<400> SEQUENCE: 49

Phe Arg Gln Leu Asp Asn Ser Arg Thr Arg Gln Phe Thr Pro His His
1               5                   10                  15

Leu Asn Cys Val Ile Ser Ser Val Tyr Glu Gly Thr Arg Asp Gly Val
            20                  25                  30

Gly Ala

<210> SEQ ID NO 50
<211> LENGTH: 37
<212> TYPE: PRT
<213> ORGANISM: Artificial Sequence
```

```
<220> FEATURE:
<223> OTHER INFORMATION: Novel Sequence

<400> SEQUENCE: 50

Leu Glu Glu Leu Lys Asn Glu Ala Val Arg His Phe Pro Arg Ile Trp
1               5                   10                  15

Leu His Ser Leu Gly Gln His Ile Tyr Glu Thr Tyr Gly Asp Thr Trp
            20                  25                  30

Thr Gly Val Glu Ala
        35

<210> SEQ ID NO 51
<211> LENGTH: 44
<212> TYPE: PRT
<213> ORGANISM: Artificial Sequence
<220> FEATURE:
<223> OTHER INFORMATION: Novel Sequence

<400> SEQUENCE: 51

Thr Trp Thr Gly Val Glu Ala Leu Ile Arg Ile Leu Gln Gln Leu Leu
1               5                   10                  15

Phe Ile His Phe Arg Ile Gly Cys Arg His Ser Arg Ile Gly Ile Ile
            20                  25                  30

Gln Gln Arg Arg Thr Arg Asn Gly Ala Ser Lys Ser
        35                  40

<210> SEQ ID NO 52
<211> LENGTH: 13
<212> TYPE: PRT
<213> ORGANISM: Artificial Sequence
<220> FEATURE:
<223> OTHER INFORMATION: Novel Sequence

<400> SEQUENCE: 52

Asp Phe His Arg Phe Ser Tyr Ile Arg Asp Arg Arg Ala
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Novel Sequence

<400> SEQUENCE: 53

Arg His Ser Arg Ile Gly Ile Ile Gln Gln Arg Arg Thr
1               5                   10

<210> SEQ ID NO 54
<211> LENGTH: 18
<212> TYPE: PRT
<213> ORGANISM: Artificial Sequence
<220> FEATURE:
<223> OTHER INFORMATION: Novel Sequence

<400> SEQUENCE: 54

Glu Phe Gly Asn Thr Phe Ser Val Pro Asp Pro Leu Arg Glu Val Gln
1               5                   10                  15

Arg Leu

<210> SEQ ID NO 55
<211> LENGTH: 19
<212> TYPE: PRT
<213> ORGANISM: Artificial Sequence
```

```
<220> FEATURE:
<223> OTHER INFORMATION: Novel Sequence

<400> SEQUENCE: 55

Thr Tyr Gly Asp Thr Trp Thr Gly Val Glu Ala Leu Ile Arg Ile Leu
1               5                   10                  15

Gln Gln Leu

<210> SEQ ID NO 56
<211> LENGTH: 12
<212> TYPE: PRT
<213> ORGANISM: Artificial Sequence
<220> FEATURE:
<223> OTHER INFORMATION: Novel Sequence

<400> SEQUENCE: 56

Trp Leu Trp Ser Glu Gly Gln Gly Ala Val Phe Tyr
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Novel Sequence

<400> SEQUENCE: 57

Arg Ile Trp Leu His Ser Leu Gly Gln His Ile Tyr
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Novel Sequence

<400> SEQUENCE: 58

Leu Ser Lys Tyr Leu Ser Asp Leu Leu Phe Val Phe
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Novel Sequence

<400> SEQUENCE: 59

Leu Ile Arg Ile Leu Gln Gln Leu Leu Phe Ile His Phe
1               5                   10

<210> SEQ ID NO 60
<211> LENGTH: 31
<212> TYPE: PRT
<213> ORGANISM: Artificial Sequence
<220> FEATURE:
<223> OTHER INFORMATION: Novel Sequence

<400> SEQUENCE: 60

Ile Gly Ala Val Leu Pro Lys Gly Ser Phe Lys Ser Thr Ile Met Arg
1               5                   10                  15

Val Leu Asp Glu Met Glu Val Leu Gly Val Arg Ile Met Pro Arg
            20                  25                  30
```

```
<210> SEQ ID NO 61
<211> LENGTH: 31
<212> TYPE: PRT
<213> ORGANISM: Artificial Sequence
<220> FEATURE:
<223> OTHER INFORMATION: Novel Sequence

<400> SEQUENCE: 61

Glu Asp Gln Gly Pro Gln Arg Glu Pro Tyr Asn Asp Trp Thr Leu Glu
1               5                   10                  15

Leu Leu Glu Glu Leu Lys Asn Glu Ala Val Arg His Phe Pro Arg
            20                  25                  30

<210> SEQ ID NO 62
<211> LENGTH: 64
<212> TYPE: PRT
<213> ORGANISM: Artificial Sequence
<220> FEATURE:
<223> OTHER INFORMATION: Novel Sequence

<400> SEQUENCE: 62

Pro Gln Ala Ser Ile Arg Gln Ser Gln Glu Glu Pro Glu Asp Leu Arg
1               5                   10                  15

Pro Glu Ile Arg Ile Gln Glu Leu Arg Arg Ile Gly Asp Glu Phe Asn
            20                  25                  30

Glu Thr Tyr Thr Arg Arg Val Phe Ala Asp Tyr Arg Glu Ala Glu Asp
        35                  40                  45

His Pro Gln Met Val Ile Leu Gln Leu Leu Arg Phe Ile Phe Arg Leu
    50                  55                  60

<210> SEQ ID NO 63
<211> LENGTH: 68
<212> TYPE: PRT
<213> ORGANISM: Artificial Sequence
<220> FEATURE:
<223> OTHER INFORMATION: Novel Sequence

<400> SEQUENCE: 63

Asp Gln Gly Pro Gln Arg Glu Pro Tyr Asn Asp Trp Thr Leu Glu Leu
1               5                   10                  15

Leu Glu Glu Leu Lys Asn Glu Ala Val Arg His Phe Pro Arg Ile Trp
            20                  25                  30

Leu His Ser Leu Gly Gln His Ile Tyr Glu Thr Tyr Gly Asp Thr Trp
        35                  40                  45

Thr Gly Val Glu Ala Leu Ile Arg Ile Leu Gln Gln Leu Leu Phe Ile
    50                  55                  60

His Phe Arg Ile
 65

<210> SEQ ID NO 64
<211> LENGTH: 50
<212> TYPE: PRT
<213> ORGANISM: Artificial Sequence
<220> FEATURE:
<223> OTHER INFORMATION: Novel Sequence

<400> SEQUENCE: 64

Leu Arg Pro Glu Ile Arg Ile Gln Glu Leu Arg Arg Ile Gly Asp Glu
1               5                   10                  15

Phe Asn Glu Thr Tyr Thr Arg Arg Ala Phe Ala Asp Tyr Arg Glu Ala
            20                  25                  30

Glu Asp His Pro Gln Met Val Ile Leu Gln Leu Leu Arg Phe Ile Phe
```

```
                        35                  40                  45

Arg Leu
    50

<210> SEQ ID NO 65
<211> LENGTH: 53
<212> TYPE: PRT
<213> ORGANISM: Artificial Sequence
<220> FEATURE:
<223> OTHER INFORMATION: Novel Sequence

<400> SEQUENCE: 65

Leu Leu Glu Glu Leu Lys Asn Glu Ala Val Arg His Phe Pro Arg Ile
1               5                   10                  15

Trp Leu His Ser Leu Gly Gln His Ile Tyr Glu Thr Tyr Gly Asp Thr
            20                  25                  30

Trp Thr Gly Val Glu Ala Leu Ile Arg Ile Leu Gln Gln Leu Leu Phe
        35                  40                  45

Ile His Phe Arg Ile
    50

<210> SEQ ID NO 66
<211> LENGTH: 48
<212> TYPE: PRT
<213> ORGANISM: Artificial Sequence
<220> FEATURE:
<223> OTHER INFORMATION: Novel Sequence

<400> SEQUENCE: 66

Arg Asn Val Ala Arg Gln Leu His Ile Pro Leu Gln Ser Glu Pro Val
1               5                   10                  15

Val Thr Asp Ala Phe Leu Ala Val Ala Gly His Ile Phe Ser Ala Gly
            20                  25                  30

Ile Thr Trp Gly Lys Val Val Ser Leu Tyr Ser Val Ala Ala Gly Leu
        35                  40                  45

<210> SEQ ID NO 67
<211> LENGTH: 52
<212> TYPE: PRT
<213> ORGANISM: Artificial Sequence
<220> FEATURE:
<223> OTHER INFORMATION: Novel Sequence

<400> SEQUENCE: 67

Asn Asp Trp Thr Leu Glu Leu Leu Glu Glu Leu Lys Asn Glu Ala Val
1               5                   10                  15

Arg His Phe Pro Arg Ile Trp Leu His Ser Leu Gly Gln His Ile Tyr
            20                  25                  30

Glu Thr Tyr Gly Asp Thr Trp Thr Gly Val Glu Ala Leu Ile Arg Ile
        35                  40                  45

Leu Gln Gln Leu
    50

<210> SEQ ID NO 68
<211> LENGTH: 53
<212> TYPE: PRT
<213> ORGANISM: Artificial Sequence
<220> FEATURE:
<223> OTHER INFORMATION: Novel Sequence

<400> SEQUENCE: 68

Trp Thr Leu Asp Phe Leu Arg Glu Arg Leu Leu Gly Trp Ile Gln Asp
```

```
                 1               5                  10                 15
Gln Gly Gly Trp Asp Gly Leu Leu Ser Tyr Phe Gly Thr Pro Thr Trp
                 20                  25                 30

Gln Thr Val Thr Ile Phe Val Ala Gly Leu Thr Ala Ser Leu Thr Ile
            35                  40                 45

Trp Lys Lys Met Gly
     50

<210> SEQ ID NO 69
<211> LENGTH: 58
<212> TYPE: PRT
<213> ORGANISM: Artificial Sequence
<220> FEATURE:
<223> OTHER INFORMATION: Novel Sequence

<400> SEQUENCE: 69

Trp Thr Leu Glu Leu Leu Glu Glu Leu Lys Asn Glu Ala Val Arg His
1               5                  10                 15

Phe Pro Arg Ile Trp Leu His Ser Leu Gly Gln His Ile Tyr Glu Thr
                 20                  25                 30

Tyr Gly Asp Thr Trp Thr Gly Val Glu Ala Leu Ile Arg Ile Leu Gln
            35                  40                 45

Gln Leu Leu Phe Ile His Phe Arg Ile Gly
     50                  55

<210> SEQ ID NO 70
<211> LENGTH: 24
<212> TYPE: PRT
<213> ORGANISM: Artificial Sequence
<220> FEATURE:
<223> OTHER INFORMATION: Novel Sequence

<400> SEQUENCE: 70

Trp Thr Leu Asp Phe Leu Arg Glu Arg Leu Leu Gly Trp Ile Gln Asp
1               5                  10                 15

Gln Gly Gly Trp Val Arg Leu Leu
            20

<210> SEQ ID NO 71
<211> LENGTH: 25
<212> TYPE: PRT
<213> ORGANISM: Artificial Sequence
<220> FEATURE:
<223> OTHER INFORMATION: Novel Sequence

<400> SEQUENCE: 71

Trp Thr Leu Glu Leu Leu Glu Glu Leu Lys Asn Glu Ala Val Arg His
1               5                  10                 15

Phe Pro Arg Ile Trp Leu His Ser Leu
            20                  25

<210> SEQ ID NO 72
<211> LENGTH: 12
<212> TYPE: PRT
<213> ORGANISM: Artificial Sequence
<220> FEATURE:
<223> OTHER INFORMATION: Novel Sequence

<400> SEQUENCE: 72

Val Phe Gln Ser Trp Trp Asp Arg Asn Leu Gly Arg
1               5                  10
```

```
<210> SEQ ID NO 73
<211> LENGTH: 12
<212> TYPE: PRT
<213> ORGANISM: Artificial Sequence
<220> FEATURE:
<223> OTHER INFORMATION: Novel Sequence

<400> SEQUENCE: 73

His Phe Pro Arg Ile Trp Leu His Ser Leu Gly Gln
1               5                   10
```